(12) United States Patent
Trapero Martin et al.

(10) Patent No.: US 11,116,448 B1
(45) Date of Patent: Sep. 14, 2021

(54) MULTI-SENSOR WEARABLE PATCH

(71) Applicant: ANEXA LABS LLC, Mountain View, CA (US)

(72) Inventors: Ana Trapero Martin, Salamanca (ES); Michael Daniel Vermeer, Kitchener (CA); Mathew Asselin, Toronto (CA); Joel Steven Ironstone, Toronto (CA)

(73) Assignee: ANEXA LABS LLC, Mountain View, CA (US)

( * ) Notice: Subject to any disclaimer, the term of this patent is extended or adjusted under 35 U.S.C. 154(b) by 0 days.

(21) Appl. No.: 17/161,515

(22) Filed: Jan. 28, 2021

(51) Int. Cl.
*A61B 5/00* (2006.01)

(52) U.S. Cl.
CPC ...... *A61B 5/6833* (2013.01); *A61B 2562/029* (2013.01); *A61B 2562/0219* (2013.01); *A61B 2562/0271* (2013.01); *A61B 2562/166* (2013.01)

(58) Field of Classification Search
CPC A61B 5/25; A61B 5/28; A61B 5/6811; A61B 5/6823; A61B 5/6833; A61B 2562/0271; A61B 2562/0219; A61B 2562/166; A61B 2562/029
See application file for complete search history.

(56) References Cited

U.S. PATENT DOCUMENTS

| | | | |
|---|---|---|---|
| 9,900,677 B2 | 2/2018 | Hung | |
| 2002/0099286 A1 | 7/2002 | Sandler et al. | |
| 2003/0163287 A1 | 8/2003 | Vock et al. | |
| 2005/0090725 A1 | 4/2005 | Page et al. | |
| 2011/0092790 A1 | 4/2011 | Wilder-Smith et al. | |
| 2012/0088999 A1* | 4/2012 | Bishay | A61B 5/332 600/382 |
| 2012/0209131 A1* | 8/2012 | Jones | A61B 7/04 600/528 |

(Continued)

FOREIGN PATENT DOCUMENTS

| | | | | |
|---|---|---|---|---|
| WO | 2019/204003 A1 | 10/2019 | | |
| WO | WO-2019204003 A1 * | 10/2019 | ............... | H04R 1/46 |

OTHER PUBLICATIONS

Gupta, P., Moghimi, M., Jeong, Y., Gupta, D., Inan, O., Ayazi, F. Precision Wearable Accelerometer Contact Microphones for Longitudinal Monitoring of Mechano-acoustic Cardiopulmonary Signals. 2020.NPJ Digital Medicine. 3:19; https://doi.org/10.1038/s41746-020-0225-7 (Year: 2020).*

(Continued)

*Primary Examiner* — Eun Hwa Kim
(74) *Attorney, Agent, or Firm* — Nixon Peabody LLP; Matthew T. Kitces

(57) ABSTRACT

A multi-sensor smart patch is disclosed that can be worn by a user to monitor multiple physiological systems of the user. The multi-sensor smart patch can make use of two or more acoustic sensors, such as accelerometer contact microphones (ACMs), to collect acoustic data from multiple locations on the user's body. The multi-sensor smart patch can include electrodes for detecting the heart's electrical activity and/or assessing the user's bioimpedance. The multi-sensor smart patch can provide useful data associated with the user's cardiovascular system, respiratory system, and electrical characteristics. The multi-sensor smart patch can be in the form of a reusable electronics module couplable to a disposable patch adhesive.

20 Claims, 25 Drawing Sheets

(56) References Cited

U.S. PATENT DOCUMENTS

| | | |
|---|---|---|
| 2013/0030259 A1* | 1/2013 | Thomsen ............ A61B 5/02028 600/301 |
| 2014/0125491 A1 | 5/2014 | Park et al. |
| 2015/0282758 A1* | 10/2015 | Chang ................ A61B 5/02055 600/301 |
| 2016/0015359 A1 | 1/2016 | Emmanouilidou et al. |
| 2016/0120433 A1* | 5/2016 | Hughes ................ G16H 80/00 600/483 |
| 2017/0180870 A1 | 6/2017 | Hung et al. |
| 2017/0238833 A1* | 8/2017 | Felix .................... A61B 5/6823 |
| 2017/0290546 A1 | 10/2017 | Antonio et al. |
| 2018/0110450 A1 | 4/2018 | Lamego et al. |
| 2018/0184902 A1 | 7/2018 | Meyerson et al. |
| 2019/0105011 A1 | 4/2019 | Kim et al. |
| 2019/0216420 A1 | 7/2019 | Hsu et al. |
| 2020/0054292 A1* | 2/2020 | Govari ................ G16H 50/20 |
| 2021/0000351 A1* | 1/2021 | Murali ................. A61B 5/726 |

OTHER PUBLICATIONS

Gupta, Pranav, et al., "Precision High-Bandwidth Out-Of-Plane Accelerometer as Contact Microphone for Body-Worn Auscultation Devices," Georgia Institute of Technology, Atlanta, Georgia, USA, Solid-State Sensors, Acutators and Microsystems Workshop, Hilton Head Island, South Caroline, Jun. 3-7, 2018.

Gupta, Pranav, et al., "Precision wearable accelerometer contact microphones for longitudinal monitoring of mechano-acoustic cardiopulmonary signals," npj Digital Medicine, Feb. 12, 2020.

* cited by examiner

MULTI-SENSOR WEARABLE PATCH

TECHNICAL FIELD

The present disclosure relates to medical devices generally and more specifically to wearable medical devices.

BACKGROUND

Recent advances in electronics miniaturization, faster microprocessors, new sensor technologies, ubiquitous wireless networks, and artificial intelligence (AI)-based data analysis techniques have enabled the development of wearable devices for remote patient monitoring. An emerging application of wearable devices is with outpatient cardiopulmonary assessment, monitoring, and rehabilitation.

Cardiovascular diseases (CVDs) are the leading cause of death globally; more people die annually from CVDs than from any other cause. According to the World Health Organization, an estimated 17.9 million people died from CVDs in 2016, representing 31% of all global deaths. Of these deaths, 85% are due to heart attack and stroke.

People with cardiovascular disease or those who are at high cardiovascular risk (e.g., due to the presence of one or more risk factors such as hypertension, diabetes, hyperlipidemia, or an already established disease) can greatly benefit from early detection and management using counselling and medicines, as appropriate.

Many patients with prior Heart Failure (HF) experience episodes of acute decompensated heart failure (ADHF). Both in Europe and in the United States, ADHF is responsible for nearly 1 million hospitalizations annually, and hospitalization rates from ADHF are increasing with the aging population. In fact, ADHF is now the leading cause of hospital admissions in the United States among patients that are 65 years or older.

Additionally, many individuals suffer from pulmonary diseases, with or without concurrent CVDs. However, unless a patient is exhibiting significant symptoms associated with a pulmonary condition, the patient's respiratory system may not be monitored often. Some patients only have their respiratory system monitored at annual physical examinations, or even less often. Without proactive monitoring for pulmonary function, some pulmonary diseases can progress farther than otherwise necessary.

There is a need for an improved wearable device capable of monitoring a user, such as to detect signs of a future, imminent, or present HF episode, or such as to detect anomalies associated with pulmonary function.

SUMMARY

The term embodiment and like terms are intended to refer broadly to all of the subject matter of this disclosure and the claims below. Statements containing these terms should be understood not to limit the subject matter described herein or to limit the meaning or scope of the claims below. Embodiments of the present disclosure covered herein are defined by the claims below, supplemented by this summary. This summary is a high-level overview of various aspects of the disclosure and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this disclosure, any or all drawings and each claim.

Certain aspects and features of the present disclosure relate to a multi-sensor smart patch that can be worn by a user to monitor multiple physiological functions of the user. The smart patch can make use of at least one acoustic sensor to collect acoustic data from a location on the user's body. In some cases, two or more acoustic sensors can be used to collect acoustic data from multiple locations on the user's body, such as for the purpose of triangulating the sources of sounds. Such acoustic sensors can be accelerometer contact microphones (ACM), which can be coupled to a mainboard via application-specific integrated circuits.

In some cases, the smart patch can include electrodes for detecting electrical activity from the body of the user and/or assessing the user's bioimpedance. In some cases, other sensors can be used to acquire additional medically relevant data. For example, an environmental sensor (e.g., a temperature/humidity sensor) can be used to acquire temperature and humidity data from the user's skin. In another example, a photoplethysmography (PPG) sensor can be used to acquire additional cardiac data (e.g., blood oxygenation data and heart rate data).

The smart patch can be in the form of a reusable electronics module couplable to a disposable, flexible patch. The electronics module can contain various sensors and components, including a battery for supplying power and a wireless module for establishing a wireless connection, such as with a user device (e.g., smartphone). The electronics module can be designed to couple to the flexible patch, such as by fitting within a receptacle of the flexible patch. Electrode contacts of the electronics module can make contact with contact pads of the flexible patch, which can electrically couple the electrode contacts of the electronics module to electrode pads (e.g., hydrogel electrodes) located on a user-facing surface of the flexible patch. Thus, when the user-facing surface of the flexible patch is adhered to the user, the electronics module will be able to acquire and send electrical signals through the electrode pads, such as to acquire electrocardiography (ECG) data and/or bioimpedance data. When desired, the electronics module can be removed from the flexible patch for charging, maintenance, or other use. The flexible patch can remain adhered to the user's skin for future use or can be removed for disposal.

The smart patch can be worn comfortably and inconspicuously for extended periods of time, while simultaneously collecting useful data associated with the user's cardiovascular system, respiratory system, and other health metrics.

BRIEF DESCRIPTION OF THE DRAWINGS

The specification makes reference to the following appended figures, in which use of like reference numerals in different figures is intended to illustrate like or analogous components.

DETAILED DESCRIPTION

Figure 1:
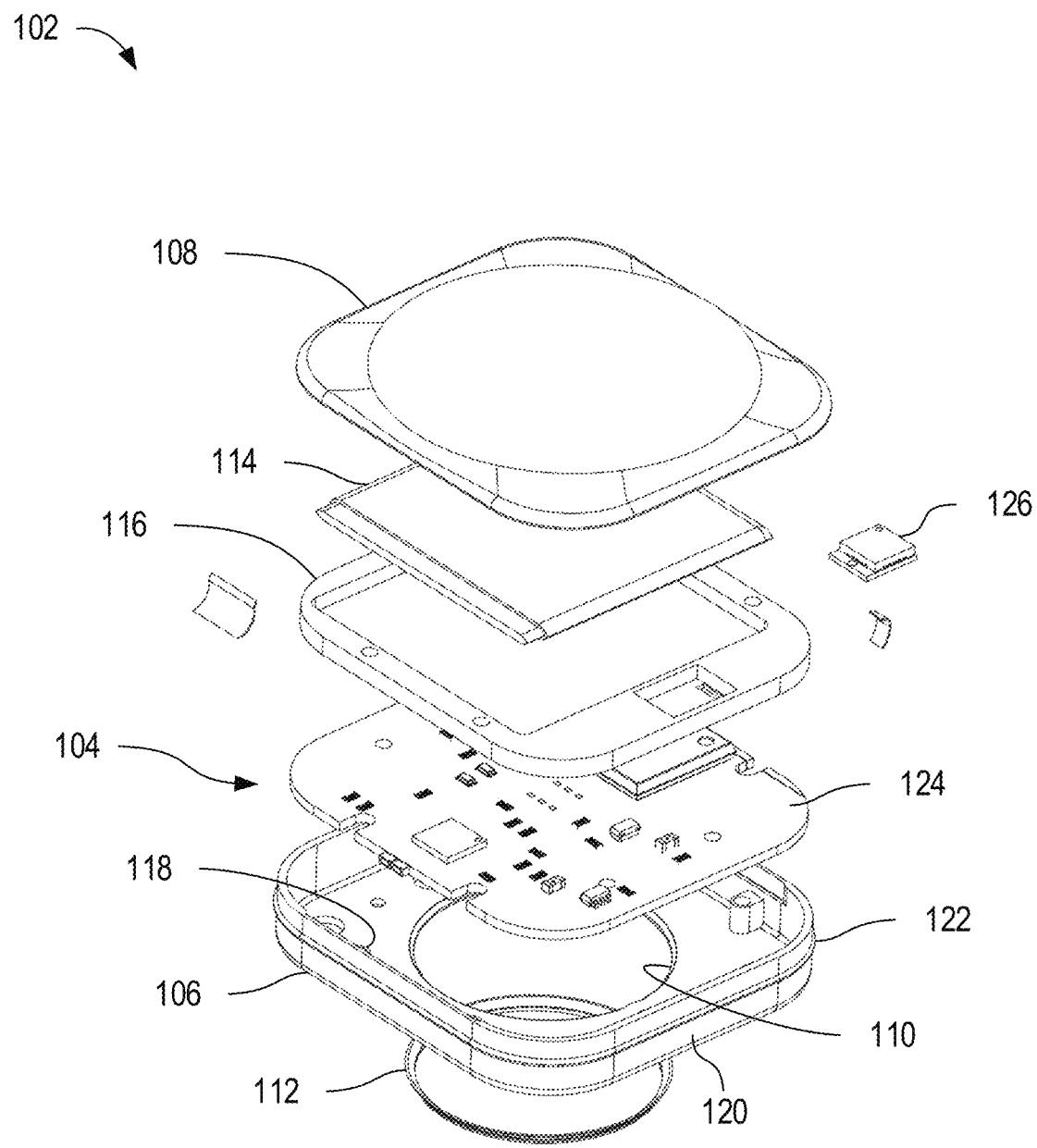
FIG. 1 is an exploded isometric view of an electronics module usable in a smart patch, according to certain aspects of the present disclosure.

Certain aspects and features of the present disclosure relate to a multi-sensor smart patch that can be worn by a user to monitor multiple physiological systems of the user. In some cases, the multi-sensor smart patch can make use of one or more acoustic sensors, such as accelerometer contact microphones (ACMs), to collect acoustic data from one or more locations on the user's body. In some cases, the multi-sensor smart patch can include electrodes for detecting cardiac electrical activity and/or assessing the user's bioimpedance. The multi-sensor smart patch can provide useful data associated with the user's cardiovascular system, respiratory system, and other relevant health metrics. The multi-sensor smart patch can be in the form of a reusable electronics module coupled to a disposable patch adhesive.

Wearable health devices provide an effective means for capturing important physiological metrics for medical assessment, diagnostics, and research. Such devices are also useful for consumer self-health tracking applications.

Remote health monitoring via a low-cost, unobtrusive, wearable device can provide an efficient alternative to on-site clinical assessment and monitoring of patients with cardiopulmonary disease. Such systems equipped with non-invasive wearable sensors can be viable diagnostic tools for healthcare personnel to monitor important physiological signs and activities of patients in real-time.

There are often clear physiological changes preceding acute cardiac events, but detection has traditionally required invasive catheters and implants. By analyzing physiological trends, certain aspects and features of a wearable patch system disclosed herein can facilitate early detection of signs of cardiac decline before traditional symptoms appear. Such a system can allow clinicians to implement therapeutic interventions and prevent hospitalizations.

Cardiac diseases can affect other aspects of an individual, such as pulmonary function. Therefore, it can be beneficial to understand the interactions between the cardiovascular system and other systems, such as the pulmonary system. Certain aspects of the present disclosure relate to a multi-sensor patch capable of collecting not only cardiovascular data, but also data associated with a user's glucose levels, body composition, and/or respiratory parameters (e.g., pulse oximetry, respiration rate, rhythm, effort, sounds, and the like). In some cases, respiration monitoring can potentially help diagnose and treat patients with asthma, chronic obstructive pulmonary disease (COPD), and sleep apnea, among other diseases and disorders. Without the use of a multi-sensor patch as disclosed herein, traditional methods of respiratory monitoring generally involve spirometry and exhaustive and/or obtrusive physical examinations in a clinic setting.

Many of the wearable devices available today have a limited number of sensors that do not provide clinicians with a complete picture of the patient's health status—only providing narrow data about a given physiological system. Certain aspects of the present disclosure relate to a comprehensive multi-sensor wearable patch capable of synchronized vital signs monitoring of a user remotely. Certain aspects of the present disclosure also relate to a wearable patch system that enables accurate, real-time assessment of cardiovascular and cardiopulmonary systems. To assess the patient in a comprehensive way, the wearable device can integrate multiple sensors in a single patch for detection of the user's cardiac electrical activity, cardiac mechanical activity, respiratory function, other core vitals, and physical activity, as well as ambient parameters (e.g., temperature, humidity, pressure, and other parameters of the environment surrounding the user).

Certain aspects and features of the present disclosure relate to a multi-sensor smart patch that captures physiological metrics for cardiopulmonary and general health monitoring. The smart patch has a small form factor and is comfortable to wear on the chest underneath clothing. The patch enables continuous ambulatory monitoring of human vital signs in daily life (e.g., during work, at home, during sport activities, etc.) or in a clinical environment, with the advantage of minimizing discomfort and interference with normal human activities. The patch provides real-time acquisition of vital signs and health status monitoring over extended periods (days/weeks) and outside clinical environments.

The smart patch comprises two components that attach and work together: a reusable electronics module and a disposable patch adhesive. The electronics module includes a sealed housing that encloses all the electronic circuitry and sensors for recording, storing, processing, and wirelessly transmitting the patient's physiological health metrics. As used herein, the term "user" can refer to a patient making use of the smart patch.

The electronics module snaps into a receptacle contained on a flexible patch with an adhesive layer at the bottom. The receptacle is provided on the top side of the patch and receives and securely holds the electronics module in place. When the electronics module is inserted into the receptacle by snapping it in place, a moisture-resistant seal is created around the perimeter preventing moisture/liquid from entering the receptacle. In some cases, the electronics module itself is water-resistant or waterproof regardless of whether or not it is inserted into the receptacle.

The receptacle contains a fixed opening in the center which mirrors the size of the electronics module's sensor window, enabling the electronic device's sensors to interface with the user's skin in order to capture physiological data. In some cases, this opening can be filled with a window similar to the sensor window described with reference to the electronics module. Non-contact measurements are enabled through the sensor window via optical sensing and/or electromagnetic signaling, among other methods. In the base of the receptacle are additional openings which allow for some electronic module sensors to interface directly with the skin.

When the electronics module is inserted into the patch receptacle, multiple electrodes on the bottom surface of the electronics module individually come in contact with corresponding electrode contacts on the surface of the receptacle to facilitate interoperability. The receptacle contacts are electrically conductive units that allow electrical signals to be transferred between the patch's electrodes that are in contact with the user's skin and the electronics module circuitry. For example, electrocardiography data is sensed via a pair of electrocardiogram (ECG) electrodes provided on the patch, and bioimpedance data is collected via an array of bioimpedance electrodes.

Using the multiple electrodes and sensors which interface with the device's circuitry, the smart patch captures, measures, or generates various types of data, referred to herein as patch data, over long periods of time. Patch data can include i) physiological data, ii) activity data, iii) location data, iv) environment data, or v) any combination of i-iv.

Patch data can include physiological data. Physiological data can include i) cardiac electrical activity data, such as ECG data; ii) cardiac mechanical activity data, such as phonocardiogram (PCG) data, seismocardiogram (SGC) data, and/or ballistocardiogram (BCG) data; iii) respiratory function data, such as lung sounds, inhalation cycle data, and/or expiration cycle data; iv) bioimpedance data (e.g., electrodermal activity response data, such as to monitor the response of the user's sympathetic system (e.g., sweat gland permeability from detected skin impedance variations from bioimpedance data)); v) core vitals data, such as heart rate data (e.g., rate of heart beats), pulse rate data (e.g., rate of palpable blood pressure increases throughout the body), heart rate variability data, blood pressure data, respiratory rate data, blood oxygen saturation data, blood glucose level data, body temperature data, skin moisture (e.g., sweat) data, hydration level data, body fat and muscle composition data, and basal metabolic rate (BMR) data; vi) electromyography (EMG) data, such as to detect activation of certain muscles (e.g., chest muscles); vii) gastric data, such as audio data associated with the alimentary canal; iix) any combination of i-vii.

Patch data can include activity data. Activity data can include data associated with the user's physical activity, such as actigraphy data, motion evaluation data, step count data, body position data, sleep pattern data, fall detection data, stress evaluation data, basic energy (e.g., calorie) requirement data (e.g., as determined from BMR), and the like.

Patch data can include location data. Location data can include user location data and/or wearable position (e.g., with respect to the user's body or skin) data. Location data can include global positioning system (GPS) coordinates (e.g., to correlate with patient health metrics, fall location, etc.). In some cases, the smart patch may receive the semantic location of the electronic device via the network interface. For example, based on GPS receiver location data, the electronic device can be determined to be at Central Park in New York City. Wearable position data can include information about the location of the smart patch with respect to the user's body or skin. In an example, radar sensors can be used alone or in combination with other sensors (e.g., an inertial measurement unit (IMU)) to determine when the lower surface of the patch is attached to the body of a user.

Patch data can include environmental sensor data. In some cases, environmental data can include data about the ambient environment (e.g., ambient conditions surrounding the smart patch and/or the user). For example, an air pressure sensor, temperature sensor, or humidity sensor may be used to acquire ambient air pressure, ambient temperature, or ambient humidity data about the ambient environment (e.g., the room or other space in which the user is located). In some cases, environmental data can include data about a constrained environment. As used herein, a constrained environment can be an environment that is enclosed to facilitate the acquisition of physiological data. In an example, a constrained environment can be an enclosed, controlled space adjacent to the skin of a user. In such an example, a temperature or humidity sensor positioned to acquire data from that constrained environment can be used to measure temperature data or humidity data of the user's skin. In some cases, environmental data for an ambient environment can include data associated with barometric pressure, altitude, local relative humidity, local air temperature, and the like. In some cases, environmental data for a constrained environment can include data associated with temperature within the controlled space, the temperature of the user's skin, humidity within the controlled space, the humidity of the user's skin, and the like.

In some cases, the flexible patch is intended to be disposable. The electronics module, however, is reusable and can be transferred to successive patches for future monitoring of the same user or other users. In some cases, the electronics module can be removed from the patch receptacle while the flexible patch remains on the chest, allowing the electronics module to be recharged and placed back into the receptacle for further monitoring without needing to replace the flexible patch. Since the patch electrodes remain in the same location on the chest, this functionality allows for long term physiological monitoring in a consistent manner without introducing changes that may be caused by different electrode/sensor locations. Capturing physiological data from the same location eliminates artifacts in the patient data. Leaving the adhesive in the same location while the electronics module is recharged also reduces irritation or damage to the user's skin which would result from the repeated application and removal of patch adhesives. In some cases, the flexible patch is designed to be worn for time periods on the order of hours, days, and/or weeks.

Additionally, the smart patch's reusable electronics module reduces electronics waste while providing cost savings. Certain aspects and features of the present disclosure involve improvements over patch devices that contain packaged electronics and that are mechanically rigid. Such mechanically rigid devices may not be suitable for repeated use, may be undesirably conspicuous, or may not be suitable for long-term use.

As described herein, the electronics module can be coupled to a flexible patch (e.g., via a receptacle) for placement on a user's body. In some cases, the electronics module can be coupled to other types of attachment modules. Examples of suitable attachment modules include flexible patches, rigid patches, handheld devices, medical devices (e.g., electronic stethoscopes), clothing, accessories, or the like. The attachment module can be any module suitable for receiving the electronics module and facilitating the placement or securing of one or more sensors and/or electrodes of the electronics module against the skin of the user.

These illustrative examples are given to introduce the reader to the general subject matter discussed here and are not intended to limit the scope of the disclosed concepts. The following sections describe various additional features and examples with reference to the drawings in which like numerals indicate like elements, and directional descriptions are used to describe the illustrative embodiments but, like the illustrative embodiments, should not be used to limit the present disclosure. The elements included in the illustrations herein may not be drawn to scale.

FIG. 1 is an exploded isometric view of an electronics module 102 usable in a smart patch, according to certain aspects of the present disclosure. When assembled, the electronics module 102 can be sealed against water, which can include being waterproof or water-resistant. The electronics module 102 has a small form factor which helps to reduce the overall size of the smart patch. As used herein, the term "top" can refer to a direction away from the user's skin when the electronics module 102 is worn by a user (e.g., upwards as seen in FIG. 1), and the term "bottom" can refer to a direction towards the user's skin when the electronics module 102 is worn by a user (e.g., downwards as seen in FIG. 1).

The enclosure of the electronics module 102 includes a bottom portion 106 and top cover 108 that are sealed together to house and protect the electronics 104 of the device. Integrated sensors capture data through the sensor window 112 placed in a sensor window opening 110 of the bottom portion 106, as well as via electrodes and/or sensors that protrude from the bottom of the bottom portion 106, such as through sensor opening 118.

The top cover 108 of the electronics module snap-fits onto the bottom portion 106, although that need not always be the case. As an alternative to the snap-fit mechanism used, other suitable means to seal the two portions of the electronics module 102 may be used. Some alternative sealing methods include welding metals, using silicone sealants, or polymer adhesives. In some cases, the described methods ensure a permanent or semi-permanent seal that can withstand thermal and/or mechanical stresses. The lateral exterior walls 120 of the bottom portion 106 can include a number of interlocking features 122 (e.g., grooves and/or lips) that match corresponding interlocking features (e.g., corresponding grooves and/or lips) on the flexible patch's receptacle walls, as disclosed herein.

In some cases, the external surface of the top cover 108 includes a flat portion and one or more curved portions. For illustrative purposes, the flat surface is represented by the circle in the center of the top cover 108, and the curved portions result from the gradual sloping from the circle edges towards the lateral sides of the square perimeter of the top cover 108. In some cases, the flat surface on the top cover 108 could be shaped as a square, oval, or other shapes. In some cases, however, the top cover 108 can be shaped in other fashions.

In some cases, the enclosure of the electronics module 102 (e.g., the bottom portion 106 and top cover 108) can be made from non-corrosive, chemically resistant materials that also can withstand high temperature fluctuations. The rigid material of the housing could be ceramic, metal, plastic, polycarbonate (PC), Acrylonitrile Butadiene Styrene (ABS), PC/ABS blends, polymer composites, composite fiber, etc. In some cases, the housing can dissipate heat from the components (e.g., electronics 104) within the electronics module 102. Moreover, the housing can be electromagnetically shielded and block or redirect radiation away from the user's body.

In some cases, the electronics module 102 incorporates a single printed circuit board (PCB) 124 where the microcontroller, antennas, memory, sensors, and other electronic components are integrated. While described herein with reference to a single PCB 124, in some cases, components that would have been integrated into a single PCB 124 can alternatively be integrated into multiple PCBs and can be suitably communicatively coupled. Memory components can be used to store raw sensor data collected by sensors of the electronics module 102, intermediate calculations, computed health metrics, and other data. The PCB 124 can be a multilayer PCB, with components on both sides (e.g., both faces). The PCB 124 can be positioned on the bottom inner surface of the enclosure (e.g., on the bottom inner surface of the bottom portion 106). The PCB 124 can provide a space-saving design whereby the upper side (e.g., the side pointing away from the skin when in use, such as away from the sensor window 112) contains components such as a microcontroller, memory, wireless module, filters, analog-to-digital converter (ADC), digital-to-analog converter (DAC), and/or power management components. The physiological sensors can be integrated into the bottom of the PCB 124 facing down (e.g., towards the user's skin when the smart patch is affixed to the chest, such as towards the sensor window 112). The placement of all the physiological sensors on the bottom of the PCB 124 facilitates data collection using non-contact sensors (e.g., working through the sensor window 112 located on the base of the electronics module 102) or via integrated contact sensors and electrode arrays that extend through the base of the electronics module 102, such as via sensor openings 118 (e.g., for collecting measurements via direct contact or close contact with the skin of the user).

The sensor window 112 can be transparent or translucent to the wavelengths used by the non-contact sensors. In some cases, the sensor window 112 may integrate augmenting lenses so signals emitted and/or received by the sensors in the electronics module can be magnified or otherwise altered. The sensor window 112 can integrate into the bottom portion 106 of the housing of the electronics module 102 in a manner that protects the electronics 104 within the device from outside contaminants (e.g., liquid, dust, and/or other particles). The sensor window may be made of materials such as plastic, sapphire crystals, mineral crystals, plexiglass, hesalite crystals, glass, etc.

The disposition of the electrode connectors on the bottom of the PCB 124 simplifies the contact between the electronics module 102 and the flexible patch's connectors, such as through which the ECG and bioimpedance measurements can be made. When assembled, there can be a space (e.g., air gap) between the bottom inner surface of the electronics module 102 and the bottom of the PCB 124, which can help control the accumulation and dissipation of heat inside the enclosure.

Power can be provided to the electronics 104 by a power supply, such as a battery 114. Battery 114 can be positioned spaced apart from other components of the electronics 104, such as inside a pocket of the divider 116. In some cases, when assembled, there can be a space (e.g., air gap) between the top side of the PCB 124 and divider 116. Divider 116 can act as a battery tray to hold battery 114. Keeping the battery 114 spaced apart from the electronics 104 and user's skin can help thermally isolate the battery 114 and the PCB 124 to improve its performance. In some cases, other power supply components, such as inductive charging coils, as well as radio frequency components (e.g., an antenna module 126) can be located on the top side of the divider 116 (e.g., on a side of the divider 116 opposite to the sensors). Any electromagnetic component (e.g., any component capable of radiating electromagnetic energy) can be placed on top of the divider 116 (e.g., opposite the divider 116 from the PCB 124). This placement of such components can help avoid undesirable interference, as well as avoid exposure to the user of electromagnetic radiation.

The divider 116 can be known as a mechanical holder. The divider 116 can provide thermal management and shielding for electromagnetic interference (EMI) and radio frequency interference (RFI). The divider 116 can be made of a carbon-cenosphere composite or any other material or multilayer structure with similar insulating and shielding characteristics. In some cases, the divider 116 can be manufactured with certain plastics or metals that require EMI/RFI coatings.

While described with reference to use in a smart patch, the electronics module 102 can be used alone or connected with other devices. In an example, the electronics module 102 can be designed to be used as a smartwatch. In such examples, the electronics module 102 may fit within a receptacle of a watch band, allowing the electronics module 102 to make certain recordings while held against the user's wrist by the watch band. In some cases, the electronics module 102 can be removed from the watch band and placed into another receptacle, such as a receptacle of an adhesive patch. Thus, the electronics module 102 may be movable between receptacles to be used for different purposes (e.g., placed within a watch band to be used as a smartwatch or placed within an adhesive patch to be used as a smart patch). In some cases, electronics module 102 can include additional components to further facilitate complementary uses. In the smartwatch example, the electronics module 102 may include a user-facing display (e.g., a touchscreen display) and/or other input components (e.g., a watch crown and/or physical buttons). In another example, the electronics module 102 can be placed within a receptacle designed to provide an easy-to-hold grip and smooth bottom surface to slide in contact with the skin of a user. These grip and slide features can facilitate the use of the electronics module 102 as an auscultation device in a fashion similar to that of a stethoscope. In some cases, lanyards, loops, or other retention devices can be coupled to the electronics module 102 when used as an auscultation device to avoid accidental damage if the electronics module 102 were to be dropped.

Figure 2:
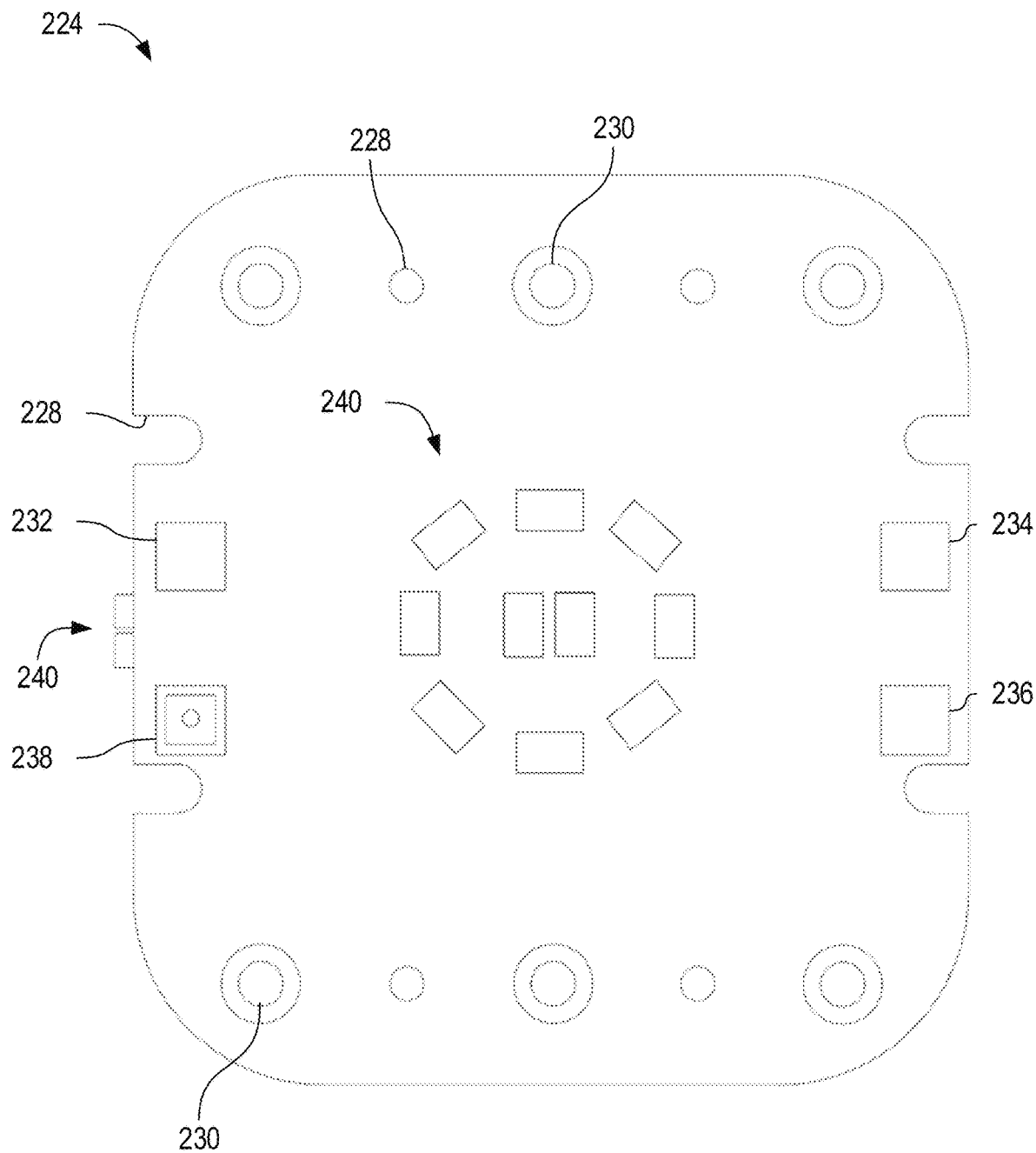
FIG. 2 is a bottom view of a PCB usable in an electronics module that is usable in a smart patch, according to certain aspects of the present disclosure.

FIG. 2 is a bottom view of a PCB 224 usable in an electronics module that is usable in a smart patch, according to certain aspects of the present disclosure. PCB 224 can be PCB 124 of FIG. 1. The shape of the PCB 224 conforms to the shape of the electronics module housing (e.g., PCB 124 conforming to the shape of the electronics module 102 of FIG. 1). In some cases, the PCB 224 can include alignment openings 228 (e.g., holes, slots, or other openings) to facilitate aligning the PCB 224 with the electronics module housing (e.g., the bottom portion of the electronics module housing). In some cases, the PCB 224 can be secured to the electronics module housing through the use of screws or other fasteners, which may optionally pass through the alignment openings 228. In some cases, the PCB 224 can be secured to the electronics module housing without the use of additional fasteners, such as via a snap-fit or use of an adhesive material. In some cases, the PCB 224 can rest upon supports of the bottom portion of the electronics module housing, such as bosses (e.g., protrusions) or alignment pins, a portion of which can optionally pass through the alignment openings 228.

Integrated on the bottom side of the PCB 224 are six electrode contacts 230 which correspond to the electrodes of the receptacle of the flexible patch. While described with reference to six electrode contacts 230, in some cases additional or fewer electrode contacts can be used. While depicted as circular electrode contacts 230, in some cases the electrode contacts 230 can be square, rectangular, arched, polygonal, or otherwise shaped. The electrode contacts 230 can make contact with corresponding electrode pads of the flexible patch when the electronics module is placed within the receiver of the flexible patch. In some cases, the electrode contacts 230 make direct contact with the skin of a user, such as by extending from the PCB 224 and through electrode openings in the base of the electronics module housing. In some cases, the electrode contacts 230 make indirect contact, such as by contacting an intermediate conductor (e.g., an intermediate conductor placed within the bottom portion of the flexible patch).

In some cases, the electrode contacts 230 can be placed in locations at or near opposite edges of the PCB 224, such as locations adjacent a first edge (e.g., the three electrode contacts 230 seen near the edge of PCB 224 nearest the top of FIG. 2) and locations adjacent a second edge (e.g., the three electrode contacts 230 seen near the edge of PCB 224 nearest the bottom of FIG. 2). In some cases, two electrode contacts 230 at or near opposite edges from one another can form an electrode pair. Electrode contacts 230 of such an electrode pair can be connected to corresponding electrode pads positioned on opposite sides of the flexible patch.

Accelerometer contact microphones (ACMs) 232, 234, 236 can be located on the bottom surface of the PCB 224. In some cases, the ACMs 232, 234, 236 can be located at or near different edges than the electrode contacts 230, such as perpendicular edges. In some cases, an ACM 232 can be located at or near an opposite edge from other ACMs 234, 236, such as at or near a third edge (e.g., the edge of the PCB 224 nearest the left of FIG. 2) and a fourth edge (e.g., the edge of the PCB 224 nearest the right of FIG. 2). A temperature/humidity sensor 238 (e.g., a temperature sensor, a humidity sensor, or a temperature and humidity sensor) can be located adjacent to an ACM 232. In some cases, the ACMs 232, 234, 236 and the temperature/humidity sensor 238 can be arranged in an array, such as a mirrored or symmetrical array, such as with respect to a centerline of or the center of the PCB 224.

The temperature/humidity sensor 238 can be an integrated sensor, and can be used to capture the skin temperature and/or skin humidity level of the user. Skin temperature can be a useful metric to detect fever. Skin temperature is correlated with blood circulation in the analyzed area of the user's body, as well as with the heart rate and metabolic rate of the user. Skin humidity can be important for evaluating dehydration in patients. In some cases, skin humidity data can be useful to improve the accuracy of bioimpedance measurements.

The ACMs 232, 234, 236 can permit the smart patch to function as an auscultation device that can precisely capture cardiopulmonary sounds (e.g., heart sounds and lung sounds), chest wall motion, and BCG signals, among other signals. The interdependency of cardiac and pulmonary health makes continuous monitoring of cardiopulmonary parameters extremely useful for an accurate and timely diagnosis.

Multiple ACM units (e.g., ACMs 232, 234, 236) can be included to capture both heart and lung sounds from different locations on the skin of the user. Further, the use of multiple ACM units can help eliminate artifacts and help capture data with higher accuracy. While any number of ACM units can be used, the use of at least three ACMs 232, 234, 236 can be advantageous. For example, the use of three ACMs 232, 234, 236 instead of one or two enables signal triangulation. Thus, the location of the origin of a particular sound in the body of a user can be determined. Determining the origin location of an auscultatory signal can be useful in diagnosing a user.

In some cases, determining the origin location of an auscultatory signal can include determining a location of the electronics module with respect to the user, determining a location of the auscultatory signal with respect to the electronics module, then using both relative locations to determine a location of the auscultatory signal with respect to the user. In some cases, determining a location of the electronics module with respect to the user can include determining that the electronics module is positioned against the skin of the user and using an assumed location (e.g., a location on the skin above the heart of the user, or other location). In some cases, determining a location of the electronics module with respect to the user can include using other sensor data (e.g., data from the IMU) to estimate a location of the electronics module with respect to the user. Non-contact sensors 240, such as optical and other types of sensors, can be located on the bottom surface of the PCB 224, such as at or near the center of the bottom surface. The non-contact sensors 240 can be arranged in an array that correlates with the outline of the sensor window (e.g., sensor window 112 of FIG. 1) of the electronics module. Thus, non-contact sensors 240 can collect sensor data through the sensor window. In some cases, the number and type of sensors that collect physiological signals through the sensor window can decrease or increase, which can result in use of sensor windows with different possible shapes and sizes. In some cases, more than one sensor window can be used. A plurality of openings and sensor windows may be provided on the bottom surface of the electronics module and configured for transmission and reflection of light rays of determined wavelengths therethrough.

As depicted in FIG. 2, the bottom surface of the PCB 224 may comprise various non-contact sensors 240 such as optical sensors for obtaining photoplethysmography (PPG) measurements that can be used to detect blood volume changes in the microvascular bed of the user's tissue. PPG can be used to monitor the user's heart rate (HR), heart rate variability (HRV), respiration rate, oxygen saturation, blood glucose, blood pressure estimations, and other physiological metrics. The sensor system 240 for PPG measurements may include one or more light emitters and one or more photodetectors. Exemplary light emitters can include, without limitation, light-emitting diodes (LEDs), incandescent lights, fluorescent lights and lasers. The LED may be a green LED, red LED, infrared (IR) LED, blue LED, or a yellow LED. Different LEDs with different wavelengths can be used to reach different penetration depths in the skin and, therefore, different blood vessels and tissue. Different LEDs can be chosen according to the location of the body where the PPG signal is recorded and the skin tone of the user. When more than one light emitter is integrated, the plurality of light emitters can include emitters with the same or different wavelengths. For example, a combination of one or more green LEDs, red LEDs and IR LEDs may be integrated. With respect to the photodetectors, one or multiple suitable photodetectors may be employed. Exemplary photodetectors may comprise a semiconductor, optical detectors, image pixels, etc. Any number of light emitters and photodetectors can be provided on the bottom surface of the PCB 224 in the sensor system 240. For example, the electronic device may include a plurality of light emitters and a single photodetector. The light emitters and photodetectors may also be arranged in any suitable configuration on the bottom surface of the PCB 224. For example, they can be symmetrically or asymmetrically arranged within the sensor system 240. As depicted in FIG. 2, one embodiment of the sensor system 240 has an alternating cluster of LEDs and cluster of photodiode sensors arranged in a circle (each cluster is depicted as a rectangle); each cluster of LEDs includes green, red and infrared LEDs. Integrated in the center of the sensor system 240 are two clusters of infrared LEDs (each is depicted as a rectangle); there could be different LED clusters in the center (for example, a cluster of infrared LEDs and a cluster of red LEDs). This arrangement of light emitters and photodetectors in sensor system 240 can introduce redundancy and minimize effects of noise attributed to the skin of the user moving, the light intensity in the ambient environment changing suddenly, and so on. The microcontroller of the electronics module 102 can control the rate by which the LEDs flash per second (e.g., in order to calculate heart rate), and can compensate for low signal levels by increasing LED brightness and sampling rate. Skin absorption rates usually vary when the skin is illuminated by different wavelengths. In some cases, melanin in human skin highly attenuates incident light with relevant wavelength illuminations for the PPG signal recording. In order to correct PPG signal attenuation, the emitters and photodetector can be used to perform an auto-intensity calibration. Therefore, when a raw signal from any illumination channel is either smaller than the lower PPG sensor threshold or larger than the upper threshold, an optimal adaptation of illumination current is implemented by the emitters. In an alternative embodiment, an additional imaging sensor could be integrated to capture the skin tone of the user, which can be used to calibrate the PPG emitters. As depicted in FIG. 2, the non-contact sensors 240 are arranged to be used with a circular sensor window, however that need not always be the case. In some cases, the non-contact sensors 240 can be arranged to be used with a sensor window of another shape (e.g., square, rectangle, oval, polygon, or the like). The shape of the sensor window can be determined by the disposition of the non-contact sensors 240 on the PCB 224, although that need not always be the case. Depending on the type of non-contact sensors 240 in use, the sensor window can be translucent or transparent to specific sensing wavelengths used by the non-contact sensors 240 to provide clear access to the surface of the skin of the user. Examples of suitable non-contact sensors 240 can include, without limitation, optical sensors, imaging sensors (e.g., charge-coupled device (CCD), active-pixel sensor (CMOS), etc), thermal imaging sensors, laser sensors, ultrasonic Doppler flow meters, electromagnetic flow meters, millimeter wave (mmWave) sensors (e.g., 60-64 GHz or 76-81 GHz mmWave radar), and/or other sensors.

In some cases, light-emitting diodes (LEDs) 242 or other light sources can be located on the PCB 224, so the emitted light is made visible on the exterior of the electronics module 102 and smart patch. The LEDs 242 can be used to signal information to a user or for other purposes. In some cases, it can be advantageous to have the LEDs 242 direct light out one side of the PCB 224, such as the left side as viewed in FIG. 1. As used herein, directing light out of a side of the PCB 224 can be considered directing light generally in a direction that is parallel to a plane formed by a top or bottom surface of the PCB 224 and in a direction that is generally away from a centerline or center point of the PCB 224. Such LEDs 242 can be placed on a top or bottom surface of the PCB 224, or optionally on an edge surface (e.g., lateral surface) of the PCB 224. In some cases, LEDs 242 can be oriented to direct light out one side of the PCB 224, although in some cases one or more light piping devices can be used to direct light from LEDs 242 out one side of the PCB 224. Any number of LEDs 242 can be used, and of any suitable color. In some cases, LEDs 242 include a pair of green and red LEDs. LEDs 242 can be controlled to illuminate (e.g., flash or steadily illuminate) to indicate various status information about the electronics module, such as power status, battery life, wireless connectivity, sensor placement, and the like. In some cases, the LEDs 242 can be positioned on the PCB 224 such that light is directed towards a user's face when the electronic module is in use on the user's skin. In such an example, the PCB 224 of FIG. 2 would be oriented such that the left side (e.g., left as seen in FIG. 2) faces up towards the user's face when the smart patch is being used on the user's chest. In some cases, LEDs 242 can be used to signal that one, some, and/or all sensors of the electronics module are capturing data (e.g., cardiopulmonary sounds and/or other physiological signals) properly. In some cases, LEDs 242 can be used to indicate that the ACMs 232, 234, 236 are capturing cardiac sounds (e.g., heart sounds), pulmonary sounds (e.g., lung sounds), or both.

Figure 3:
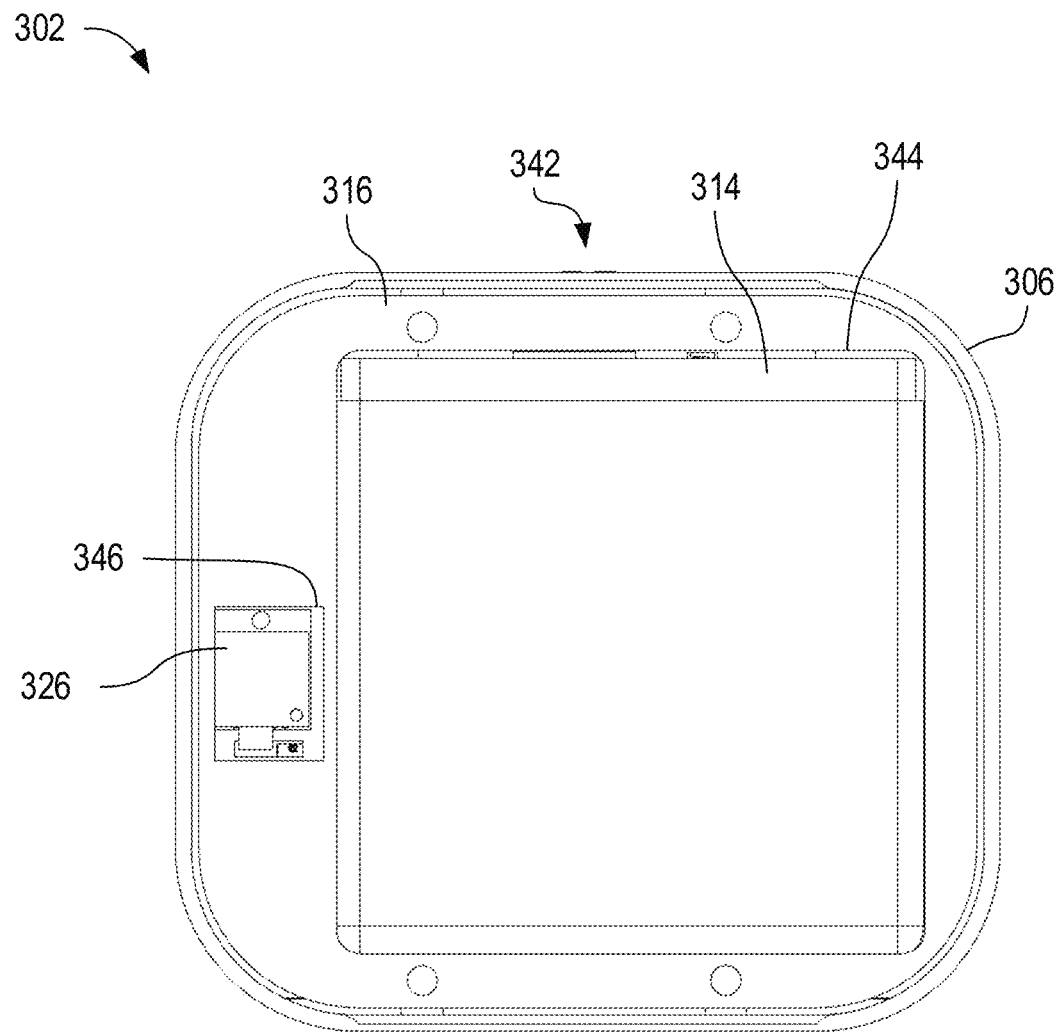
FIG. 3 is a top view of a portion of an electronics module usable in a smart patch, depicting a divider, according to certain aspects of the present disclosure.

FIG. 3 is a top view of a portion of an electronics module 302 usable in a smart patch, depicting a divider 316, according to certain aspects of the present disclosure. Electronics module 302 can be electronics module 102 of FIG. 1. Electronics module 302 and divider 316 can be electronics module 102 and divider 116 of FIG. 1, respectively. The divider 316 can include a receiving space 344 for a battery 314 or other power source. The receiving space 344 can be insulated (e.g., thermally insulated). The divider 316 can also include a receiving space 346 for a discrete wireless module 326. The battery 314 and the wireless module 326 are depicted inside their respective receiving spaces 344, 346 of the divider 316. The wireless module 326 connects to the PCB through an opening in the divider 316 (e.g., an opening in the receiving space 346), such as via a thin flex cable. Similarly, the battery 314 connects to the PCB through an opening in the divider 316 (e.g., an opening in the receiving space 344), such as via a flexible cable.

The wireless module 326 can include an antenna, although that need not always be the case. In some cases, the wireless module 326 can separately couple to an antenna, such as an antenna printed on the main PCB of the electronics module 302 or an antenna located elsewhere (e.g., opposite the divider 316 from the main PCB, such as in an additional receiving space of the divider 316). The wireless module can include one or more antennas for Near Field Communication (NFC), WiFi, Bluetooth (e.g., Bluetooth Low Energy (BLE)), mobile network, and the like. A discrete antenna design can reduce system and assembly cost and time, and can enhance receiver efficiency. The battery 314 and wireless module 326 can be insulated (e.g., by divider 316 or by supplemental insulating material) and separated (e.g., spaced apart from one another). The divider 316 can allow the radio frequency from the battery 314 and antenna module 326 to be blocked from the PCB and the user. The divider 316 can be coupled to the bottom portion 306 of the electronics module 302 through PCB alignment holes (e.g., alignment holes 228 of FIG. 2) using mounting screws or other fasteners. In some cases, the divider 316 can be otherwise secured to the bottom portion 306. In some cases where the enclosure of the electronics module 302 is semi-rigid, the divider 316 can be flexible, as can the PCB and the battery 314. Both the PCB and divider 316 can be assembled in a stacked arrangement, allowing the electronics module 302 to utilize the space within the enclosed chamber more efficiently. The stacked design of components inside the module's enclosure enables the electronics module 302 to have a more compact design compared to other wearable health devices.

The battery 314 can be a thin, rechargeable battery, such as a high capacity lithium polymer (LiPo) battery. Other types of batteries and power sources can be used. The battery 314 can be a high-capacity battery, such as one with sufficient power to allow the various integrated sensors to continually capture data while the device remains wirelessly connected to a smartphone, cloud server, or other computing device to transmit the processed patch data thereto.

In some cases, the battery 314 can be replaceable, although that need not always be the case. In some cases, the battery 314 can be recharged without being removed from the electronics module. In some cases, the battery 314 can be recharged through the electrode contacts on the bottom of the electronics module, such as in response to placing the electronics module 302 on an accompanying charger dock, as disclosed in further detail herein. The battery 314 can also be charged by magnetic and/or other wireless charging technologies, such as magnetic induction charging protocols like Qi charging and NFC charging. For example, the electronics module can include an NFC module and an antenna, which can be used to enable wireless data transfer, over-the-air programming, and charging. The antenna for the NFC module can be integrated into the wireless module 326. Likewise, an induction coil can be positioned inside the electronics module 302 at a desirable location, such as between the divider 316 and the top cover (e.g., for charging through the top cover) or between the PCB and the bottom cover 306 (e.g., for charging through the bottom cover 306). Other techniques for wireless charging can be used.

NFC technology allows the transfer of power to an NFC tag to enable communication by providing a constant carrier signal. This NFC specification uses the 13.56 MHz base frequency and leverages the NFC communication link to control the power transfer. The supported NFC Forum's Wireless Charging (WLC) technical specification extends this communication functionality of NFC technology to enable wireless charging between two NFC-enabled devices in either static or negotiated modes. The static mode uses standard radio frequency (RF) field strength and provides a consistent power level. Negotiated mode uses a higher RF field supporting four power transfer classes of 250, 500, 750 and 1000 milliwatts. When an NFC module is used, the NFC module can be an on-board NFC module integrated into the electronics module 302, and can support different modes of wireless communication to facilitate charging the battery by any compatible device (e.g., an NFC-enabled smartphone, charger, or other electronic device in close proximity).

In some cases, the battery 314 can be recharged using over-the-air wireless charging technology. Over-the-air wireless charging makes use of an external transmitter to wirelessly transfer energy over-the-air to a receiver integrated in the electronics module 302 (e.g., integrated into the PCB). For example, a transmitter operating on a certain frequency (e.g., 2.4 GHz) can interface with an integrated receiver in the PCB or in the wireless communication module connected to the PCB to wirelessly charge the battery 314 when the electronics module 302 is within a given distance (e.g., one meter) of the transmitter device. This functionality would allow for automatic and continuous charging of the electronics module 302 in certain environments (e.g., hospitals, clinics, etc) without its removal from the flexible patch.

Figure 4:
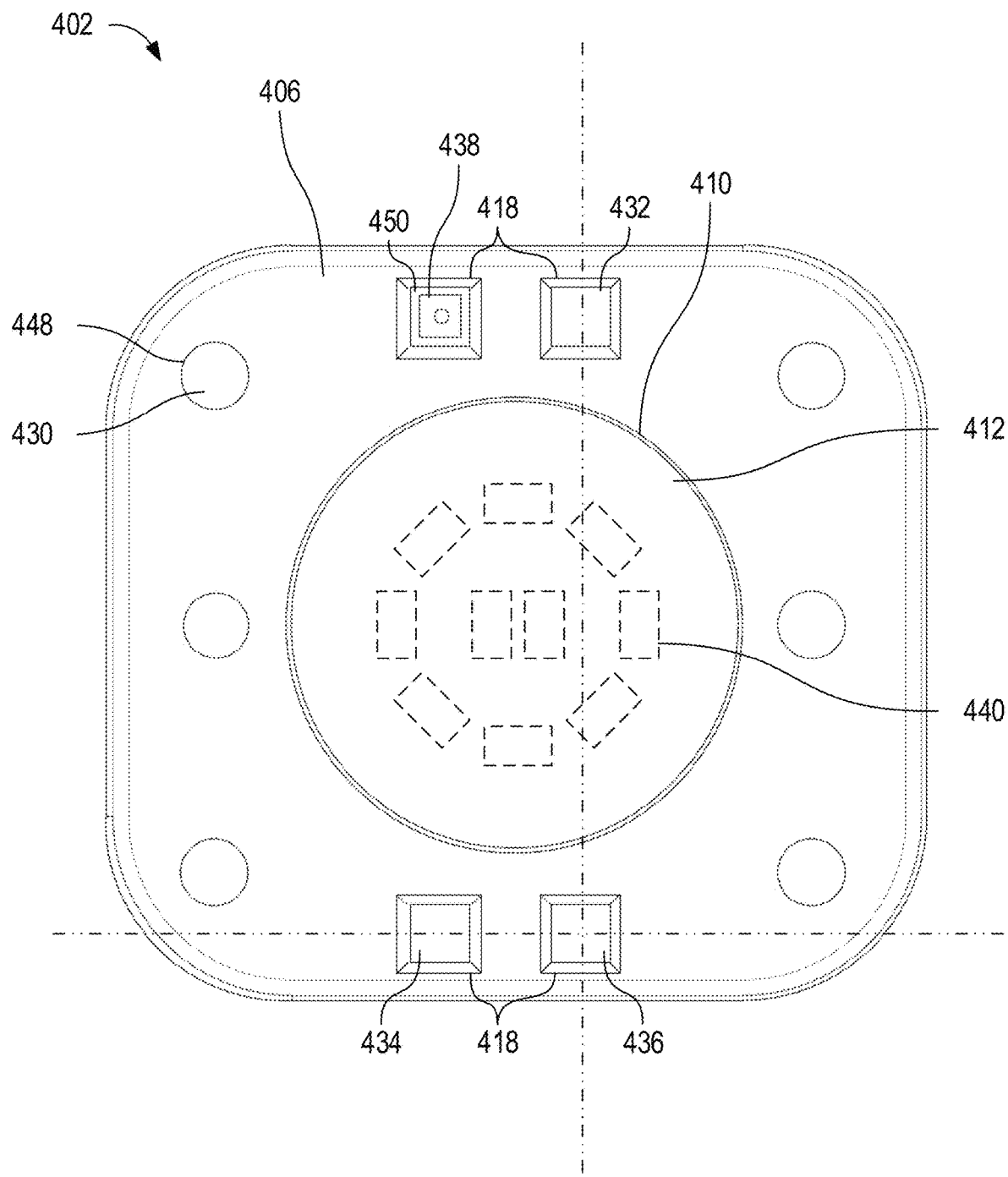
FIG. 4 is a bottom view of a bottom part of an electronics module usable in a smart patch, according to certain aspects of the present disclosure.

FIG. 4 is a bottom view of a bottom part 406 of an electronics module 402 usable in a smart patch, according to certain aspects of the present disclosure. Electronics module 402 can be electronics module 102 of FIG. 1. The bottom part 406 includes a sensor window opening 410 (e.g., for non-contact sensors 440 protected by the sensor window 412), sensor openings 418 (e.g., for various exterior sensors, such as ACM units 432, 434, 436 and a temperature/humidity sensor 438), and electrode openings 448 (e.g., permitting electrode contacts 430 of the PCB to protrude from the bottom exterior surface of the electronics module 402 and make contact with electrode pads of the flexible patch).

The exterior sensors (e.g., ACM units 432, 434, 436 and temperature/humidity sensor 438) and electrode contacts 430 integrate with the bottom of the PCB within the electronics module 402, and extend out from the bottom of the enclosure through the sensor openings 418 and electrode openings 448, respectively. As used herein, the term exterior sensors refers to sensors that are exposed through the bottom portion 406 of the electronics module 402, such as contacting sensors. When the electronics module 402 is received by the receptacle of the flexible patch, the protruding electrode contacts 430 make contact with receiving electrodes of the receptacle of the flexible patch, permitting electrical signals to be passed between the user's skin and the electronics module 402 via the flexible patch. Likewise, when the electronics module 402 is received by the receptacle of the flexible patch, the protruding exterior sensors make contact with the skin of the user or are placed in close proximity to the skin of the user, permitting physiological measurements to be collected from the user's body.

In some cases, a temperature/humidity sensor 438 can protrude through and/or be located at a sensor opening 418 (e.g., the top left sensor opening 418 as depicted in FIG. 4). Once the electronics module 402 is attached to the chest of a user (via the flexible patch), the temperature/humidity sensor 438 can provide skin temperature and humidity readings. To improve accuracy of the skin temperature and humidity readings, an insulation wall 450 can be placed to surround the temperature/humidity sensor 438. Thus, heat transfer from heat sources within the housing to the temperature/humidity sensor 438 can be minimized or reduced. The insulation wall 450 can take any suitable shape, with any number of sides and length of the walls. In some cases, the insulation wall 450 also maximizes the temperature/humidity sensor's 438 exposure to the environment (e.g., the skin of the user). In some cases, a hydrophobic membrane is used over the insulation wall 450 to provide direct contact with the chest area. The hydrophobic membrane can protect the temperature/humidity sensor 438 from contamination from sweat or other particles. The membrane can enclose the insulation walls 450 to facilitate air flow while keeping moisture and contamination out. Thus, when the smart patch is being used, the insulation walls 450 can establish a small, closed environment between the temperature/humidity sensor 438 and the user's skin. In some cases, the insulation wall 450 can be part of the temperature/humidity sensor 438 itself, or can be a separate component.

Adjacent to the temperature/humidity sensor 438 and also at or near the opposite edge of the bottom portion 406 of the electronics module 402, are positioned a first ACM sensor 432, a second ACM sensor 434, and a third ACM sensor 436. The three ACM sensors 432, 434, 436 and the temperature/humidity sensor 438 are disposed in a symmetric matrix with respect to the sensor window 412 as illustrated in FIG. 4, although that need not always be the case. In such cases, three ACM sensors 432, 434, 436 are placed in known positions with respect to one another (e.g., known distances between one another) and to the electronics module (e.g., protruding distance of the ACM sensors from the bottom of the electronics module) to enable triangulation of lungs and/or heart sound signals, thus facilitating the estimation of the location of the sound's origin. The distance between the ACM sensors 432, 434, 436 is correlated with the sampling frequency of the cardiopulmonary sounds. Thus, for a given desired sampling frequency, a smart patch can be constructed with the ACM sensors 432, 434, 436 at appropriate distances from one another. The implemented sampling rate of an ACM sensor 432, 434, 436 will be higher for the shorter distance between ACM units 432, 434, 436. In some cases, multiple ACM sensors 432, 434, 436 are also used to average the synchronized signals and improve the signal-to-noise ratio. The use of the presented auscultation sensors in a location where heart and lung sounds can be acquired would facilitate the remote clinical evaluation of cardiovascular and pulmonary conditions.

The auscultation data captured via the ACM sensors 432, 434, 436 can be synchronized with other physiological metrics captured via other sensors (e.g., temperature/humidity sensor 438, IMU sensors, optical sensors, ECG sensors, and/or bioimpedance sensors), providing clinicians with the ability to correlate, for example, cardiopulmonary sounds to the daily activities of the smart patch user.

In the center of the bottom portion 406 of the electronics module 402, the sensor window 412 allows non-contact sensors 440 within the device to perform optical measurements of the skin of the user. With a maximum air gap (e.g., at or approximately 0.4 mm), the edge of the photoplethysmography (PPG) and other non-contact sensors 440 enclosed in the electronics module 402 are in close proximity to the inner surface of the sensor window 412. In some cases, the external surface (e.g., lower surface, or the surface facing out of the page in FIG. 4) of the sensor window 412 is in direct contact with the skin of a user. In such cases, the small distance between the non-contact sensors 440 and the internal surface (e.g., upper surface, or the surface facing into the page in FIG. 4) of the sensor window 412 allows the sensors to be in very close proximity with the user's skin.

To achieve efficient triangulation of cardiopulmonary sounds, the ACM sensors 432, 434, 436 can be positioned in an array. In some cases, at least three ACM sensors 432, 434, 436 are used, although other numbers of sensors can be used. Each of the ACM sensors 432, 434, 436 can be in a planar array (e.g., a two-dimensional array in which ACM sensors 432, 434, 436 all lie in a common plane). Each of the ACM sensors 432, 434, 436 can include a sensing surface (e.g., the surface facing out of the page in FIG. 4), also known as a contacting surface, that comes into contact with the user's skin during measurement. These sensing surfaces can be coplanar or approximately coplanar to ensure each of the sensing surfaces contacts the user's skin suitably during measurement. The array can include a first ACM sensor 432 and second ACM sensor 436 positioned non-linearly with respect to a third ACM sensor 434. In other words, a line extending through the first ACM sensor 432 and the second ACM sensor 436 can intersect a line extending through the second ACM sensor 436 and the third ACM sensor 434. These lines can intersect at any non-0° or non-180° angle, such as at a 90° angle. When intersecting at a 90° angle, the array can be considered a right triangle array. In some cases, the distance between the first ACM sensor 432 and the second ACM sensor 436 can be at or approximately 32 mm and the distance between the second ACM sensor 436 and the third ACM sensor 434 can be at or approximately 7.7 mm. Other distances can be used, such as distances within 0.1, 0.2, 0.5, 0.75, 1, 1.25, 1.5, 1.75, 2, 2.5, 3, 3.5, 4, 4.5, 5, 5.5, 6, 6.5, or 7 mm of the given distances. In some cases, the distance between the various ACM sensors 432, 434, 436 can be established for a given desired sampling rate. At higher sampling rates, less distance may be needed between adjacent sensors.

Figure 5:
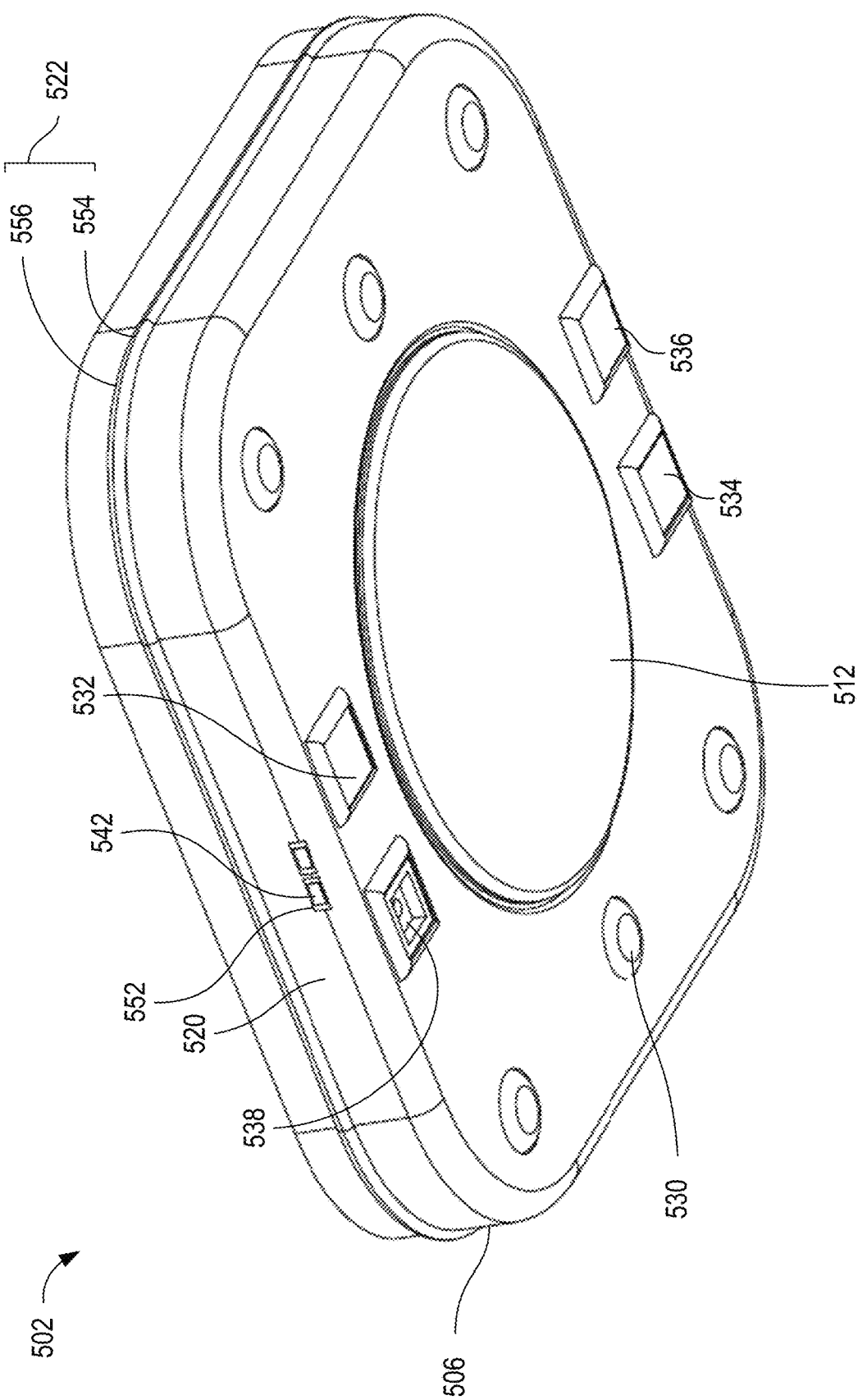
FIG. 5 is a graphical projection of a bottom of an electronics module usable in a smart patch, according to certain aspects of the present disclosure.

FIG. 5 is a graphical projection of a bottom of an electronics module 502 usable in a smart patch, according to certain aspects of the present disclosure. Electronics module 502 can be electronics module 102 of FIG. 1. As depicted in FIG. 5, one of the lateral walls 520 of the bottom portion 506 of the electronics module 502 has two lateral windows 552 (e.g., openings) from which two LEDs 542 (e.g., LEDs 242 of FIG. 2) can be seen. These lateral LED windows 552 can be fabricated with a transparent or translucent material that protects the interior of the chamber but allows light emitted by the LEDs 542 to be visible to the user in order to convey device status or other information as discussed earlier. In some cases, instead of an opening, the window 552 can be a translucent portion of the bottom portion 506, thus permitting light emitted by the LEDs 542 to be visible without a break in the lateral wall 520.

The protruding sensor window 512, temperature/humidity sensor 538 and ACM units 532, 534, 536 project at least a minimum distance from the bottom surface of the bottom portion 506 of the electronics module 502. This minimum distance can be at or approximately 3 mm (e.g., 3 mm or within 0.5 mm, 1 mm, 1.5 mm, 2 mm, and/or 2.5 mm of 3 mm). The minimum distance can be based on the depth of the receptacle of the flexible patch. When the electronics module 502 is inserted into the receptacle of the flexible patch, the sensor window 512 and exterior sensors 532, 534, 536, 538 are on the same plane as the bottom surface of the flexible patch (e.g., the adhesive layer), allowing the sensor window 512 and exterior sensors 532, 534, 536, 538 to make contact with the skin in a consistent manner.

The height of the electrode contacts 530 protruding past the bottom surface of the bottom portion 506 of the electronics module 502 can be smaller than the protruding sensor window 512, temperature/humidity sensor 538, and ACM units 532, 534, 536; these structures project slightly further than the contact electrodes 530 to make contact with the user's skin through their respective openings in the receptacle of the flexible patch. By contrast, the electrode contacts 530 need only make contact with electrode pads of the flexible patch.

The interlocking features 522 are seen surrounding the walls 520 of the electronics module 502. These interlocking features 522 facilitate snapping the electronics module 502 into the receptacle of a flexible patch and maintaining the electronics module 502 in the receptacle of the flexible patch during use. These interlocking features 522 can include a lateral rim 554 and adjacent groove 556, although other features can be used. The lateral rim 554 and groove 556 around the perimeter of the walls 520 can mate with corresponding interlocking features (e.g., lip and groove) of the receptacle of the flexible patch. In some cases, the interlocking features 522 can be used to secure the electronics module 502 in another receptacle, such as a receptacle of a charging dock or a storage receptacle (e.g., for transportation or storage).

Figure 6:
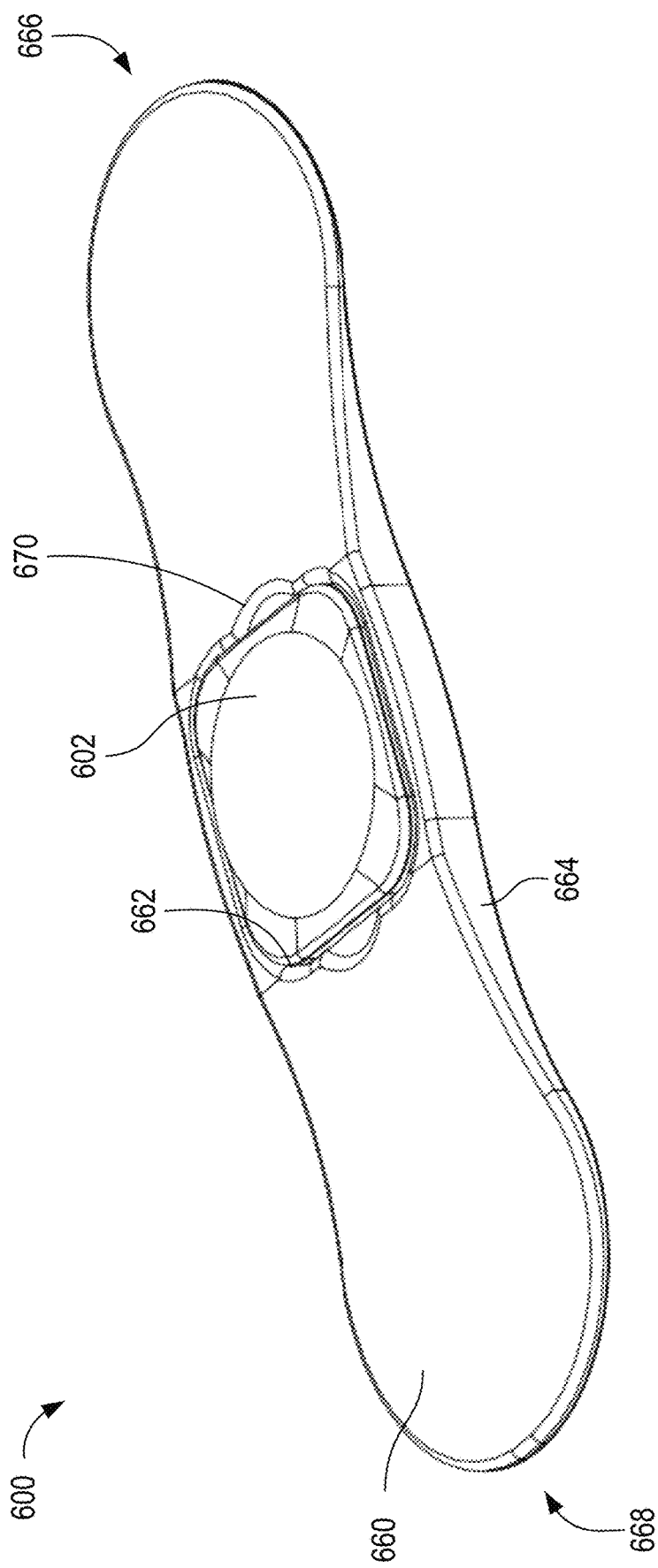
FIG. 6 is a graphical projection of a smart patch, according to certain aspects of the present disclosure.

FIG. 6 is a graphical projection of a smart patch 600, according to certain aspects of the present disclosure. The smart patch 600 can include an electronics module 602 inserted into a receptacle 662 of a flexible patch 660. Electronics module 602 can be electronics module 102 of FIG. 1.

In some cases, when the electronics module 602 is inserted into the receptacle 662, the top of the walls 664 of the flexible patch 660 are flush with the top of the electronics module and there are little or no gaps around the perimeter of the electronics module 602 inside the receptacle 662. When the electronics module 602 is inserted into the receptacle 662, the tight fit can prevent water and/or moisture from entering the receptacle 662 or electronics module 602.

On both lateral sides of the receptacle 662, the height of the wall 664 gradually reduces to the ends 666, 668 of the flexible patch 660 to create a smooth, curved surface that prevents undesired scratching of the user's skin or interference with the user's clothing. The ends 668, 666 and edges of the flexible patch 660 and the electronics module 602 can be rounded for safety and comfort. In some cases, the height of the electronics module 602 is at or less than one centimeter, although other heights can be used (e.g., at or less than 0.5 cm, 0.6 cm, 0.7 cm, 0.8 cm, 0.9 cm, 1 cm, 1.1 cm, 1.2 cm, 1.3 cm, 1.4 cm, 1.5 cm, 1.6 cm, 1.7 cm, 1.8 cm, 1.9 cm, 2 cm, 2.1 cm, 2.2 cm, 2.3 cm, 2.4 cm, and/or 2.5 cm).

The relatively small height of the electronics module 602 facilitates a user discreetly wearing the smart patch 600 beneath their clothing. The material of the flexible patch 660 can include polyamide, thermoplastics, acrylonitrile styrene acrylate (ASA), composites, or other skin friendly materials that provide suitable durability, non-toxicity, flexibility, and water repellent characteristics. The material of the flexible patch 660 and its design can facilitate long-term adhesion to the user without discomfort.

In some cases, the implementation of chemical markers on the adhesive substrate of the patch can enable a smart patch as disclosed herein to be used for the rapid, non-invasive detection and analysis of blood analytes. Besides blood characteristics, the chemical markers in the adhesive substrate could be an alternative for non-invasive detection of alcohol, lactate (e.g., in sport activity), or urea (e.g., for kidney patients), among other substances.

The top of the flexible patch 660 can include a recess 670 on one or both lateral sides of the receptacle 662 to facilitate easy gripping and removal of the electronics module 602. Each recessed area 670 is sized to allow a human thumb and/or finger to be used to extract the electronics module 602 from the receptacle 662. The recesses 670 are not deep enough to retain liquid or particles that may damage the electronics module 602. The recesses 670 allow for the easy removal of the electronics module 602 from the flexible patch 660, such as to swap the electronics module 602 for a different electronics module, to perform troubleshooting on the electronics module 602 without having to remove the flexible patch 660 from the user's skin, to change the flexible patch 660 for a new location, or to recharge the electronics module 602.

While the electronics module 602 is depicted as part of a smart patch 600 in FIG. 6, in some cases, the electronics module 602 can be used in other fashions. In an example, electronics module 602 can be used alone or inserted into a different receptacle for the purpose of wireless auscultation. In such an example, the electronics module 602 can be temporarily placed on the skin of the user at different locations to detect sounds from different parts of the user's body. In some cases, the electronics module 602 can be slid along the surface of the skin of the user. In some cases, the electronics module 602 may include fewer sensors and/or electrode contacts, such as including three ACMs without any temperature/humidity sensor, without sensor windows and associated sensors, and/or without electrode contacts.

Figure 7:
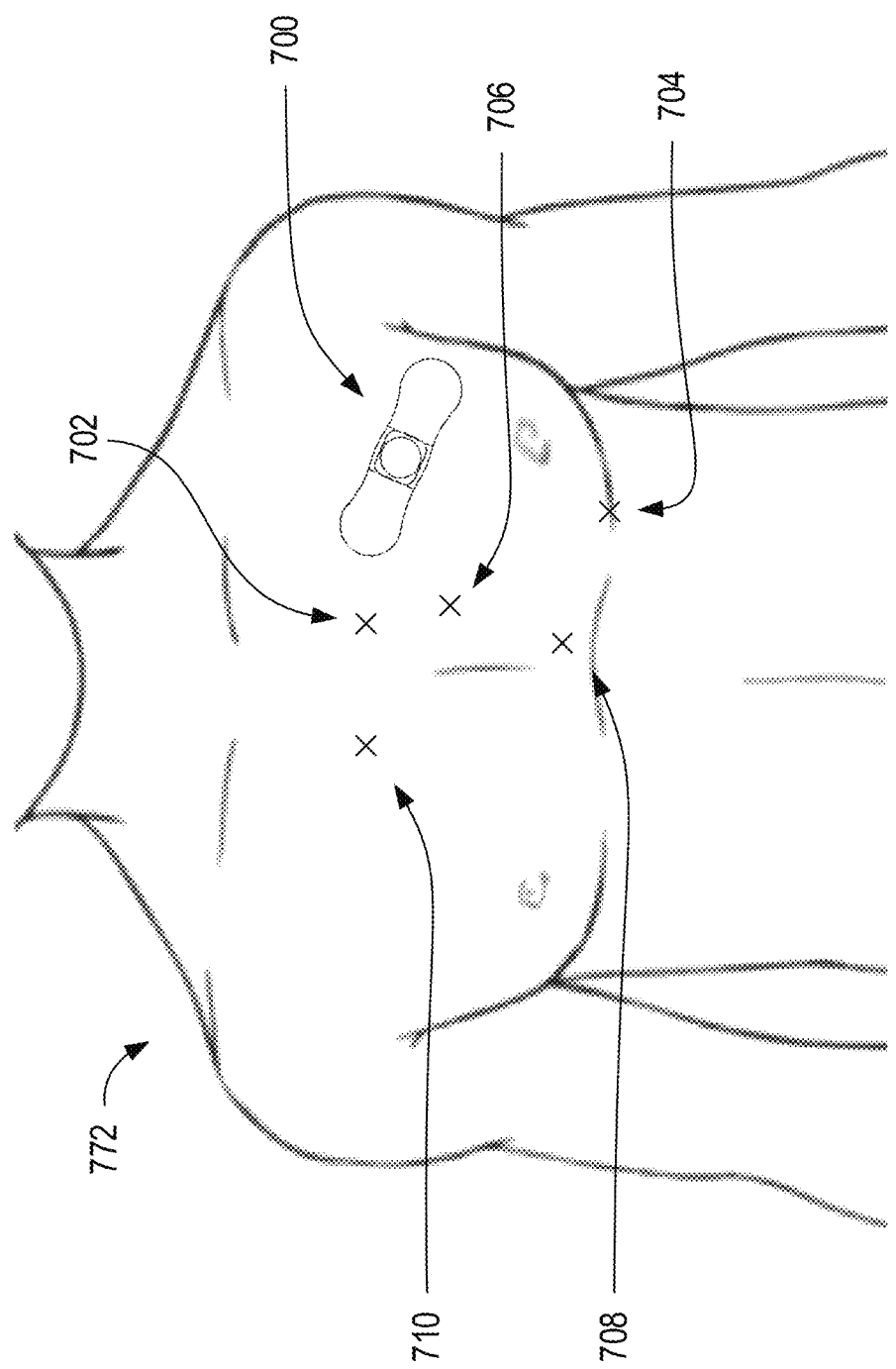
FIG. 7 is a front partial view of the torso of a user wearing a smart patch, according to certain aspects of the present disclosure.

FIG. 7 is a front partial view of a user 772 wearing a smart patch 700, according to certain aspects of the present disclosure. The smart patch 700 can be smart patch 600 of FIG. 6. The smart patch 700 is shown attached to the chest of the user 772 in proximity to the heart. The smart patch 700 is shaped to fit comfortably and the flexible adhesive structure of the smart patch 700 conforms to the contours of the chest of the user 772. The electronic module's LEDs can be seen by the user 772 when worn, such as from above the smart patch 700. The LEDs are positioned on the side of the smart patch 700 facing towards the top of FIG. 7, such that the user 772 can tilt their head down to see any light emanating from one or both LEDs.

The position of the smart patch 700 on the user's chest in FIG. 7 can be a useful location, especially for the purposes of obtaining heart sounds and lung sounds. Other useful locations include the left 2nd intercostal space 702 and the left 5th intercostal space 704. Other useful locations include the left 3rd intercostal space 706, the left 4th intercostal space 708, and the right 2nd intercostal space 710. Other locations can also be used, such as locations on the skin over the location of a lung of the user.

In some cases, the smart patch 700 can provide feedback (e.g., directly from the smart patch 700, such as from an LED, or via another device, such as a connected smartphone) regarding whether or not the smart patch 700 is located in a suitable location and/or suitable place on the skin. In some cases, the positioning of the smart patch 700 can be thus established prior to adhering the smart patch 700 to the skin (e.g., prior to removing the peel-away removable cover layer covering the adhesive layer). Suitability of location can be determined from sensor readings (e.g., quality of sensor readings or estimated locations based on sensor readings). In some cases, the peel-away removable cover layer can include openings for the contact sensors and/or sensor window, to facilitate determining correct placement.

Figure 8:
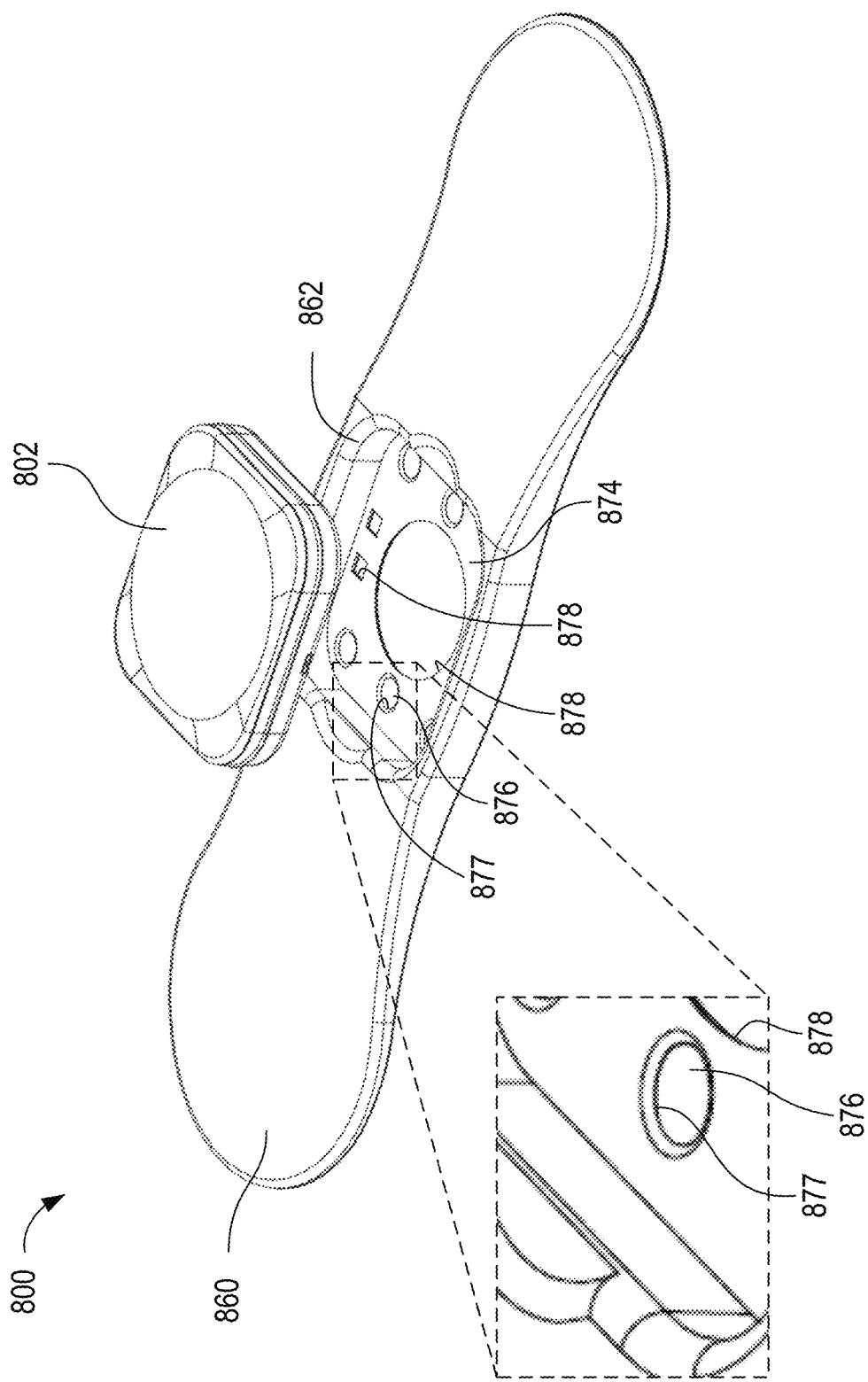
FIG. 8 is a combination of a graphical projected view and a partial enlarged view of a smart patch showing an electronics module being inserted into a receptacle of a flexible patch, according to certain aspects of the present disclosure.

FIG. 8 is a combination of a graphical projected view and a partial enlarged view of a smart patch 800 showing an electronics module 802 being inserted into a receptacle 862 of a flexible patch 860, according to certain aspects of the present disclosure. The smart patch 800 can be smart patch 600 of FIG. 6. The electronics module 802 can be electronics module 102 of FIG. 1. The lateral lip and groove connections between the electronics module 802 and the receptacle 862 allow the electronics module 802 to be securely coupled or detached from the receptacle 862 as needed. In some cases, placement of the electronics module 802 into the receptacle 862 creates a moisture-resistant seal around the top and the bottom of the smart patch 800, which enables the smart patch 800 to be worn at all times, even during bathing or other activities that could expose the electronics module 802 to moisture.

On the bottom surface 874 of the receptacle 862, there is an opening 878 for the sensor window and openings 879 for other sensors, such as the temperature/humidity sensor and the three ACM units. The opening 878 is aligned with the sensor window and each of the openings 879 is aligned with its respective sensor (e.g., the temperature/humidity sensor and the three ACM units protruding from the bottom of the electronics module) such that these components may come in contact with the skin of the user to capture physiological data.

When the electronics module 802 is securely received into the receptacle 862 (e.g., snapped into place), the electrode contacts of the electronics module 802 contact electrode pads 876 of the flexible patch 860. Recesses 877 in the receptacle 862 can permit electrode contacts of the electronics module 802 to make contact with electrode pads 876. In some cases, instead of using recesses 877, the electrode pads 876 can be directly incorporated onto a surface of the receptacle 862. The electrode pads 876 are electrically coupled (e.g., via flexible circuit traces) to respective electrode pads (e.g., ECG electrodes and bioimpedance electrodes) on the bottom of the flexible patch 860 that contact the user's skin when the smart patch 800 is used. In some cases, the electrode pads on the bottom of the flexible patch 860 can be hydrogel electrodes. ECG and bioimpedance signals, which originate at the hydrogel electrode-skin interface, can be conducted to the electronics module 802 via the electrode pads 876. In some cases, the electrode pads 876 can be dry, semi-dry, or hydrogel electrode pads.

Figure 9:
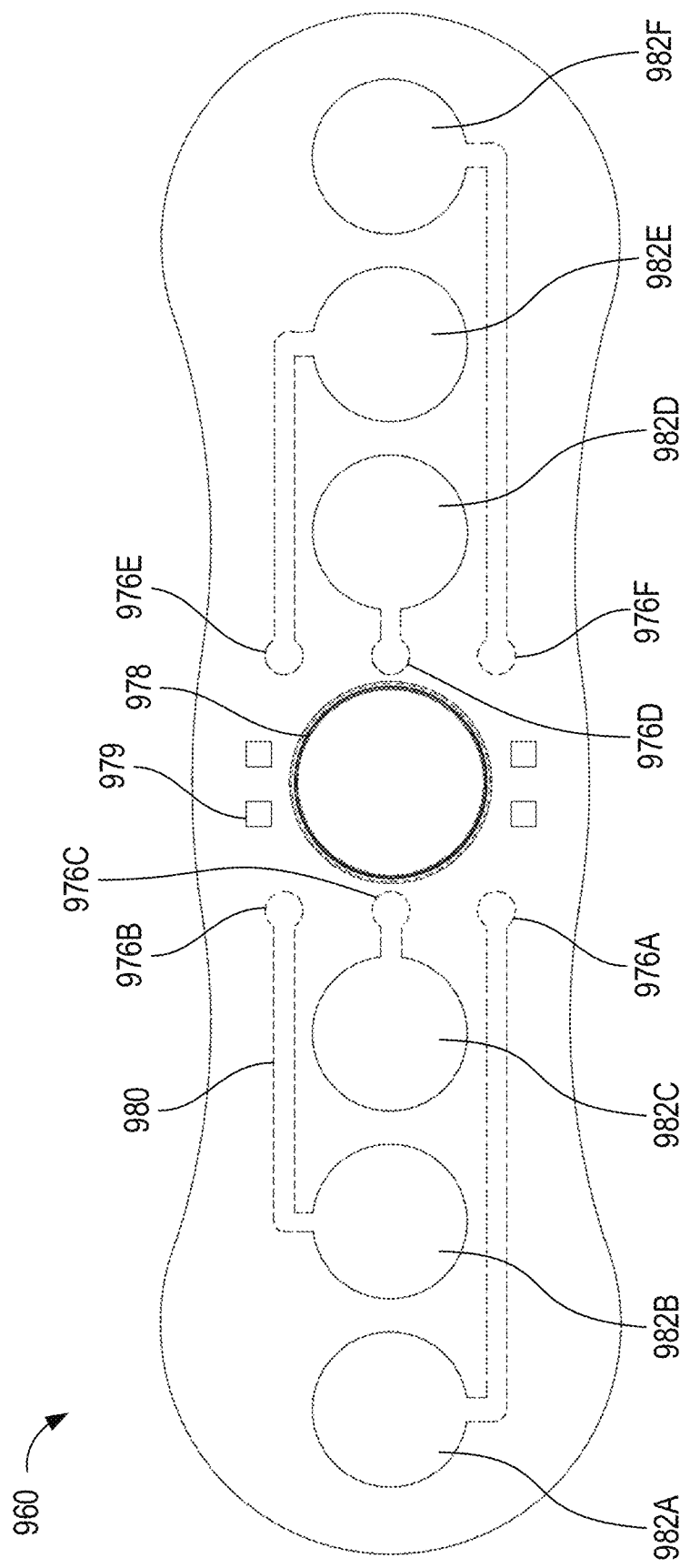
FIG. 9 is a bottom view of a bottom surface of a flexible patch, according to certain aspects of the present disclosure.

FIG. 9 is a bottom view of a bottom surface of a flexible patch 960, according to certain aspects of the present disclosure. The flexible patch 960 can be any suitable flexible patch portion of a smart patch, such as flexible patch 660 of FIG. 6. For illustrative purposes, the electrode pads 976A-

976F and flexible traces 980 are depicted in dashed lines. While described as flexible traces in FIG. 9, flexible traces 980 can include any suitable flexible conductor. As depicted in FIG. 9, the flexible patch 960 can include six electrode pads 982A-982F, although any suitable number of electrodes can be used and implemented in different configurations (e.g., size, arrangements, distance, chest position, and the like) for enhanced physiological sensing (e.g., multiple lead ECG measurements). Each of the electrode pads 982A-982F can be a hydrogel electrode (e.g., an electrode covered with a conductive hydrogel coating, preferably an adhesive hydrogel coating). Pairs of electrode pads 982A-982F can be used for different functions. For example, electrode pads 982A and 982F can be a first pair that is used to detect ECG signals; electrode pads 982B and 982E can be a second pair that is used to supply a current to the user for bioimpedance analysis; and electrode pads 982C and 982D can be a third pair that is used to detect a voltage associated with the current supplied by the second pair for the purpose of bioimpedance analysis. This particular arrangement can be especially useful for achieving accurate results in a small form factor, although other numbers of electrode pairs and arrangements of electrode pairs can be used.

Each of the electrode pads 982A-982F can couple to a respective electrode pad 976A-976F via a circuit trace 980. In some cases, the electrode pads 976A-976F can be arranged according to respective electrode pairs. For example, for the first electrode pair (e.g., electrodes 982A, 982F), the respective electrode pads 976A, 976F can be located adjacent to a first side (e.g., a side nearest the bottom of FIG. 9) of the flexible patch 960; for the second electrode pair (e.g., electrodes 982B, 982E), the respective electrode pads 976B, 976E can be located adjacent to a second side (e.g., a side nearest the top of FIG. 9) of the flexible patch 960; and for the third electrode pair (e.g., electrodes 982C, 982D), the respective electrode pads 976C, 976D can be located at or near the center or a centerline of the flexible patch 960.

Both types of electrodes (e.g., ECG and bioimpedance) can be aligned on the bottom surface of the flexible patch 960. In some cases, the electrode pads 982A-982F in the adhesive substrate of the flexible patch 960 are positioned perpendicularly to the axis of symmetry defined by the electrode pads 976A-976F.

In some cases, a flexible patch 960 can make use of fewer electrodes (e.g., four electrodes instead of six electrodes 982A-982F). In such cases, ECG and bioimpedance measurements can still be collected by sharing one or both pairs of electrodes for ECG and bioimpedance measurements. This sharing of electrodes can be achieved by temporally controlling the measurements of each (e.g., via a microcontroller) or by filtering and processing the acquired signals.

In some cases, additional external electrodes can be used in conjunction with the electrodes 982A-982F of the flexible patch 960. In such cases, one or more additional external electrodes can couple to an electronics module (e.g., electronics module 102 of FIG. 1) via any suitable type of flexible connector (e.g., a cable) that couples to the electronics module via an electrical connector (e.g., a plug, a pin, or any other suitable connector). Thus, while the flexible patch 960 may be attached to a user at a first location, one or more additional external electrodes can be simultaneously attached to the user at other locations spaced apart from the first location. These additional external electrodes can facilitate the acquisition of additional ECG data. For example, with the flexible patch 960 positioned on the user's chest adjacent to the heart, additional external electrodes placed on the lower or upper torso and coupled to the electronics module that is inserted into the flexible patch 960 can facilitate the acquisition of 5-lead ECG measurements, similar to a Holter monitor.

The bottom of the flexible patch 960 can include an opening 978 for the sensor window and openings 979 for other sensors, such as the temperature/humidity sensor and the three ACM units. With an electronics module placed into the receptacle of the flexible patch 960, the opening 978 is aligned with the sensor window of the electronics module and each of the openings 979 is aligned with its respective sensor (e.g., the temperature/humidity sensor and the three ACM units protruding from the bottom of the electronics module) such that these components may come in contact with the skin of the user to capture physiological data.

Figure 10A:
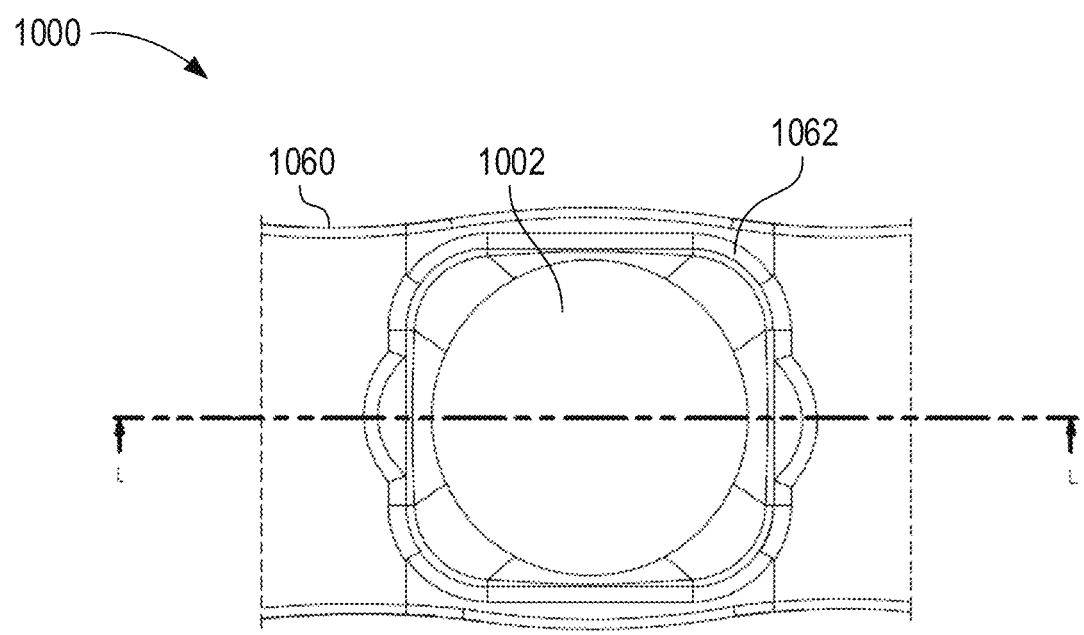
FIG. 10A is a top view of a portion of a smart patch depicting an electronics module secured within a receptacle of a flexible patch, according to certain aspects of the present disclosure.

FIG. 10A is a top view of a portion of a smart patch 1000 depicting an electronics module 1002 secured within a receptacle 1062 of a flexible patch 1060, according to certain aspects of the present disclosure. Smart patch 1000 can be smart patch 600 of FIG. 6. The recesses of the receptacle 1062 facilitate the removal of the electronics module 1002.

Figure 10B:
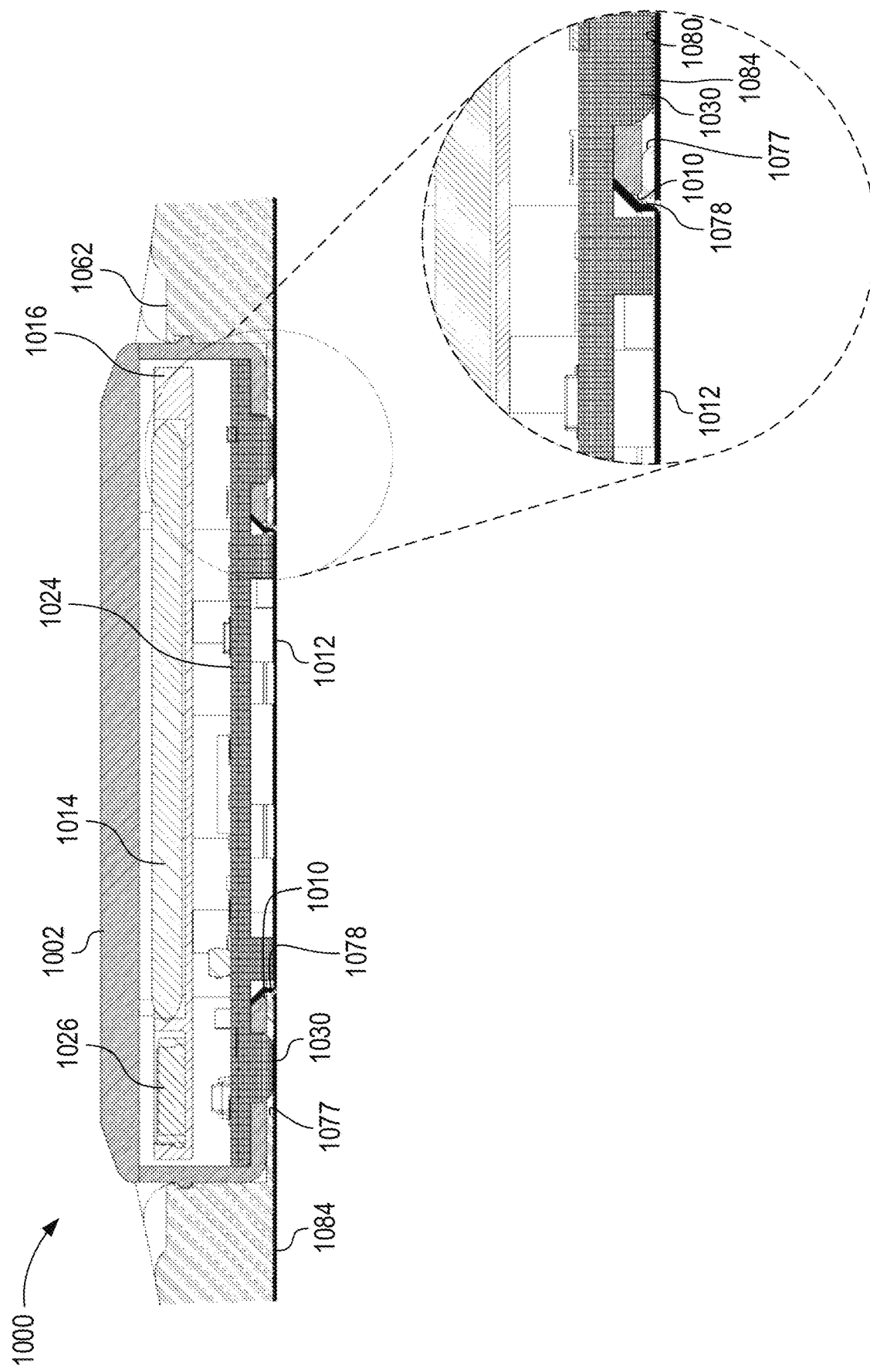
FIG. 10B is a combination cross-sectional view and enlarged cross-sectional view of a portion of a smart patch taken across line L-L of FIG. 10A.

FIG. 10B is a combination of a cross-sectional view and an enlarged partial view of the cross-section portion of smart patch 1000 taken across the cutaway line L-L of FIG. 10A. The inner components of the electronics module 1002, as well as the inside structure of the receptacle 1062 of the flexible patch, can be seen. The position of the divider 1016 containing the battery 1014 and the wireless module 1026 is illustrated. Below the battery 1014 and wireless module 1026 lies the PCB 1024 with the microcontroller unit (MCU), memory units, power management, and other such components on the upper surface of the PCB 1024 (e.g., the surface facing towards the top of FIG. 10B or out of the page in FIG. 10A), and with the sensors and electrode contacts integrated on the bottom surface of the PCB 1024 (e.g., the surface facing towards the bottom of FIG. 10B or into the page in FIG. 10A).

The receptacle 1062 has an opening 1078 at the bottom that is the same size and shape of the electronics module's sensor window 1012. Other openings not visible in this cross-sectional view are available for other sensors, such as the temperature/humidity sensor and ACM units. As depicted in FIG. 10B, the sensor window opening 1010 of the electronics module 1002 can be seen, with the sensor window 1012 positioned therein. When the electronics module 1002 is fully inserted into the receptacle 1062, the bottom of the sensor window 1012 is flush with or approximately flush with the bottom of the electrode pads (e.g., hydrogel surface of the electrode pads that couples to the user's skin) of the flexible patch. Similarly, the temperature/humidity sensor and the three ACM units emerge from the base of the electronics module such that the ends of these sensors (e.g., the ends of the ACM units or the end of the insulation wall of the temperature/humidity sensor) are flush with or approximately flush with the bottom of the electrode pads. Therefore, the electrode pads, the sensor window 1012, the temperature/humidity sensor, and the ACM units can all contact the skin of the user at the same time.

In some cases, the electrode contacts 1030 of the electronics module 1002 pass through or into recesses 1077 in the bottom of the receptacle 1062. In some cases, these electrode contacts 1030 make electrical contact with flexible traces 1080, which couple together the electrode contacts 1030 with the electrode pads of the flexible patch.

The bottom surface of the flexible patch can include an adhesive layer 1084. The adhesive layer can include conductive hydrogel over the electrode pads. The bottom surface of the sensor window 1012, temperature/humidity sensor (e.g., insulation wall), and ACM units can be at or approximately coplanar with the bottom surface of the adhesive layer 1084.

Figure 11:
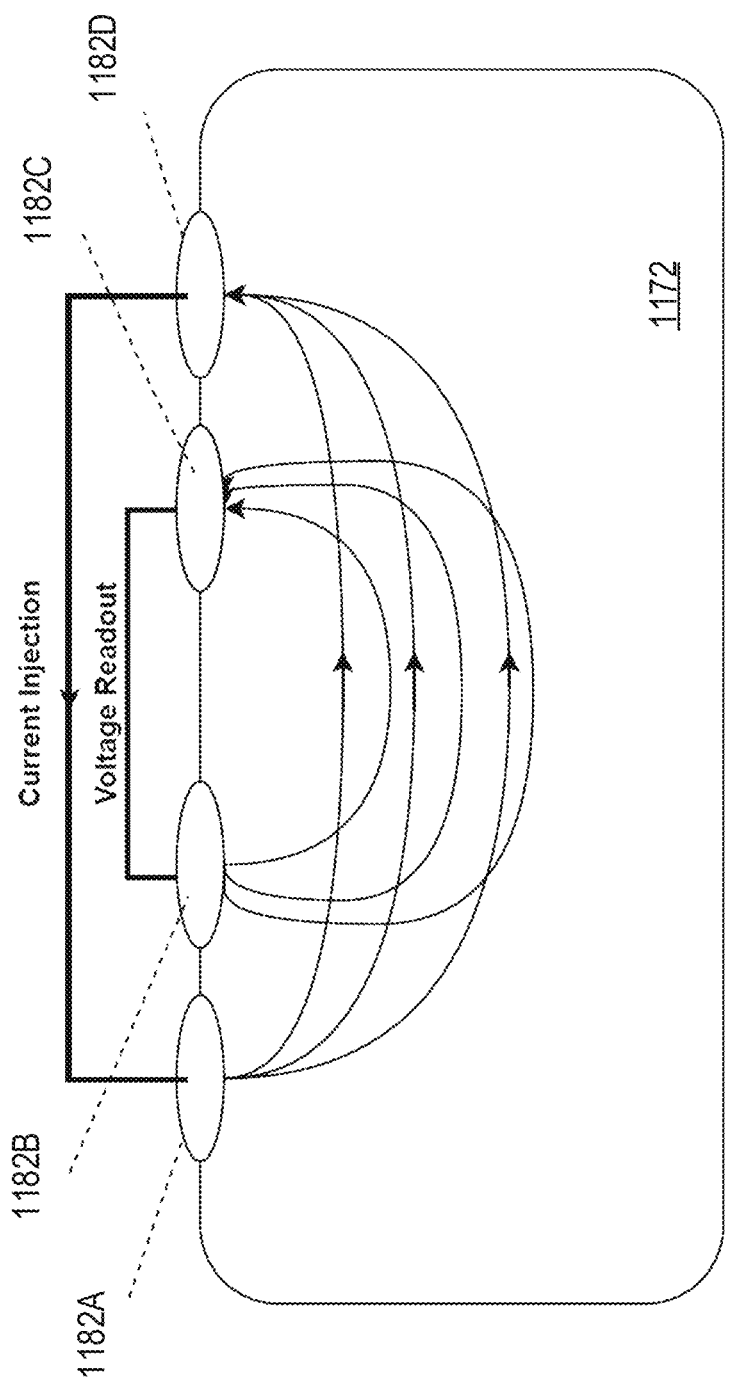
FIG. 11 is a schematic diagram of a set of electrode pads for bioimpedance measurements according to certain aspects of the present disclosure.

FIG. 11 is a schematic diagram of a set of electrode pads 1182A-1182D for bioimpedance measurements according to certain aspects of the present disclosure. Electrodes 1182A-1182D can be used in any suitable smart patch, such as smart patch 600 of FIG. 6. Electrodes 1182A, 1182B, 1182C, 1182D can be any suitable electrodes, such as electrodes 982B, 982C, 982D, 982E of FIG. 9, respectively. The electrodes 1182A-1182D can include at least two pairs of non-adjacent electrodes. Because of their placement with respect to each other, electrodes 1182A, 1182D can be considered external electrodes, at least with respect to electrodes 1182B, 1182C, which can be considered internal electrodes. In some cases, the disclosed technology can be used for non-invasive continuous monitoring of glucose levels for efficient diabetes management without the need for blood sampling.

For measuring bioimpedance, a pair of non-adjacent opposite electrodes (e.g., electrodes 1182A, 1182D) can be configured to inject a current (e.g., a low frequency current) into the tissue 1172 (e.g., skin and underlying tissue) of a wearer, whereas at least another pair of antagonist electrodes (e.g., electrodes 1182B, 1182C) is used to measure voltage from the skin of the user (e.g., generate a voltage readout). The PCB sensor and its bioimpedance circuitry is coupled to at least four electrodes (e.g., electrodes 1182A-1182D) to measure and determine bioimpedance data, such as hydration levels, glucose levels in the blood, or the mass composition of the body of a patient, among other health metrics.

The bioimpedance circuitry can be configured to measure multiple frequencies. In some cases, the electrode circuitry can be configured to measure the impedance signal using at least one low measurement frequency. At least one low measurement frequency may be in the range of at or approximately 5 kHz to at or approximately 15 kHz. In some cases, the external electrodes (e.g., electrodes 1182A, 1182D) are used to inject current into the tissue 1172 of the user's chest area. The electronics module can utilize the MCU in the PCB coupled to the impedance circuitry to determine the tissue impedance measured between the inner electrodes (e.g., electrodes 1182B, 1182C). The processor of the electronics module may be configured to determine the conductive quality of the skin-electrode interface from a second measurement frequency that is different from the first measurement frequency, and may be configured to measure an increase or reduction in the tissue resistance (e.g., with respect to the first measurement frequency). In some cases, a single measurement frequency is used while in other cases multiple measurement frequencies are used to observe frequency dependent changes in the evaluated tissue. Additionally, these observations on the conductive quality of the skin-electrode surface may be used to determine the quality of the measurements.

In some cases, the hydration signal and the electrodermal activity (EDA) can be extracted from the tissue resistance measurement and a tissue reactance measurement. The EDA measurement can make use of an algorithm to take the output of the various recordings and translate this output into a measurement for stress levels. Besides stress levels, the EDA can provide the level of neural response and physical activity, as well as level of moisture (e.g., sweat), among other possible indicators. EDA, also known as galvanic skin response (GSR), sensing for stress measurement may require continuous monitoring of the electrical properties of skin, which can be provided by the durable adherence of a flexible patch as disclosed herein.

Figure 12:
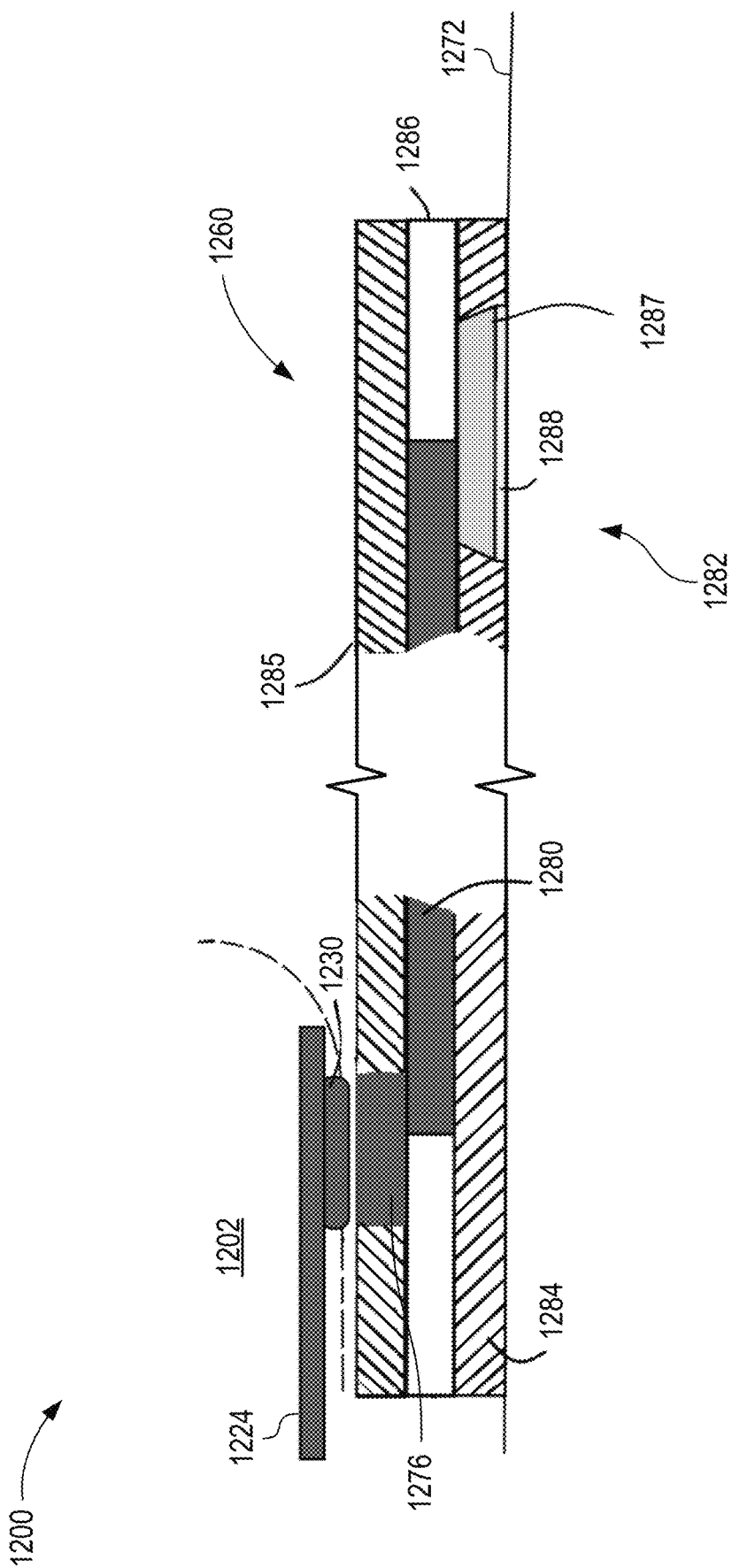
FIG. 12 is a simplified schematic side view of a smart patch, depicting various layers of the flexible patch and electrical connection to the electronics module, according to certain aspects of the present disclosure.

FIG. 12 is a simplified schematic side view of a smart patch 1200, depicting various layers of the flexible patch 1260 and electrical connection to the electronics module 1202, according to certain aspects of the present disclosure. Smart patch 1200 can be any suitable smart patch, such as smart patch 600 of FIG. 6 and electronics module 1202 can be any suitable electronics module, such as electronics module 602 of FIG. 6. The electronics module 1202 is operatively coupled to the flexible patch 1260.

The flexible patch 1260 can include several layers. Extending from the PCB 1224 out to the exterior of the electronics module 1202 are electrode contacts 1230 that mate with (e.g., electrically couple with) corresponding electrode pads 1276 of the flexible patch 1260. The electrode pads 1276 can electrically couple the electrode contacts 1230 of the electronics module 1202 with the electrode pads 1282 that are electrically coupled to the user's skin 1272. In some cases, electrode pads 1282 are electrically coupled to the user's skin 1272 via a conductive hydrogel layer 1287 and optionally a conductive selective layer 1288. This arrangement can be considered a "wet" electrode contact, where the conductive selective layer can be used to improve the potential stability. In some cases, the conductive selective layer can be used for continuous monitoring of the user's physiological biochemical signals. In some cases, however, a "dry" electrode contact can be used. In such a "dry" electrode contact, the electrode pads 1282 can be made of a conductive metal (e.g., Ag or AgCl) that directly contacts the user's skin 1272 (e.g., through openings in one or more layers of the flexible patch 1260). Such a "dry" electrode contact can be made without the use of a hydrogel layer 1287 or an optional conductive selective layer 1288. In other cases, a "semi-dry" electrode contact can be used as electrode pads 1282.

The smart patch 1200 makes use of a flexible patch 1260 that can be mechanically flexible, although that need not always be the case. However, the use of a flexible patch 1260 that is mechanically flexible can facilitate adhesion of the flexible patch 1260 to the user's skin 1272 (e.g., at or around the user's chest) while conforming to the shape of that user's anatomy. Suitable material used to fabricate the conforming structure of the flexible patch 1260 can be selected for sufficient flexibility (e.g., whether by material modulus or structure elasticity), waterproofness, biocompatibility, and/or electrical insulation.

The flexible patch 1260 can include a support layer 1285, which can be made out of any suitable material, such as a flexible foam. The support layer 1285 can provide mechanical support for other layers, as well as electrical insulation. The support layer 1285 can be the uppermost layer (e.g., top layer as viewed in FIG. 12), such as the layer that faces out and away from the user when the smart patch 1200 is being worn. In some cases, one or more additional layers can be provided above the support layer 1285, such as to further seal the smart patch 1200 or for the purpose of applying printing or indicia to the smart patch 1200.

The flexible patch 1260 can couple to a user's skin 1272 through any suitable technique. The flexible patch 1260 can include an adhesive layer 1284, which can be made out of any suitable material, such as a flexible adhesive. The material of the adhesive layer 1284 can be selected to be biocompatible for use on skin. The adhesive layer 1284 can be the lowermost layer (e.g., bottom layer as viewed in FIG. 12), such as the layer that comes into contact with the skin 1272 of the user. The adhesive layer 1284 can be configured to couple to the body of a user, under ambient conditions, for a duration on the order of days, such as at least a week or at least 5, 6, 7, 8, 9, 10, 11, or 12 days. In some cases, the adhesive layer 1284 can be composed of an adhesive, such as a layer of acrylate pressure sensitive adhesive, although other adhesives can be used.

While disclosed herein with reference to an adhesive layer 1284, in some cases, the flexible patch 1260 can be made without an adhesive layer 1284, in which case the flexible patch 1260 can be held in place through other techniques (e.g., external bandages, straps, or other materials that apply a compressive force to push and/or attach the flexible patch 1260 onto the skin 1272 of the user).

The electrode pad 1276 can be coupled to the electrode pad 1282 via a conductive layer 1280 (e.g., a flexible trace). The conductive layer 1280 can be printed on or embedded within an insulation layer 1286 to avoid electrical leakage and to protect the user. The conductive layer 1280 can be made out of any suitable conductive metal such as Ag, Cu, or compounds like AgCl. The conductive layer 1280 can extend between a proximal end where it electrically couples to the electrode pad 1276, and to a distal end where it electrically couples to the electrode pad 1282. At the distal end, a conductive hydrogel layer 1287 can provide electrical conductivity between the skin 1272 and the conductive layer 1280.

The transport speed in a preferable hydrogel of a conductive hydrogel layer 1287 can depend on a number of factors, including hydrogel porosity, iontophoresis current, etc. A preferable hydrogel can remain hydrated, under ambient conditions, for a duration on the order of days, such as at least a week or at least 5, 6, 7, 8, 9, 10, 11, 12, 13, or 14 days. A preferable hydrogel can allow for rapid electrical transport, reducing the time required for signal detection. To increase the precision of the electrode signaling, an optional conductive selective layer 1288 can be coupled to the conductive hydrogel layer 1287 and be placed in contact with the skin 1272 of the user's chest. In some cases, the hydrogel can be optimized to limit biofouling and enhance sensor stability. For example, the conductive selective layer 1288 adjacent to the conductive hydrogel layer 1287 can also incorporate anti-fouling, bactericidal, and/or antifungal chemical agents.

The smart patch 1200 may also include additional treatment capabilities. In some cases, the smart patch 1200 can release medications and/or treatments, such as via the adhesive layer 1284. Such medications and/or treatments can be released automatically over time, can be released automatically at specific time intervals, or can be released dynamically based on changes in the physiological measurements of the user. Various techniques can be used to supply such medications and/or treatments. In one example, medication can be incorporated into the adhesive layer 1284 during manufacture and can be configured to be released into the user transdermally over time. In another example, a medication supply chamber containing medication can be controlled (e.g., via electronics module 1202) to supply medication to the adhesive layer 1284 such that the medication can be released into the user transdermally. Examples of medications and/or treatments that could be released can include insulin, heart medications, antibiotics, diuretics, steroids, and the like.

Figure 13:
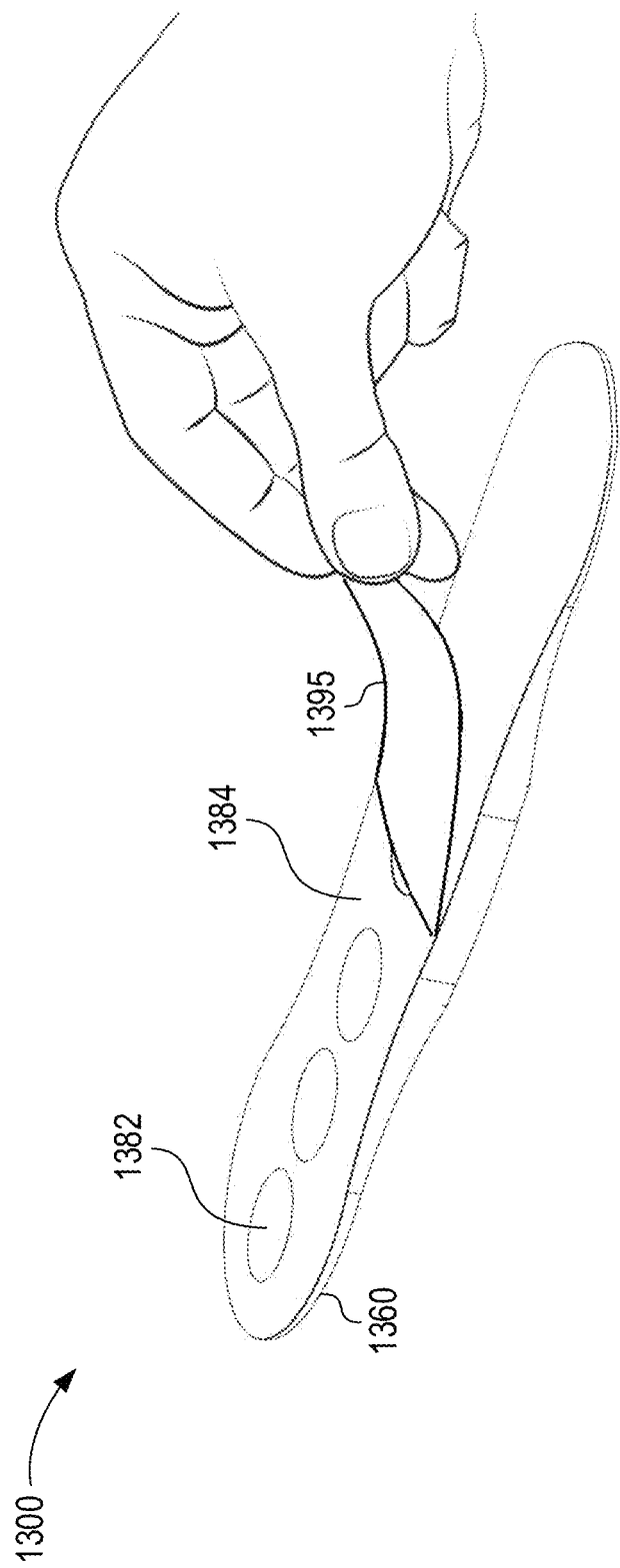
FIG. 13 is a graphical projection of a bottom of a smart patch being prepared for application onto the skin of a user, according to certain aspects of the present disclosure.

FIG. 13 is a graphical projection of a bottom of a smart patch 1300 being prepared for attachment onto the skin of a user, according to certain aspects of the present disclosure. Smart patch 1300 can be any suitable smart patch, such as smart patch 600 of FIG. 6. The smart patch 1300 includes a removable cover layer 1395 to protect the adhesive layer 1384 prior to use. The removable cover layer 1395 can be made of any suitable material for temporarily covering the adhesive layer 1384, preferably without decreasing the ability for the adhesive layer 1384 to stick to the skin of the user. Example materials for the removable cover layer 1395 include paper, plastic, and the like. When affixing the smart patch 1300 to the skin of the user, the removable layer 1395 is peeled off or otherwise removed, exposing the sticky, adhesive layer 1384, as well as the electrode pads 1382. This bottom surface of the smart patch 1300 (e.g., the surface of the smart patch 1300 facing towards the top of FIG. 13) can then be affixed to the skin of the user, thus allowing the adhesive layer 1384 to adhere to the skin of the user and the electrode pads 1382 to electrically couple to the skin of the user. As depicted in FIG. 13, a hand of a user is detaching the removable layer 1395 from the flexible patch 1360 of the smart patch 1300. In some cases, the flexible patch 1360 can be attached to the user after the electronics module is secured therein, although that need not always be the case.

The smart patch 1300 with its flexible backing is designed to minimize the movement of the smart patch 1300 while being worn. To avoid dislodgment of the smart patch 1300 due to external forces, such as tensional, compressional and torsional forces, a layer of non-irritating adhesive (e.g., adhesive layer 1384), such as a hydrocolloid, is provided at least partially on the underside of the smart patch 1300. Consequently, both the adhesive substrate (e.g., adhesive layer 1384) and hydrogel electrodes (e.g., electrode pads 1382) attach to the skin of the user, such as at or near the chest area of the user.

Figure 14:
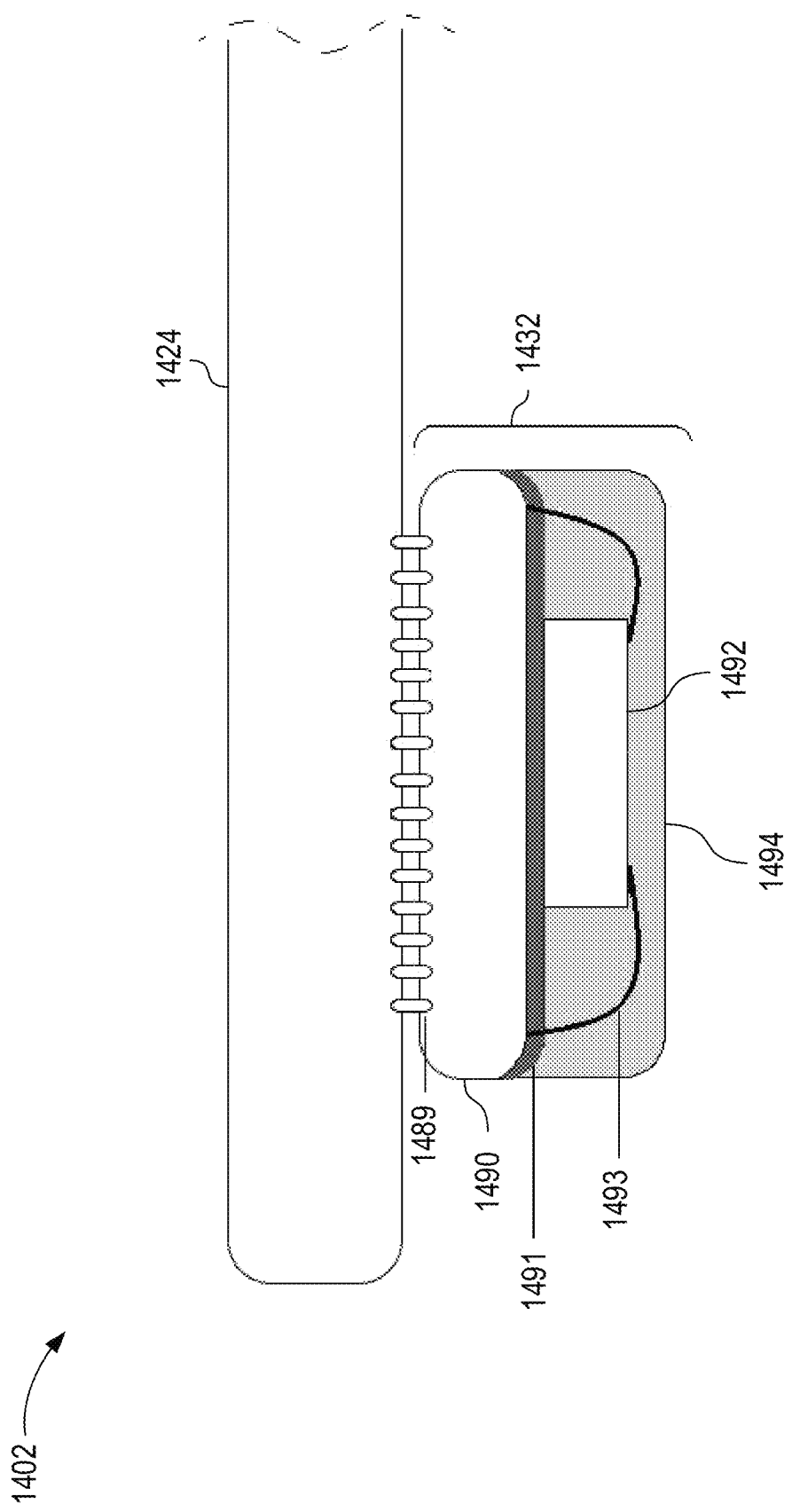
FIG. 14 is a schematic cross-sectional view of the components of an Accelerometer Contact Microphone (ACM) unit as used in an electronics module that is usable in a smart patch, according to certain aspects of the present disclosure.

FIG. 14 is a schematic cross-sectional view of the components of an Accelerometer Contact Microphone (ACM) unit 1432 as used in an electronics module 1402 that is usable in a smart patch, according to certain aspects of the present disclosure. The electronics module 1402 can be any suitable electronics module, such as electronics module 102 of FIG. 1. The ACM unit 1432 can include a microelectromechanical system (MEMS) sensor 1492 encased in a protective and insulating resin 1494 and coupled to an application-specific integrated circuit (ASIC) 1490. The ACM units 1432 (e.g., the ASIC 1490 of an ACM unit 1432) can couple to a PCB 1424 via electrical connectors 1489 (e.g., connector pins or the like).

The MEMS sensor 1492 can be vacuum and/or hermetically sealed, such as within resin 1494. The sealing of the MEMS sensor 1492 protects it and enables stable readings of cardiac and pulmonary sounds. The resin 1494 can be casted into the stacked design of the ACM unit 1432. As the resin 1494 is made of a soft material, it does not mechanically stress the sensing elements and it can stabilize the microenvironment around the elements of the MEMS sensor 1492 and the ASIC. Additionally, the resin 1494 can preserve and protect the bond wires 1493 and their connection from the MEMS sensor 1492 to the ASIC 1490, which may otherwise be relatively weak, and can provide encapsulation for the ACM unit 1432. While depicted on one side of the ASIC 1490, the resin 1494 can cover more than one side or all sides of the ASIC 1490 as long as the ASIC 1490 is able to be electrically coupled to the PCB 1424. In some cases, instead of or in addition to the resin 1494, other alternative materials can be used, such as epoxy and other compatible materials.

The MEMS sensor 1492 can act as a contact microphone, making use of one or more accelerometers (e.g., nano-gap accelerometers) to sense vibration of the chest walls with high sensitivity. The MEMS sensor 1492 can output an electrical signal corresponding to the sensed vibrations.

In some cases, the electrical signal output by the MEMS sensor 1492 can be directed to an application-specific integrated circuit (ASIC) 1490. In some cases, the MEMS sensor 1492 can be mounted to the ASIC 1490 directly or via one or more intermediary layers 1491. An intermediary layer 1491 can be a protective material and/or a die attach material (e.g., a silicone structural adhesive) used to facilitate attachment of the MEMS sensor 1492 to the ASIC 1490 in a stack configuration. Bond wires 1493 can electrically couple the MEMS sensor 1492 to the ASIC 1490, passing through the resin 1494 and through the one or more protective layers 1491. In some cases, three bond wires 1493 can be used to establish a positive line, a negative line, and a ground voltage, although other number of bond wires 1493 can be used.

In some cases, the form factor of the ACM unit 1432 is a package measuring at or approximately (e.g., within 1%, 2%, 3%, 4%, 5%, or 10% of) 2 mm×2 mm×3 mm (length× width×height), although other sizes can be used. The use of a compact design as disclosed herein permits the reduction of electrical parts and system size, especially when multiple ACM units 1432 are to be installed in the same plane within a single electronics module 1402.

The use of a stacked design (e.g., with the ASIC 1490 positioned between the MEMS sensor 1492 and the PCB 1424), as depicted in FIG. 14, can be advantageous, especially in cases where surface area on the PCB 1424 is scarce. Additionally, the stacked design can be advantageous for certain aspects of the present disclosure in which the ACM unit 1432 extends for a distance to make contact with a user's skin. In such cases, the stacked ACM unit 1432 can permit the PCB 1424 to remain further from the user's skin while still allowing the ACM unit 1432 to contact the skin.

In some cases, however, a parallel design can be used. In a parallel design, the ASIC 1490 is positioned horizontally adjacent to the MEMS sensor 1492 and not vertically stacked between the MEMS sensor 1492 and the PCB 1424. The use of a parallel design can be advantageous when a thin ACM unit is desired or otherwise important. In some cases, the parallel design can include disposing the ASIC 1490 and MEMS sensor 1492 on the same plane on a substrate that is hermetically sealed by a molding compound or a ceramic or metal case.

Figure 15:
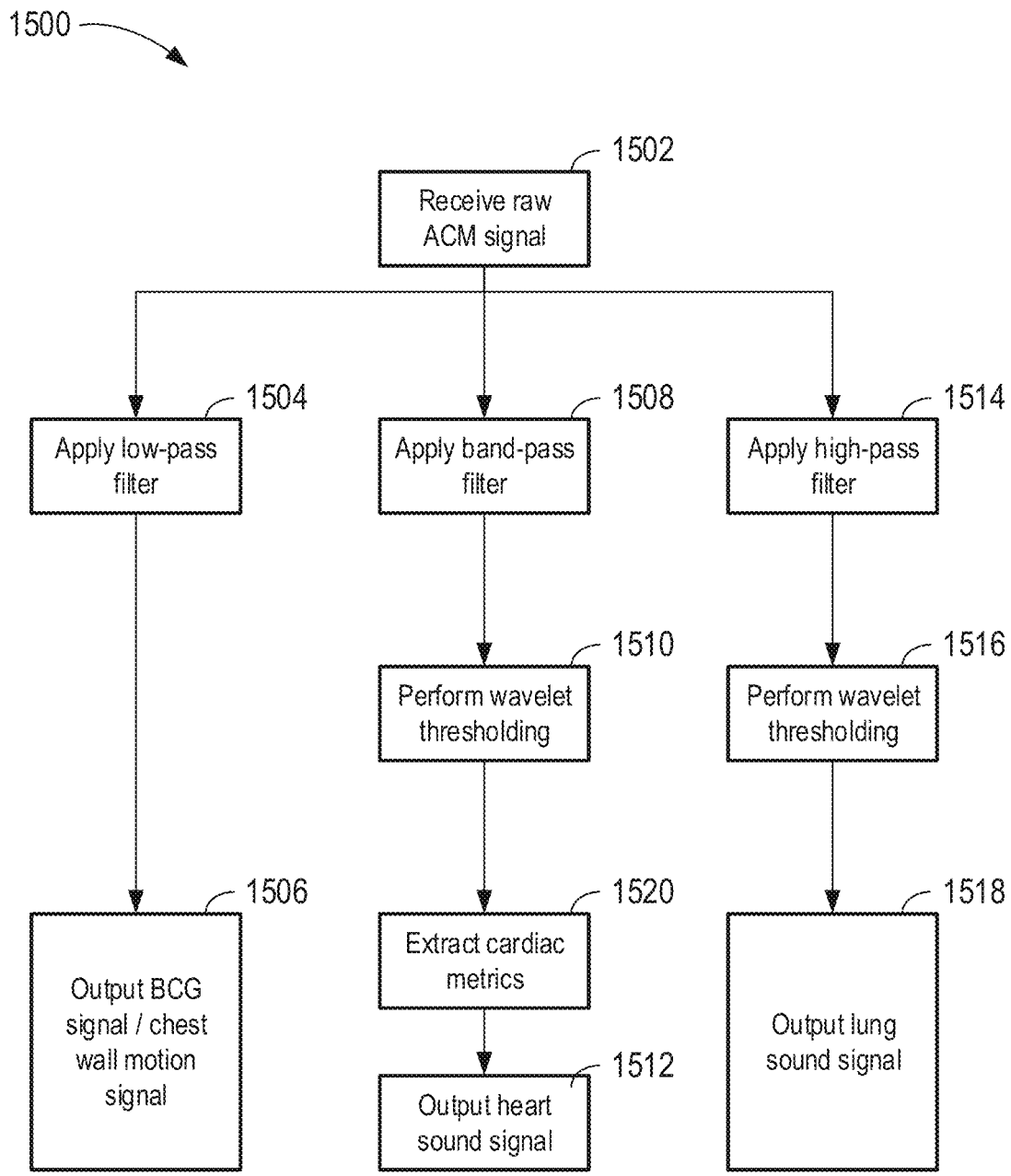
FIG. 15 is a flowchart depicting a process for filtering signals from an ACM unit of a smart patch, according to certain aspects of the present disclosure.

FIG. 15 is a flowchart depicting a process 1500 for filtering signals from an ACM unit of a smart patch, according to certain aspects of the present disclosure. Process 1500 can be performed by any suitable device, such as an ASIC (e.g., ASIC 1490 of FIG. 14) or a processor of a smart patch (e.g., smart patch 600 of FIG. 6). When performed by an ASIC, the ASIC of an ACM unit can receive raw signals from the MEMS sensor of the same ACM unit, then translate them into useful outputs, such as a BCG signal/Chest Wall Motion output signal, a heart sounds output signal, and a lung sounds output signal. Process 1500 can make use of electrical components, electronic components, or a combination of both to perform the necessary filtering and recording cardiopulmonary sounds. The filtering of process 1500 can permit differentiation of heart and lung sounds from the vibration of the chest wall of a user, such as by discerning the audible (e.g., at or greater than 20 Hz) from inaudible frequencies (e.g., at or less than 20 Hz).

Process 1500 can be a high-order Butterworth system of filters, where a wavelet thresholding reduces the noise of the signal and extracts sound features from the raw signals.

At block 1502, the raw ACM signal can be received. The raw ACM signal can be an electrical signal received from the MEMS sensor (e.g., MEMS sensor 1492 of FIG. 14) of an ACM unit or an electronic component coupled to the MEMS sensor (e.g., an ASIC). The raw ACM signal can be indicative of vibrations detected by the MEMS sensor.

At block 1504, a low-pass filter can be applied to the ACM signal. The low-pass filter can be set at 20 Hz, although other cutoff frequencies can be used, such as cutoff frequencies within 1, 2, 3, 4, 5, 6, 7, 8, 9, 10, or 15 Hz of 20 Hz. The resultant signal can be output at block 1506 as a BCG signal and/or chest wall motion signal. This signal can represent chest wall motion and/or ballistic forces generated by the heart (BCG). By tracking the movement of the chest wall, inspiration and expiration can be monitored. Further, a timestamped recording of the respiratory pattern can be leveraged to help locate in time other respiratory sounds by comparing them to the recorded respiratory pattern.

At block 1508, a band-pass filter can be applied to the ACM signal. The band-pass filter can be set to pass frequencies from 20 Hz through 200 Hz, although other high and/or low cutoff frequencies can be used (e.g., one or both cutoff frequencies within 1, 2, 3, 4, 5, 6, 7, 8, 9, 10, or 15 Hz of the given cutoff frequency). The resultant signal can be used to determine heart sounds within the ACM signal. At block 1510, wavelet thresholding can be performed on the filtered signal from block 1508 to generate a heart sound signal, which can be output at block 1512. This signal can represent sounds often associated with the heart.

At optional block 1520, cardiac metrics can be extracted. Cardiac metrics can be extracted after the band-pass filter of block 1508, such as after wavelet thresholding at block 1510. In some cases, cardiac metrics can be output as part of or in addition to the heart sounds signal at block 1512. In other cases, the cardiac metrics can be extracted from the heart sound signal after the heart sound signal is output at block 1512. In an example, once the principal cardiac sounds, S1 and S2 (S1 corresponds to closing of the atrioventricular valves and S2 to closing of the semilunar valves) are recorded, the systole can be calculated as the period from S1 to S2 and diastole as the period from S2 to S1.

At block 1514, a high-pass filter can be applied to the ACM signal. The high-pass filter can be set to a 20 Hz frequency, although other cutoff frequencies can be used, such as cutoff frequencies within 1, 2, 3, 4, 5, 6, 7, 8, 9, 10, or 15 Hz of 20 Hz. The resultant signal can be used to determine pulmonary sounds within the ACM signal. At block 1516, wavelet thresholding can be performed on the filtered signal from block 1514 to generate a lung sound signal, which can be output at block 1518. This signal can represent sounds often associated with the lung.

Some of the algorithms for the wavelet thresholding (e.g., wavelet denoising) can be Fourier based, Bayes based, or level dependent, among others. The raw ACM signal acquired in the MEMS is further filtered in the ASIC component of the ACM unit.

The resultant waveforms after the raw ACM signal is filtered can provide a powerful tool for cardiopulmonary diagnostics, based on the frequency content and amplitude of the signal(s).

In some cases, filtering as described with reference to process 1500 can be used to determine whether or not a particular sound is associated with BCG/chest wall motion or associated with a cardiopulmonary sound (e.g., using a low-pass filter as used at block 1504). The filtering can further determine whether or not a particular sound is associated with the heart of the user (e.g., a heart sound) or the lung of the user (e.g., a lung sound) (e.g., using a band-pass filter or a high-pass filter as used at block 1508 or block 1514, respectively).

While depicted as a flowchart for illustrative purposes, the blocks of process 1500 can be performed in different orders and combinations, with fewer or additional blocks included. For example, in some cases, heart and lung sound signals can be obtained by first passing an ACM through a high-pass filter and then splitting the resultant signal to be i) processed for lung sounds and ii) passed through a band-pass or low-pass filter to be processed for heart sounds.

Figure 16:
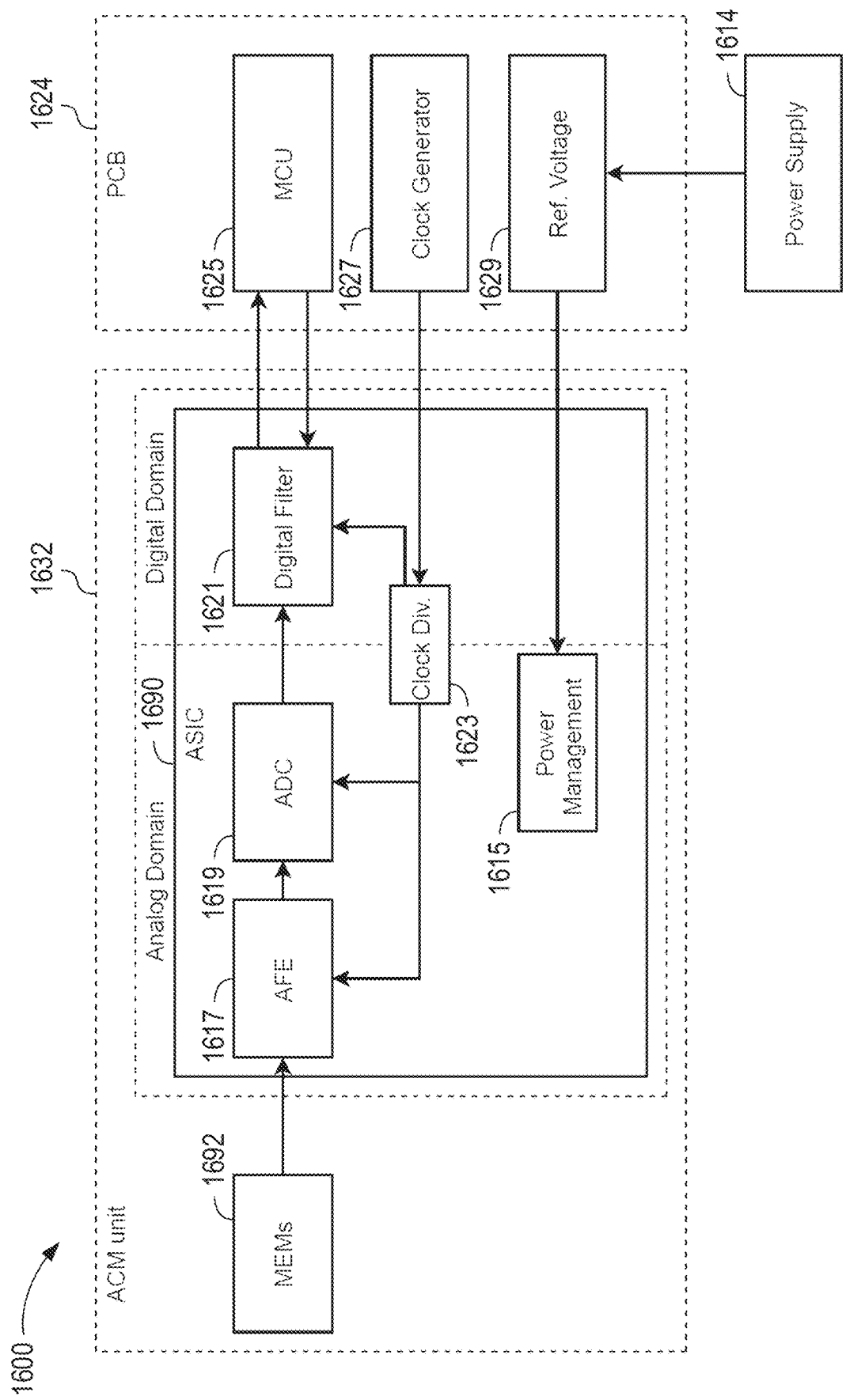
FIG. 16 is a schematic block diagram of components of an ACM unit and their interaction with components of the PCB of the electronics module, according to certain aspects of the present disclosure.

FIG. 16 is a schematic block diagram 1600 of components of an ACM unit 1632 and their interaction with components of the PCB 1624 of the electronics module, according to certain aspects of the present disclosure. ACM unit 1632 and PCB 1624 can be any suitable ACM unit and PCB, such as ACM unit 1432 and PCB 1424 of FIG. 14.

In some cases, the MEMS sensor 1692 of the ACM unit 1632 is a MEMS accelerometer contact microphone based on out of the plane vibrational sensing. The ACM unit 1632 can be a fully integrated system comprising the designed MEMS sensor 1692 enclosed in a ceramic packaging with a specialized ASIC 1690. In some cases, the ASIC 1690 is designed as a signal processing system on a chip.

The ASIC 1690 can include an Analog Front-End (AFE) circuit 1617 at the sensing interface. The AFE circuit 1617 can include a capacitance to voltage converter (CVC), which translates the proof mass displacement of the MEMS sensor 1692 into voltage, and a low noise amplifier (LNA). The output of the AFE circuit 1617 can be passed to an analog-to-digital converter (ADC) circuit 1619. In some cases, the output of the AFE circuit 1617 can pass through an anti-aliasing filter (AAF) before reaching the ADC circuit 1619, such as to restrict the bandwidth of the signal over the band of interest. The ADC circuit 1619 can be an N-bit ADC sampler.

After exiting the ADC circuit 1619, the signal can be in the digital domain and can be filtered by a digital filter 1621 prior to being output to the MCU 1625 (e.g., via connector pins, such as electrical connectors 1489 of FIG. 14).

To accommodate multiple ACM units 1632 (e.g., coupled to a single PCB 1624), a synchronization clock may be incorporated in each ASIC to support the timing for the various sensors. Therefore, the clock generator 1627 from the PCB 1624 can be directly coupled to the clock divider (CLK DIV) 1623, from which time is synchronized with the AFE 1617, ADC 1619, and digital filter 1621.

In some cases, power reduction can be achieved by applying ultra-low-power techniques, including clock gating, power gating, and ultra-low-voltage operation. In terms of powering the ACM unit 1632, the needed current is injected into the ASIC 1690 via its connection with the PCB 1624 of the electronics module. The current harvested from the power supply 1614 by the PCB 1624 is posteriorly set to a reference voltage 1629 and sent to the power management unit 1615 in the ASIC 1690.

Figure 17:
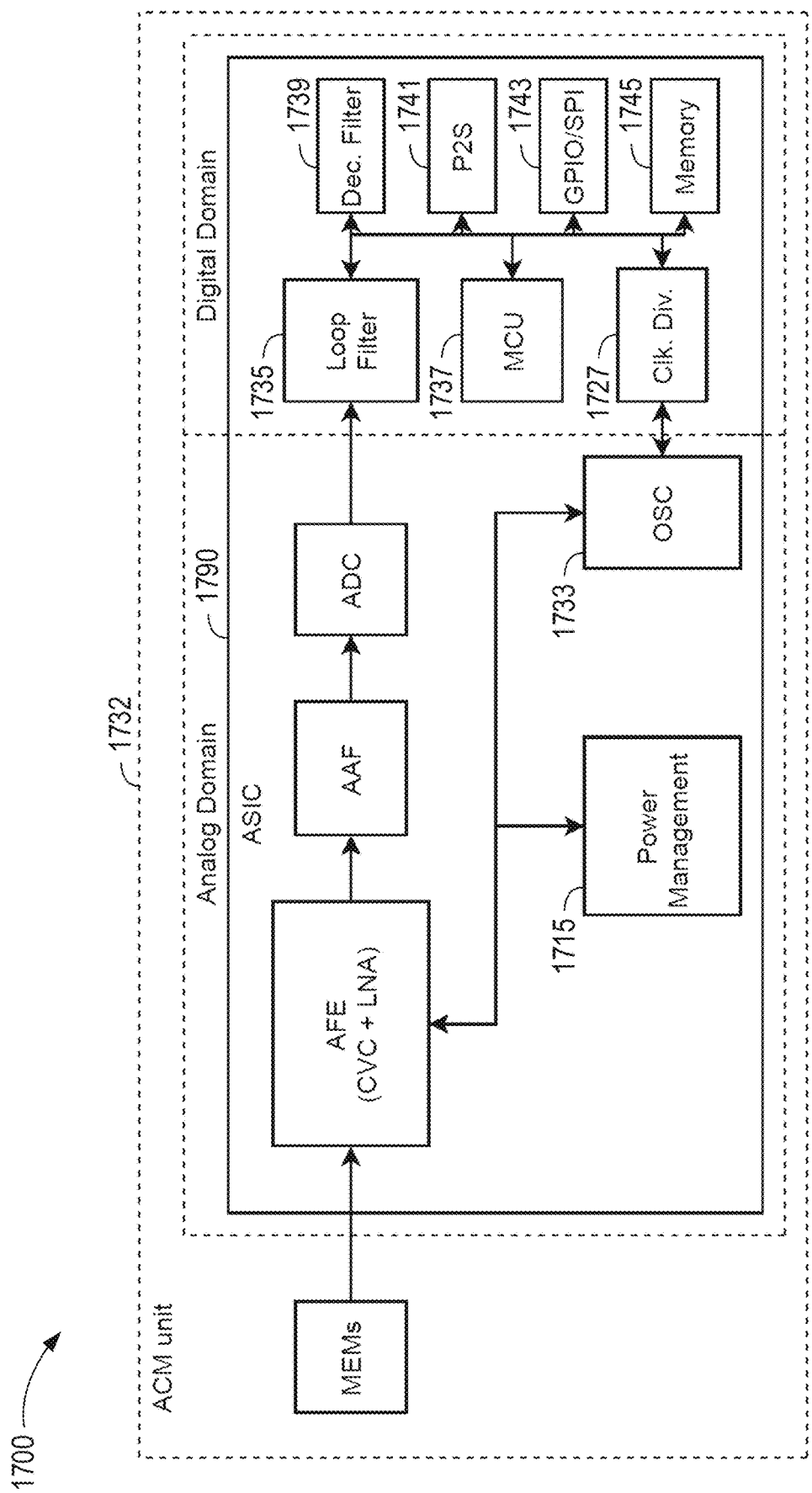
FIG. 17 is a schematic block diagram of components of an ACM unit, according to certain aspects of the present disclosure.

FIG. 17 is a schematic block diagram 1700 of components of an ACM unit 1732, according to certain aspects of the present disclosure. ACM unit 1732 can be any suitable ACM unit, such as ACM unit 1632 of FIG. 16.

Block diagram 1700 of the ACM unit 1732 further specifies integrated components of the specialized ASIC 1790. The digital filter (e.g., digital filter 1621 of FIG. 16) is broken out into components, including a combination of a loop filter 1735 and a MCU 1737 (e.g., to perform microcontroller filtering algorithms). Additionally, before transmitting the sensing data to an external host for post processing, a decimation filtering accelerator 1739 can convert the bit-stream back into parallel data, by performing low-pass filtering and down-sampling.

The MCU 1737 has the function of initialization and configuration of the ASIC system. The ASIC 1790 can be initially provided power, such as from a PCB. After the internal power supplies are stable, the oscillator (OSC) 1733 provides system clocks and also a reset for the MCU 1737, as well as other blocks. The MCU 1737 can then read the program and register information from memory 1745, and start to configure the system.

Along with the MCU 1737 and memory chip 1745, some main supporting blocks in the PCB of the ASIC 1790 are the power management (PM) unit 1715, a serial peripheral interface (SPI) control interface and/or general-purpose input/output (GPIO) 1743 to enable communication with external microcontrollers, and a parallel-to-serial (P2S) converter 1741.

Figure 18:
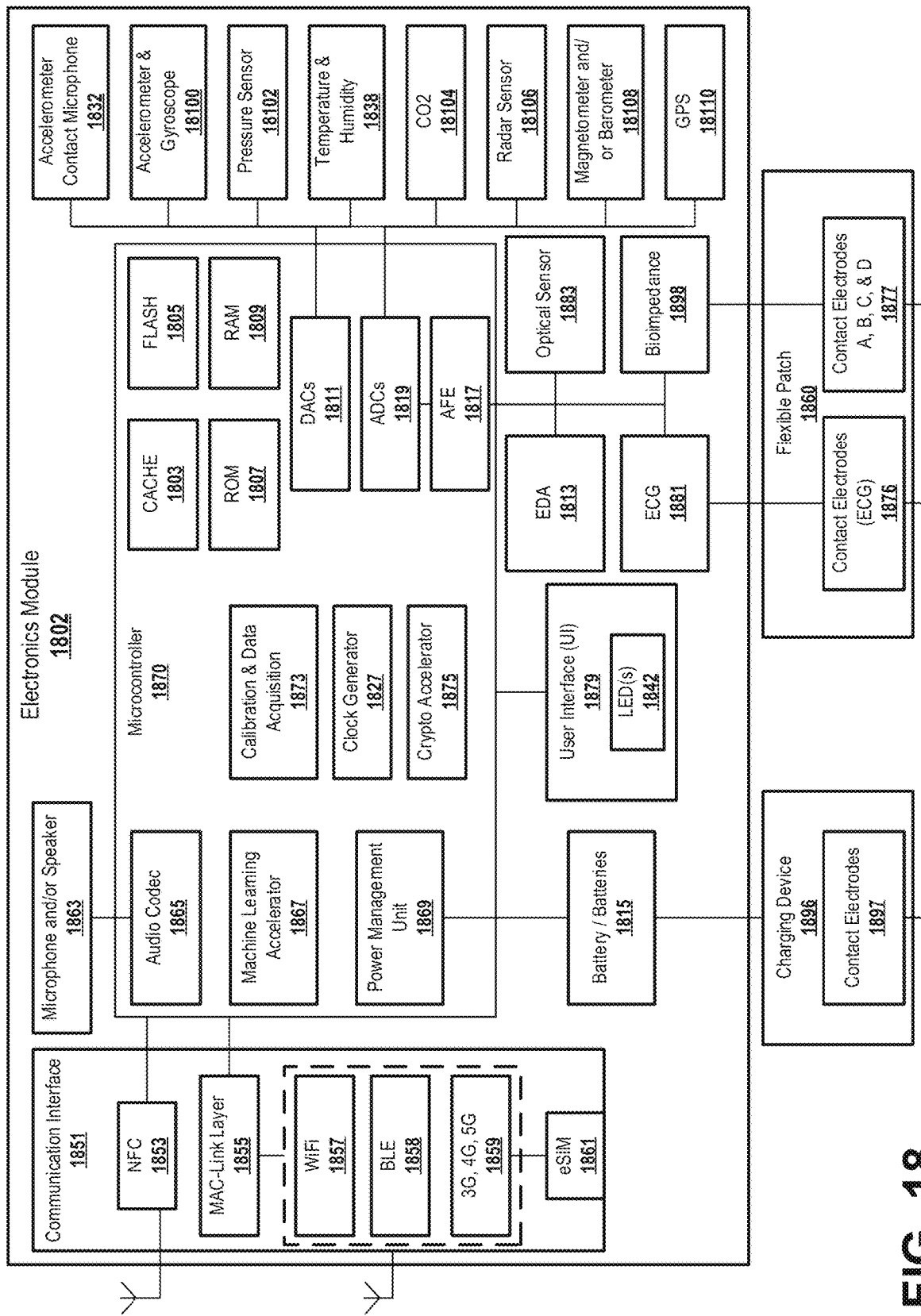
FIG. 18 is a schematic block diagram illustrating components of an electronics module, according to certain aspects of the present disclosure.

FIG. 18 is a schematic block diagram illustrating components of an electronics module 1802, according to certain aspects of the present disclosure. Electronics module 1802 can be any suitable electronics module, such as electronics module 102 of FIG. 1.

Physiological monitoring and other functions are performed by the electronics module 1802 through a microcontrolled architecture. The electronics module 1802 can include one or more microcontrollers 1870, one or more sensors (e.g., a pressure sensor 18102), one or more communication interfaces 1851, one or more user interfaces 1879, one or more microphone and/or speakers 1863, and one or more batteries 1815 (e.g., rechargeable batteries) to power the circuitry.

The electronics module 1802 can be inserted into a receptacle of a flexible patch 1860 (e.g., flexible patch 660 of FIG. 6). The flexible patch 1860 can include six hydrogel contact electrodes (e.g., electrode pads, such as electrode pads 982A-F of FIG. 9) that can be used for ECG measurements (e.g., via contact electrodes 1876) and to collect bioimpedance signals (e.g., via contact electrodes 1877). In other cases, two pairs of hydrogel electrodes can be used to gather both ECG and bioimpedance data with periodic readings for each, controlled by the MCU 1870. In other cases, there may be fewer or more contact electrodes implemented in the substrate of the flexible patch 1860, and in turn the electronics module 1802.

The microcontroller 1870 may include one or more CPUs, MCUs, DSPs, and Machine Learning Accelerators 1867 (e.g., GPUs, neural processors, and the like). The microcontroller 1870 can be integrated on the PCB and can process the physiological data captured from the integrated sensors. The microcontroller 1870 commands and processes the data calibration and acquisition module 1873 from the implemented sensors. The highly optimized microcontroller 1870 can be designed to provide high compute capability at low power. The microcontroller 1870 interprets input signals (e.g., input signals from multiple ACM units 1832 or input signals from data received via wireless communication via communication interface 1851) and generates monitoring data outputs. In some cases, the microcontroller 1870 integrates a Machine Learning (ML) Accelerator 1867, which facilitates artificial intelligence (AI) models to be used for sensor fusion or multi-sensor data processing. Moreover, the ML accelerator 1867 helps to run on-device ML models for processing health metrics, obviating the need to connect to a server over a wireless interface to process the raw data. This on-device processing also helps to extend the battery life. The microcontroller 1870 can support a range of real-time operating systems (OS), including Wear OS, Linux, WebOS, Tizen, and FreeRTOS, depending on the applications of the smart patch or the interfacing requirements of other connected devices. For example, a smart patch that is designed to be an extension of your smartphone may run an advanced operating system compatible with the OS of the smartphone.

In some cases, one or more microphones (e.g., of microphone and/or speaker 1863) can be integrated in the electronics module 1802 for receiving voice commands from the user or for speech analysis to monitor mental and physical health (e.g., speech analytics to identify dementia or dementia-related symptoms). For example, the user may be able to use a trigger phrase (e.g., "Hey Anexa") to activate an electronic assistant capability, which allows the user to verbally report symptoms such as chest pain, difficulty breathing, lightheadedness, weakness, and the like. User symptom reports can be date/time stamped and synchronized with physiological data, activity data, location data, environment data, or other data acquired/generated by the smart patch or even other wearable devices that the user may be wearing (e.g., a smart watch). Physicians can then correlate the date/time symptoms appeared with other temporal data to come up with deeper insights related to the patient's health condition. In some cases, the electronics module 1802 includes one or more speakers (e.g., of microphone and/or speaker) 1863, which can allow the on-device assistant, or other module, to verbally communicate with the user. The microphone and/or speaker 1863 can communicate with the MCU 1870 via an audio codec 1865 implemented in the microcontroller 1870. The MCU 1870 can integrate speech recognition algorithms, speech processors, speech synthesizers, and other capabilities that allow the device to verbally communicate with the user and have multi-turn conversations. For example, the on-device assistant powered by the MCU 1870 may be able to ask the user follow-up questions to get additional information about reported symptoms, confirm certain symptoms that may be ambiguous, or ask about the severity of symptoms (e.g., chest pain on a 0-10 scale). Based on event triggers, such as a change in health metrics (e.g., significantly decreased average oxygen saturation during sleep), health events (e.g., cardiac arrest), or activity detection (e.g., fall), the on-device assistant may be able to contact emergency services automatically or at the user's request, such as using its wireless communications interface 1851. Such contact may entail placing a call over a voice channel or sending a message to emergency services over a communications network. In both scenarios, the electronics module 1802 may be able to alert and provide emergency services with the user's personal information (e.g., name, age, location data, and the like), the user's condition based on physiological data processed by the MCU 1870 (e.g., cardiac arrest detected), the user's state (e.g., fall detected by the device), and other pertinent information. The electronics module 1802 may automatically grant emergency services the ability to access its real-time sensor data, recorded electronic health reports for remote monitoring purposes based on the event trigger (e.g., cardiac arrest, fall, and the like), and the user's electronic health records stored on a healthcare server.

Since the electronics module 1802 of the smart patch is battery powered, a power management unit 1869 can be integrated into the MCU 1870 to help reduce power consumption. In some cases, the electronics module 1802 can be continuously recording physiological signals and wirelessly transmitting data to another device. For example, the electronics module 1802 may be connected to a smartphone or a healthcare server via a wireless communications interface 1851 to continuously transmit data being captured by the device. The MCU 1870 can employ algorithms to optimize its performance and energy consumption. In some cases, certain actions, such as wireless communications, sensor data collection, and/or sensor data processing can be performed only occasionally (e.g., at regular intervals) or dynamically (e.g., in response to a detected event or activity). In some cases, other factors (e.g., time of day, location, physiological measurement, and others) can be used to adjust when these actions occur. For example, the ECG/lung sensing and processing may be performed less frequently at nighttime, but more frequently after eating a meal or while exercising.

Wireless communication can enable the electronics module 1802 to interact with one or more devices. A wide range of wireless transceivers that can provide wireless interfacing capabilities may be integrated into the device's communications interface 1851 including: NFC/RFID 1853, WiFi 1857, Bluetooth Low Energy (BLE) 1858, and mobile network interface 1859, among others. The communications interface 1851 can be optimized to consume low power and conserve battery. Moreover, through the control of the Media Access Control (MAC) link layer 1855, the microcontroller 1870 can enable connectivity to mobile networks based on standards such as 3G, 4G, 5G, LTE, LTE-M, NB-IoT, and the like. In some cases, an embedded SIM (eSIM) 1861 may be integrated into the communications interface 1851 to enable wireless broadband communication over a mobile network. The eSIM 1861 can be in the form of a programmable SIM card embedded directly into a device, although that need not always be the case. The eSIM 1861 can obviate the need for a physical SIM card in the smart patch, which can improve reliability and security while also reducing space requirements (e.g., because a SIM connector is no longer needed). An eSIM 1861 can be provisioned to the smart patch remotely, and can enable the electronics module 1802 to connect to different mobile network operator (MNO) networks.

The communications interface 1851 may support one or more antennas that allow the electronics module 1802 to wirelessly communicate with other devices. In some cases, the antennas systems can be integrated into a wireless antenna module (e.g., wireless module 126 of FIG. 1). The wireless module 126 can be off-board (e.g., off the main PCB) and can be situated in the divider (e.g., divider 116 of FIG. 1). The wireless module 126 can include one antenna that enables NFC/RFID communication and another antenna that supports WiFi, BLE, and/or mobile network communication. In some cases, however, the antenna module can be embedded into the PCB with the communications interface 1851. The communications interface 1851 may also support other wireless communication hardware and standards such as Worldwide Interoperability for Microwave Access (WiMAX) and ultra-wideband (UWB).

The electronics module 1802 may be configured to interface with a wireless local area network (WLAN), wide area network (WAN), and/or wireless personal area network (WPAN). Besides wireless communication, in some other cases, an adaptor may be used that supports physical connections, such as using USB (universal serial bus), USB-C, and the like. Physical connections can be used to offload data stored in the electronics module 1802 or otherwise program or configure the electronics module 1802. In some cases, a communications bus can enable the flash memory 1805 to be directly accessed externally over the external connector when the electronics module 1802 is physically interfaced to another electronic device.

Protecting the user's physiological data stored in the electronics module 1802 can be an important feature. Additionally, all user data transmitted to a connected device via a wireless connection should be secured. The electronics module 1802 can implement a cryptographic accelerator 1875 to ensure a high level of data security. The cryptographic accelerator 1875 can be a dedicated processor for encryption, compression and related processing. The functions of the cryptographic accelerator 1875 can alternatively be supported by the CPU/MCU/DSP. Additional security capabilities incorporated into the electronics module 1802 may include firmware integrity and secure boot, mutual authentication for device identification, end-to-end encryption, tamper detection, and side-channel attack protection.

In some cases, the components of the electronics module 1802 may be used for multi-sensor data processing, novel dataflow architectures, tasks requiring in-memory computing capability, accelerating algorithms, and other tasks. The ML accelerator 1867 can make use of on-board memory, or can have high-throughput, on-chip memory for data intensive AI tasks. Thus, continuous sensor data processing can be enabled to detect medical conditions. Moreover, the ML accelerator 1867 can facilitate the use of comprehensive algorithms and software for employing a multimodal ML approach for certain predictions/inferences of complex medical data. For privacy and reliability, the electronics module 1802 can run optimized ML models locally. The ML accelerator 1867 can support a wide range of optimized ML models that use Deep Neural Networks (DNNs), Convolutional Neural Networks (CNNs), Recurrent Neural Networks (RNNs), Long Short-Term Memory (LSTM) models, or other techniques that can be used individually or in combination for processing the sensor data. The use of on-device models can enable high-accuracy detection of health conditions/states with minimal errors. On-device models can be trained on a server, compressed, transmitted to the smart patch over a communications network, and stored in memory so they can be executed in a ML pipeline by the ML accelerator 1867. Predictions/insights generated using these on-device models can be transmitted from the electronics module 1802 to a remote computing device, such as a healthcare server, to help clinicians improve the diagnosis, management, and treatment of the diseases.

In an example, the ML accelerator 1867 can process ECG, PCG, BCG, and SCG data using multimodal ML models that generate predictions/inferences. In another example, physiological data, activity data, and environment data can be combined to detect and identify triggers for palpitations. Palpitations are sometimes irregular, short lived, and difficult to detect. However, by combining patient-specific and environment data, the machine learning system can easily generate clinical insights for the detection and treatment of palpitations.

Primary memory is incorporated in the microcontroller to store data and instructions to facilitate the processing of data. In some cases, both types of primary memory, Random Access Memory (RAM) 1809 and Read Only Memory (ROM) 1807, can be included, optionally along with flash memory 1805 and/or EPROM memory and the like. Although the RAM 1809 is volatile, the CPU interacts with RAM 1809 to get the data and instructions for processing. ROM 1807 is a non-volatile memory device, so it can be used for firmware updates or/and saving instructions from the OS. In some cases, cache memory 1803 is built into the microcontroller 1870 and may be located on a separate chip in proximity to the CPU and RAM 1809, although that need not always be the case. Cache memory is a storage buffer that increases the speed of processing.

The circuitry of the electronics module 1802 can also include a flash memory 1805, which the microcontroller can use for storing digitized physiological data and other information. Data compression techniques may be used on data captured via sensors or generated by the electronics module to reduce memory usage. Data compression techniques can also improve the efficiency of wireless transmissions. In some cases, data may be transmitted to a computing device, such as a healthcare server, where it can be stored in a database (e.g., EHR) or further processed. Data compression techniques can include any suitable technique for compressing the size of data and/or reducing a set of data to only desired data. For example, data compression techniques can include classical data compression, feature extraction, resolution decreasing, and the like. Data compression techniques can include lossless and/or lossy compression techniques.

The user interface 1879 can include, but is not limited to, light-emitting diodes (LEDs) 1842 (e.g., organic LEDs), a mechanical, electromechanical, or piezoelectric audio signaling device (e.g., a buzzer), a speaker (e.g., speaker of microphone and/or speaker 1863), or an actuator (e.g., Electro-Mechanical Polymer Actuator, Linear Resonant Actuator, etc) enabling haptic feedback vibrations. The LEDs 1842, buzzers, and haptic feedback actuators may be used by the microcontroller 1870 to output feedback that alerts the wearer of the smart patch of device events (e.g., power up, low battery, sensor issues, medical alerts, environmental alerts, and the like). The lights may include two LEDs 1842 with different discrete wavelengths that emit different colors (e.g., red, green, yellow, etc.) to indicate battery levels, sensor states, wireless connection status, or other device states. The LEDs 1842 can be included in the sidewall of the bottom portion of the electronics module 1802, although that need not always be the case. Each LED 1842 can emit a different color and be used for different alerts to a user. For example, a green light may blink three times to notify the user that the device is affixed to the user and is capturing physiological data correctly from all sensors; or a periodically increasing blink of a red LED might indicate low battery levels. The outputs provided by the user interface 1879 may be responsive to, or be initiated by, a program or application executed by the processor or associated device through the communications interface 1851. In some cases, the user interface 1879 can include buttons, pinhole buttons, slider switches, ultra-miniature tactile switches, and the like. In some cases, LEDs 1842 can be positioned on or near different sides or edges of the electronics module 1802, or in otherwise distinguishable positions on the electronics module 1802, which may improve distinguishability for individuals unable to discern the color differences of the LEDs 1842. In some cases, an accelerometer and/or gyroscope 18100 (e.g., an IMU) can be used as part of the user interface 1879 to receive inputs from the user (e.g., taps or presses).

The electronics module 1802 includes a sensor subsystem including one or more sensors for obtaining sensor data. A wide range of analog sensors can be used to provide comprehensive user monitoring via the wearable smart patch. The sensors acquire data related to the user's health state (e.g., physiological data), the user's physical activity (e.g., actigraphy, motion evaluation, steps, body position, and the like), the user's location, and the user's environment (e.g., environmental CO2, barometric pressure, altitude, and the like).

Signals acquired from the sensors (e.g., ECG, bioimpedance, optical sensors, and the like) can be processed in the analog domain, converted to digital, and further processed in the digital domain. This workflow allows the sensor data to be analyzed, manipulated. and enhanced prior to storage, transmission, and/or further processing.

The analog signals received from the sensors can be conditioned by the analog front-end (AFE) 1817, which can provide dedicated signal paths for each analog input channel, enabling true multichannel, simultaneous sampling capabilities. In some cases, an analog input channel includes an EMI filter, a multiplexer, a programmable gain amplifier (PGA), and a 24-bit analog-to-digital (ADC) converter 1819, although other combinations can be used. An analog-to-digital converter (ADC) 1819 converts analog signals into a digital signal that can be processed by the CPU, and a digital-to-analog converter (DAC) 1811 can perform the reverse function. In some cases, a multichannel ADC/DAC unit capable of processing data at very high speeds can be integrated in the signal path.

Sensors can include non-contact sensors that rely on line-of-sight to the user's skin through the translucent or transparent sensor window or proximity to the user's skin. Sensors that perform measurements from the surface of the user's skin from behind the sensor window may include optical sensors, imaging sensors, thermal imaging sensors, laser sensors, ultrasonic Doppler flow meters, electromagnetic flow meters, millimeter wave (mmWave) sensors (e.g., 60-64 GHz, 76-81 GHz), and the like.

As disclosed herein, the electronics module 1802 can include at least one accelerometer contact microphone (ACM) unit 1832. The ACM unit 1832 can use a MEMS sensor with nano-gap accelerometers to capture the vibration of the user's chest wall and transform those mechanical signals into high quality audio signals. The small MEMS accelerometers that comprise the sensing portion of the ACM unit 1832 enable a wide operational bandwidth and micro-g resolution. The MEMS device can be sealed and encapsulated along with an ASIC. The inner vacuum can enhance the signal-to-noise ratio in a high resonant frequency microstructure with small form-factor. In some cases, the ACM unit 1832 can measure heart sounds propagated in the body of a user, along with cardiac values such as heart rate (HR) and heart rate variability (HRV). Besides HR and HRV, the ACM unit can provide phonocardiogram (PCG), electrocardiogram (ECG), and ballistocardiogram (BCG) signals when the sensor is recording in contact with the chest of a user. In some cases, the ACM unit 1832 can be used to record lung sounds and extract respiratory metrics. Physiology related information can be extracted from the respiration pattern and lung sounds (e.g., the pulmonary capacity or an obstruction of the airways could be detected) by identifying the timing and location of abnormal breathing sounds within a respiratory cycle.

In some cases, the auscultation locations for cardiopulmonary sounds are available in the second intercostal space (ICS) on the chest, where the patch is coupled to the skin of the wearer. Using the ACM unit 1832, physicians and researchers can observe heart and lung sounds remotely with more accuracy and precision than previous auscultation techniques. Moreover, the ACM unit 1832 provides a user with readings of the low frequency chest motion as additional information that can be processed and combined with the information provided by the accelerometer and gyroscope 18100 from the PCB. In addition to sound recordings, the use of three ACM units 1832 in the same device and placed strategically on the base of the electronics module 1802 facilitates the triangulation of the signal. With sound signal triangulation, the cardiac or pulmonary origin of each sound may be extrapolated to detect and localize dysfunctions in the cardiorespiratory system.

The accelerometer and gyroscope 18100 provide motion data that can be complemented by data from the magnetometers and/or barometric altimeters 18108. Motion and position sensors, like accelerometers and gyroscopes 18100, can capture complex translation and rotation values that may determine the movement of a human body and pose angle in order to compensate for artifacts in the recording signals due to the change of body pose (e.g. lying, standing, and other poses). Accelerometers and gyroscopes 18100 may also be utilized to keep track of body motion, thus generating data for step counting, walking speed, running speed, and sleep monitoring.

The electronics module 1802 includes a magnetometer (e.g., magnetometer and/or barometer 18108) for measuring magnetic fields with several applications including sensing the presence of magnetic wireless charging devices. The magnetometer can be used in combination with an accelerometer and gyroscope 18100 as an inertial measuring unit (IMU). The IMU fixes the relative movements of the body of a user to the coordinate system of the earth, which can be helpful in detecting the absolute orientation of the user. In some cases, the IMU could be used for fall detection or to determine when a user has completed a determined workout exercise as determined by a paired smartphone app that may have access to the data. In collaboration with other sensors, the magnetometer can be used to detect breathing patterns or sleep disorders by measuring a variation in the earth's magnetic field. Along with the barometer (e.g., of magnetometer and/or barometer 18108), which provides the environmental pressure, the magnetometer and/or barometer 18108 can be used to determine altitude. In a complementary way, the pressure sensors 18102 can be used as well for fall detection when detecting rapid altitude changes.

The electronics module 1802 can include a temperature/humidity sensor 1838 that generates temperature data for calibrating other measurements, such as heart rate, and also generates skin humidity/moisture readings. The temperature sensor may be configured to acquire temperature data from the user's skin, the ambient environment, and/or electronic components (e.g., battery, PCB, and the like). The temperature sensor can measure and help show the relative temperature changes on a daily basis so that prolonged fever or sudden temperature changes are recorded. This functionality can facilitate the prediction of or determination of a user having an elevated body temperature, such as if the user has a fever.

A carbon dioxide ($CO_2$) sensor 18104 or some other air quality sensor (e.g., a carbon monoxide sensor, or the like) can be integrated in the PCB to alert the user of potentially dangerous gases in the surrounding areas. High levels of $CO_2$ in a confined space can be dangerous. Elevated $CO_2$ levels can increase headaches and cause lethargy while lowering ability to concentrate on high-level tasks. Therefore, the $CO_2$ sensor 18104 may be used alone or in combination with other environmental sensors to monitor air quality and ventilation around the user. The $CO_2$ sensor 18104 can enable displaying $CO_2$ levels on a connected computing device (e.g., smartwatch, smartphone, etc) and further enable a threshold for an alarm, where 0.7% is set as the maximum level of $CO_2$ concentration for the user to withstand without experiencing adverse health conditions. The CO2 sensor or another air quality sensor can be an electrochemical sensor, a photoionization detector, an optical sensor, or other similar sensor.

Radar sensors 18106 can be integrated in the PCB for healthcare applications, thanks to their capability to identify gestures and micro-scale movements of individual body parts. In some cases, the radar sensor 18106 can serve as a proximity sensor located in a base of the electronic device to measure the proximity of the skin of a user in order to ensure close contact of the electronic device. In some cases, the radar sensors 18106 can provide feedback about the relative location of the smart patch on the chest area of a user and whether the position should be modified. The radar sensor 18106 can track micromotions of the smart patch relative to the skin of the user and use them to interact with the positioning instructions in the device. Another application of the radar sensor 18106 includes measuring the blood pressure complementary to the PPG sensor by measuring the skin motion produced by the pulse travelling along the arteries at each heartbeat. Radar sensors such as mmWave sensors may be incorporated and used for non-invasive continuous blood glucose level monitoring. It has been found that blood samples of higher glucose concentrations are correlated with reflected mmWave signals of greater energy.

Additionally, by integrating a GPS module 18110, the location of a user could be detected to create map routes with user activity segments (e.g., walking, running, cycling, and the like) or send the location information of the smart patch to health care providers if there is a fall detection alert or other medical emergency detected. The GPS coordinates can be translated into a street address or semantic location (e.g., Central Park in New York City) by using a server.

The PCB can include optical sensors 1883 for performing non-contact measurements (e.g., through the sensor window 412 of FIG. 4). Pulse oximetry via the optical sensors 1883 can be used to non-invasively obtain heart rate (HR) and peripheral oxygen saturation (SpO2) of patients based on photoplethysmography (PPG), an optical principle for the measurement of blood volume changes in the microvascular bed of tissue beneath the skin. The optical sensors 1883 can include various types of light emitters, such as non-visible light emitters, visible light emitters (infrared), red LED, or other forms of light emission and corresponding sensors. Depending on the light's wavelength, variations in different layers of the tissue are captured: Blue and green light measure the blood volume changes in the superficial capillaries, yellow reaches the arterioles in the dermis, and red or infrared even reach the small arteries in the hypodermis. The optical sensors 1883 can include one or more emitters and one or more photodetectors, which can be provided on the bottom of the PCB and used as an optical array measurement system.

In some cases, the photodetectors and/or the emitters of the optical sensors 1883 are arranged in a circle around the center of the PCB bottom. The utilized wavelength of the PPG is 520 nm (green), which measures the blood volume changes in the superficial capillaries of the uppermost epidermis. Using the arrangement depicted in FIG. 2, the light emitters and sensors minimizes crosstalk between components and ensures that light absorption is measured, rather than scattering. The close disposition of the LEDs and photodiodes on the same side of the PCB can achieve a significant noise reduction, which can appear from the relative motion of the sensor window and the user's skin. Determined by the systolic and diastolic phase of the cardiac cycle, the heart generates a pulse wave that travels through the body as a difference in blood pressure and volume. This is, therefore, measurable with PPG and enables the estimation of HR by identifying and counting the average pulse beats per minute. In addition to heart rate and heart rate variability, optical sensors 1883 may determine blood oxygen levels, blood pressure, and calibration for glucose level. Blood oxygen saturation (SpO2) is an important vital sign for assessing a user's physical health as low blood oxygen levels can indicate hypoxemia, which can compromise organ function if it is not properly treated.

For measuring glucose levels, infrared LEDs can emit light in a wavelength range between 850 nm and 1000 nm, for example, at about 940 nm. After the light is absorbed by the skin, glucose transforms the light into heat that is immediately dissipated, enabling a measurement of temperature change, which can be used to calculate the blood glucose level of the user. Similarly, infrared (IR) sensors can capture the variation of IR light reflected by the skin of the user, which can be used to estimate the glucose level. However, temperature and IR sensors are not the only source of data to calculate glucose levels. In some cases, ECG sensor and/or bioimpedance sensor data may be used to measure blood glucose level.

By focusing specifically on lowering the sampling rate and analysis of the spectrum of frequencies alone, the power required can be reduced or minimized, and the optical sensors 1883 can be used to detect the dominant frequencies of the heart rate and respiration rate, and the presence of sympathetic nerve activity (SNA). Breathing patterns result in fluctuations of the blood pressure, the so-called respiratory-induced intensity variation (RIIV), where volume changes are observable in PPG signals as an oscillation at the respiration frequency. Additionally, respiration rhythms and transitions can appear as slight variations in heartbeat distance, the so-called respiratory sinus arrhythmia (RSA), which can be detected by optical sensors 1883. The sympathetic nervous system, with a faster response, controls the shortening reactions of fight or flight in case of a threat. Therefore, the sympathetic nerve activity (SNA) plays an important role in the monitoring of cardiovascular diseases such as hypertension, heart attacks, cardiac arrhythmia, and congestive heart failure. In conjunction with the EDA measurements (e.g., via EDA 1813) of sweat production, the PPG sensors can be used to measure the SNA by detecting low-frequency oscillations in the arterial blood pressure, which may spontaneously occur in conscious humans. The extraction of respiration and SNA features may be achieved by performing spectral analysis over the raw sampled PPG data relying on the fast Fourier transform (FFT) to divide a window of PPG data into its frequency components.

The hydrogel electrodes 1876, 1877 in the patch adhesive can be used once they are electrically coupled to the contacts on the electronics module. The ECG electrodes 1876 in contact with the skin of a user capture electrical activity of the heart measured by the amplified skin current. One or multiple electrical voltage values can be used for monitoring the cardiac rhythm of a user. The flexible patch 1860 contains pre-positioned hydrogel electrodes that allow monitoring of high-resolution ECG rhythm and subsequent calculation of the user's heart rate. The HRV is measured as the time variation between heartbeats. The ECG sensor 1881 can be used to measure the stress levels of a user. The correlation between the HRV and stress levels is inversely proportional; a higher level of stress is measured through low HRV values while stress recoveries show increased HRV.

Additional electrodes (e.g., contact electrodes 1877) on the bottom of the device can enable bioimpedance recording. The bioimpedance sensor 1898 can be used to measure impedance of biological tissue at a single frequency or at a series of frequencies using a bioimpedance spectroscopy approach. Bioelectrical impedance measurements can be used to estimate the hydration level of the user, muscle composition of the user, fat composition of the user, body mass index (BMI) of the user, blood glucose levels of the user, and/or average daily calorie requirement of the user. The bioimpedance sensor 1898 can be used to keep track of the user's body fat percentage and predict the basal metabolic rate (BMR) at different moments of the day. These health metrics may be displayed on the smartphone or smartwatch via a compatible app or may be utilized to generate other functions, such as personalized workouts and suggested times for exercising and eating. Data logging and alarm functions may be included in the electronics module 1802 to track glucose levels when glucose levels get too high or too low, outside of a prescribed, safe range.

All the different sensors can be synchronized onboard. The PCB can include a clock generator 1827 to synchronize the data and create time-based reports with all the captured or generated data. Moreover, by synchronizing the sensor readings, crosstalk between sensors in close proximity can be prevented. In some cases, one solution for synchronization of sensors employs the shortest path algorithm to minimize the overall clock drift in the system based on the readings. Besides providing accurate current time, the clock generator can fire a timer at regularly set intervals and perform time calculations, manipulations, and conversions.

The electronics module 1802 can be charged by a charging device 1896, as disclosed in further detail herein. Charging device 1896 can couple to the electronics module 1802 via contact electrodes 1897, although other techniques can be used. In some cases, contact electrodes 1897 coupled to the electronics module 1802 via the same or similar electrical connections as contact electrodes 1876, 1877.

In some cases, the electronics module 1802 can include different combinations of the various components and modules described above. For example, not all modules and/or not all sensors may be used in some cases, or additional modules and/or additional sensors may be used. In some cases, various modules shown within microcontroller 1870 can be performed by one or more microcontrollers, which may be the same as or separate from a primary or main microcontroller or processor of the electronics module 1802.

Figure 19A:
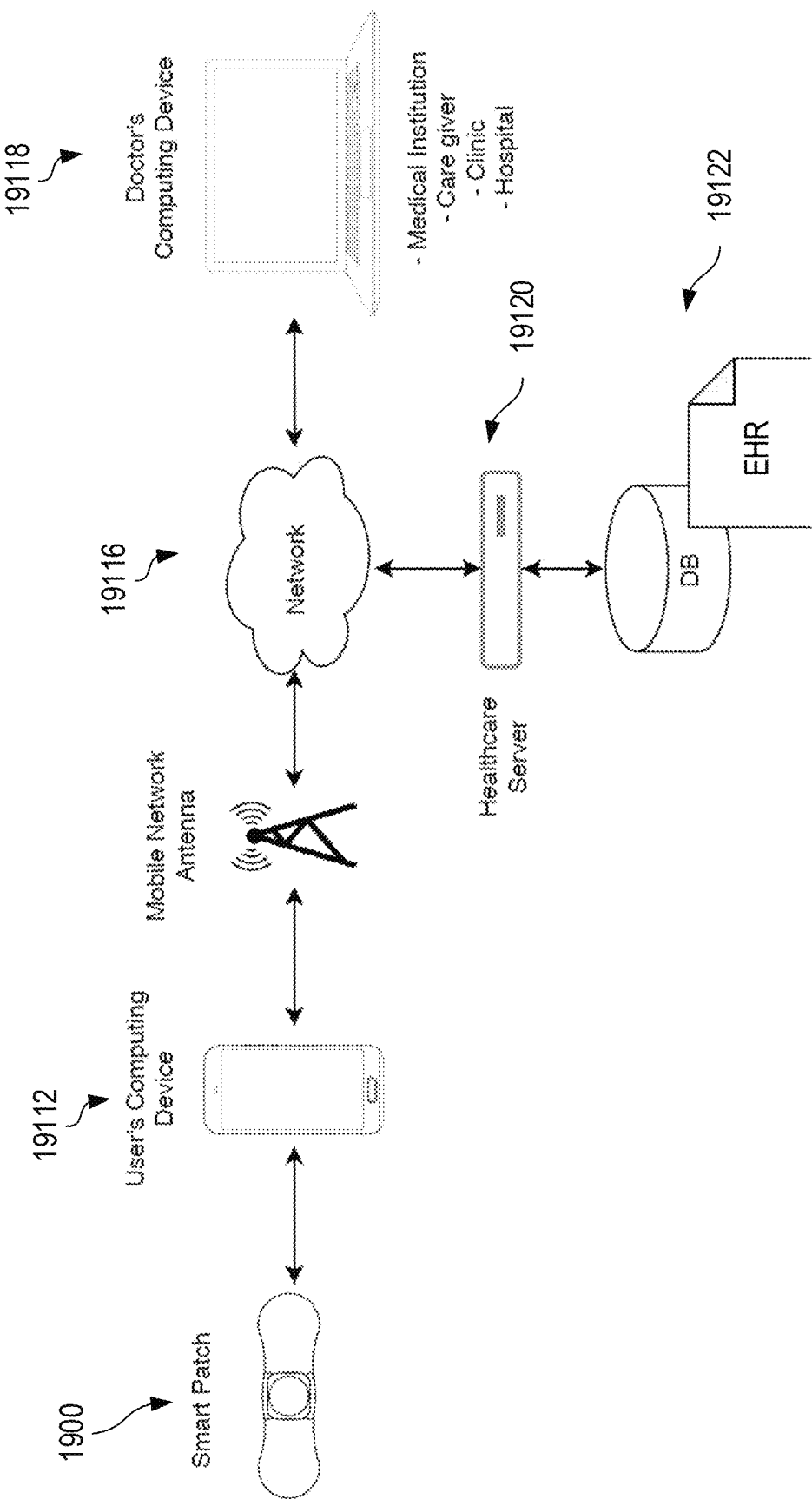
FIG. 19A is a schematic diagram depicting a smart patch connecting to a network via a computing device in a computing environment, according to certain aspects of the present disclosure.

FIG. 19A is a schematic diagram depicting a smart patch 1900 connecting to a network 19116 via a computing device 19112 in a computing environment, according to certain aspects of the present disclosure. Smart patch 1900 can be any suitable smart patch, such as smart patch 600 of FIG. 6.

The smart patch 1900 can be communicatively coupled to a computing device 19112, such as a user's computing device (e.g., smartphone, tablet, laptop, computer, or the like). The computing device 19112 uses a communication interface to wirelessly send and/or receive data. The smart patch's communication interface may support bi-directional wireless data transfer. In some cases, the communication interface may be utilized just to send data whereas in other embodiments, besides transmitting data, the communication interface may also receive data remotely (e.g., updates to OS, firmware, security keys, ML models, algorithms, settings, commands to activate specific sensors that are not always on, etc).

The diagram of FIG. 19A outlines a communications data flow for how information from the smart patch 1900 can be transmitted to a healthcare server 19120 and then stored in a patient's electronic health record (EHR) 19122 for access by a clinician. The smart patch 1900 is attached to the chest area of the user and is configured to capture data (e.g., physiological data, activity data, location data, and environment data) via its integrated sensors.

A computing device (e.g. a smartphone) 19112 is paired with the smart patch 1900 using BLE or another suitable protocol. The computing device 19112 can communicate to the network 19116 over a wireless interface such as BLE, WiFi, mobile network, or the like. As long as the smart patch 1900 and the smartphone are wirelessly connected, all of the sensor data from the smart patch 1900 can be streamed to the mobile device. Using a compatible mobile application installed on the smartphone, the user is able to see and manage their health metrics.

The smartphone application can securely transmit the data captured/generated by the smart patch over a communications network 19116 (e.g., a LAN, PAN, WAN, mobile network, and/or the Internet) to a healthcare server 19120. The data is then stored in the user's Electronic Health Record (EHR) 19122 within a database system. The user's EHR 19122 may contain other health and personal information not acquired from the smart patch 1900 (e.g., physician notes from clinic visits, information about prescribed medications and doses, vaccination records, lab reports, diagnostic imaging records, family medical history, genetic information, gut microbiome analysis, etc).

The healthcare server 19120 can include a medical knowledge graph learned algorithmically from the EHRs 19122 and a corpus of medical information that includes scientific papers published in academic journals, textbooks, manuals, public health data, and data from other sources. The medical knowledge graph can learn relationships between diseases and symptoms across all these sources, which can be leveraged by the AI engine to generate inferences about the user's health state and make predictions about the user's health trajectory. These predictions can serve as a diagnostic tool for clinicians to make more timely decisions about patient care.

The medical knowledge graph can assume a bipartite graph, in which facts are represented as relations (edges) between entities (nodes). Resource Description Framework (RDF) is a common way of representing knowledge graphs. RDF defines relationships in the form of triplets comprising head entity, relation, and tail entity (h, r, t). The medical knowledge graph is clinically useful in understanding the complex relationships between physiological data, symptoms, diseases, biochemistry, pharmacology, genomics, environment data and other dimensions. The medical knowledge graph can be used to find correlations and provide automated recommendations for clinicians while treating patients. The medical knowledge graph may be a system of interacting and interlinked information networks. The content of the medical knowledge graph can also assume a multipartite graph structure that can provide very specific insights and recommendations to clinicians/researchers.

The healthcare server 19120 can include an AI engine that provides predictive insights on patient conditions. The AI engine continually processes the user's EHR 19122, including the data acquired from the smart patch 1900, using AI/machine learning algorithms. The AI engine uses the medical knowledge graph to identify anomalies in the user's EHR 19122, generate inferences about the user's health state, and make predictions about the user's health trajectory.

The AI engine uses a library of algorithms for generating predictions/inferences based on structured and unstructured medical data in the EHR 19122 and medical knowledge graph. A wide range of ML approaches such as CNN (Convolutional Neural Networks), RNN (Recurrent Neural Networks), AutoEncoders, Deep Learning, DanQ, etc. can be used individually or in combination for processing EHR 19122 and knowledge graph data. Trained models can enable high-accuracy detection of health conditions/states with minimal errors. These generated predictions/insights generated by the AI engine can support clinicians in their decision making and allow them to deliver more timely and accurate treatment by providing access to predictive insights, relevant patient information, and pertinent medical knowledge related to the patient's condition.

The healthcare server 19120 can triage predictions from the AI engine using a scoring system which determines how urgently the patient may need healthcare provider attention (e.g., emergency condition or lower priority situation). The health inferences, together with the triage score, may be used by the healthcare server 19120 to automatically initiate a command to the smart patch 1900 over the network 19116 to update settings (e.g., sensor sampling rates) or issue commands (e.g., activate a specific sensor for a specified duration for continuous sampling in order to collect additional data).

The triage scores can also be used by the healthcare server 19120 to provide notifications about a user's health state to a clinician's computing device 19118 (e.g., smartphone, tablet, computer, and the like). These notifications, along with the triage score, allow the physician to address the highest priority cases requiring urgent attention first. For example, a physician may receive a notification indicating that a user suffered a serious drop in blood oxygen saturation which requires immediate attention. The physician can then access real-time data from the user's smart patch 1900 through the healthcare server 19120. The physician can view a dashboard that shows all the patient's real-time vitals. Since the patch functions as an auscultation device by utilizing the integrated ACM units, the physician can also remotely listen to the patient's real-time cardiac and pulmonary sounds on his/her computing device 19118.

Through an application or web interface on the physician's computing device 19118, the physician may also directly communicate with the smart patch 1900 to update settings (e.g., sensor sampling rates) or issue commands (e.g., to activate a specific sensor for a specified duration if it is not continuously sampling data by default).

In other cases, the physician may issue a command to the smart patch 1900 through the healthcare server 19120 that instructs the smart patch 1900 to complete an invasive test using integrated microneedles and a lab-on-chip assembly. In some cases, the physician may issue a command to the smart patch 1900 to initiate treatment using onboard medicines, such as via transdermal drug delivery. In some cases, transdermal drug delivery can be implemented by integrating a microfluidic architecture with microneedles that enable fluid management for transdermal treatment delivery.

These examples highlight the ability for the smart patch 1900 to bi-directionally communicate with other devices over a network 19116. The smart patch 1900 can employ end-to-end data encryption to secure all communication with any other device (smartphone, healthcare server, physician's computing device, etc).

Figure 19B:
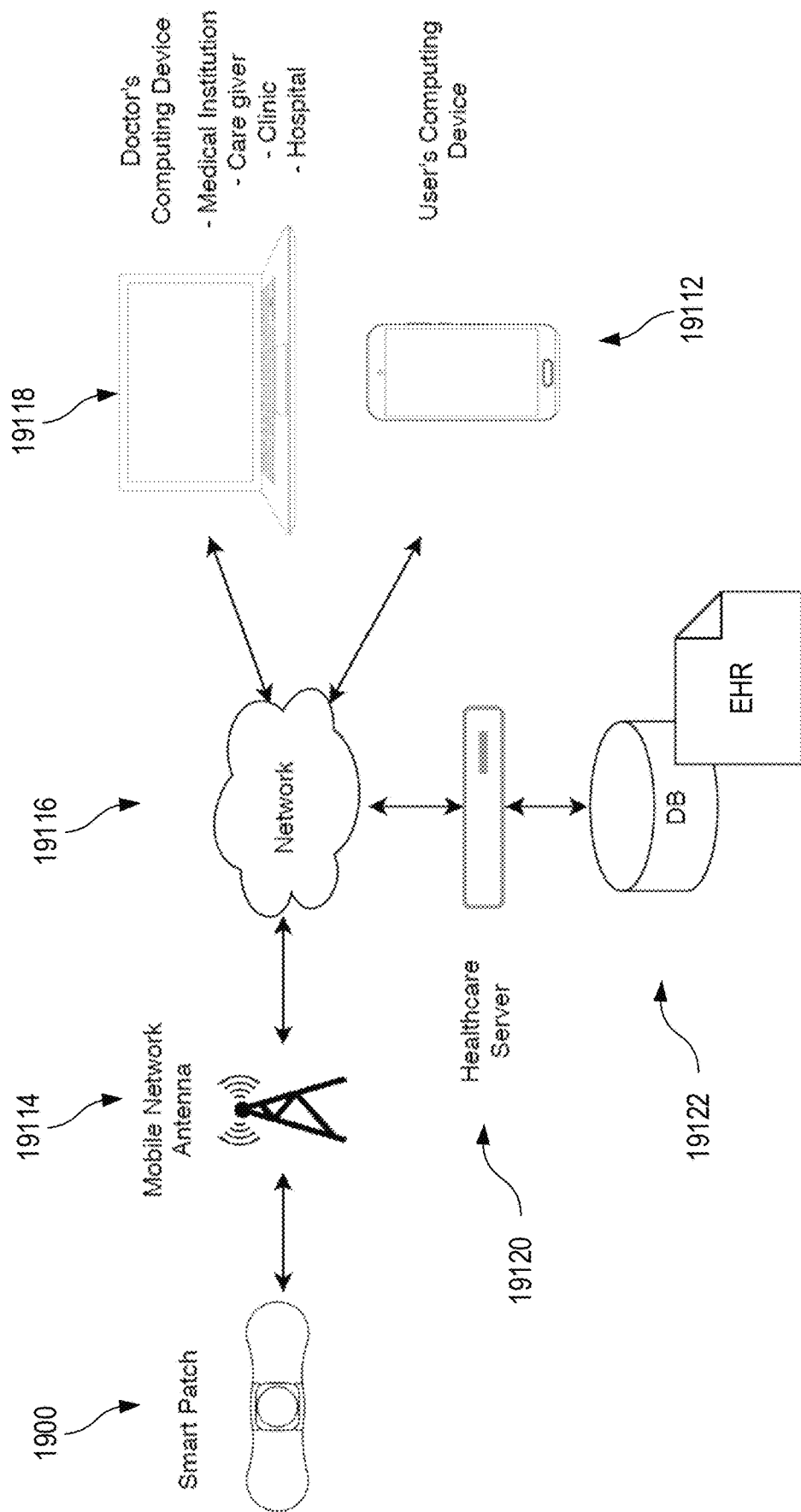
FIG. 19B is a schematic diagram depicting a smart patch of FIG. 19A in use within the computing environment in an alternate fashion, according to certain aspects of the present disclosure.

FIG. 19B is a schematic diagram depicting smart patch 1900 of FIG. 19A in use within the computing environment in an alternate fashion, according to certain aspects of the present disclosure. In some cases, smart patch 1900 can connect directly to a network 19116 via its mobile network radio and antenna. This direct connection allows the smart patch 1900 to continuously stream sensor data to a healthcare server 19120 for storage in the user's EHR 19122 contained in a database system. The integrated mobile network radio in the electronics module obviates the need for the smart patch 1900 to communicate with the healthcare server 19120 through computing device 19112 (e.g., a user's smartphone) or other wireless computing devices as illustrated in FIG. 19A.

In FIG. 19B, the user's computing device 19112 can include an accompanying mobile health application installed which allows the user to securely access and/or synchronize data in their EHR 19122 from the healthcare server.

The mobile health application can allow patients to aggregate their health records from multiple institutions alongside their patch-generated data, creating a more holistic view of their health. The mobile health application can leverage OAuth 2.0, which allows users to authenticate with other health provider systems once and create an enduring connection to their respective EHR 19122. The mobile health application can periodically connect to the EHR 19122 to pull in any new health records and notify the user when new records are available. The connection between the various distributed EHRs 19122 and a user's mobile health application can utilize FHIR (Fast Healthcare Interoperability Resources) standard APIs as defined by the Argonaut Project. FHIR allows the mobile health application to aggregate health records from different providers in a standardized way for secure viewing and storage on the user's smartphone. All health data can be protected by an encrypted, direct connection when moving data between the smartphone and EHR provider APIs.

An API for the mobile health application allows developers of fitness and health apps for smartphones and smartwatches to access user data on the mobile health application in order to create a central data store for user fitness/health data.

All health data stored on the smartphone and accessible via the mobile health application can be encrypted and further protected by application-level and device-level authentication (e.g., password, PIN, face authentication, fingerprint authentication, voice authentication, etc).

The mobile health application may show a real-time dashboard of the patient's vitals being captured from the smart patch 1900, EHRs 19122 at multiple providers (with information related to allergies, conditions, immunizations, lab results, diagnostic imaging records, genetic records, microbiome analysis, medications, procedures, vitals, wellness summaries), cross-patient benchmarks, personalized recommendations (nutrition, fitness regime, mental wellbeing), health alerts, a message center for communicating with physicians/care teams, etc.

The mobile health application can include functionality to synchronize data captured from multiple EHRs 19122 and other mobile applications with the healthcare server 19120. This synchronization allows for cloud storage of the patient's aggregate health information, including the patch data. All the user's health data centrally stored in the user's EHR 19122 can then be processed and analyzed on a continual basis by the healthcare server's AI engine.

Figure 20:
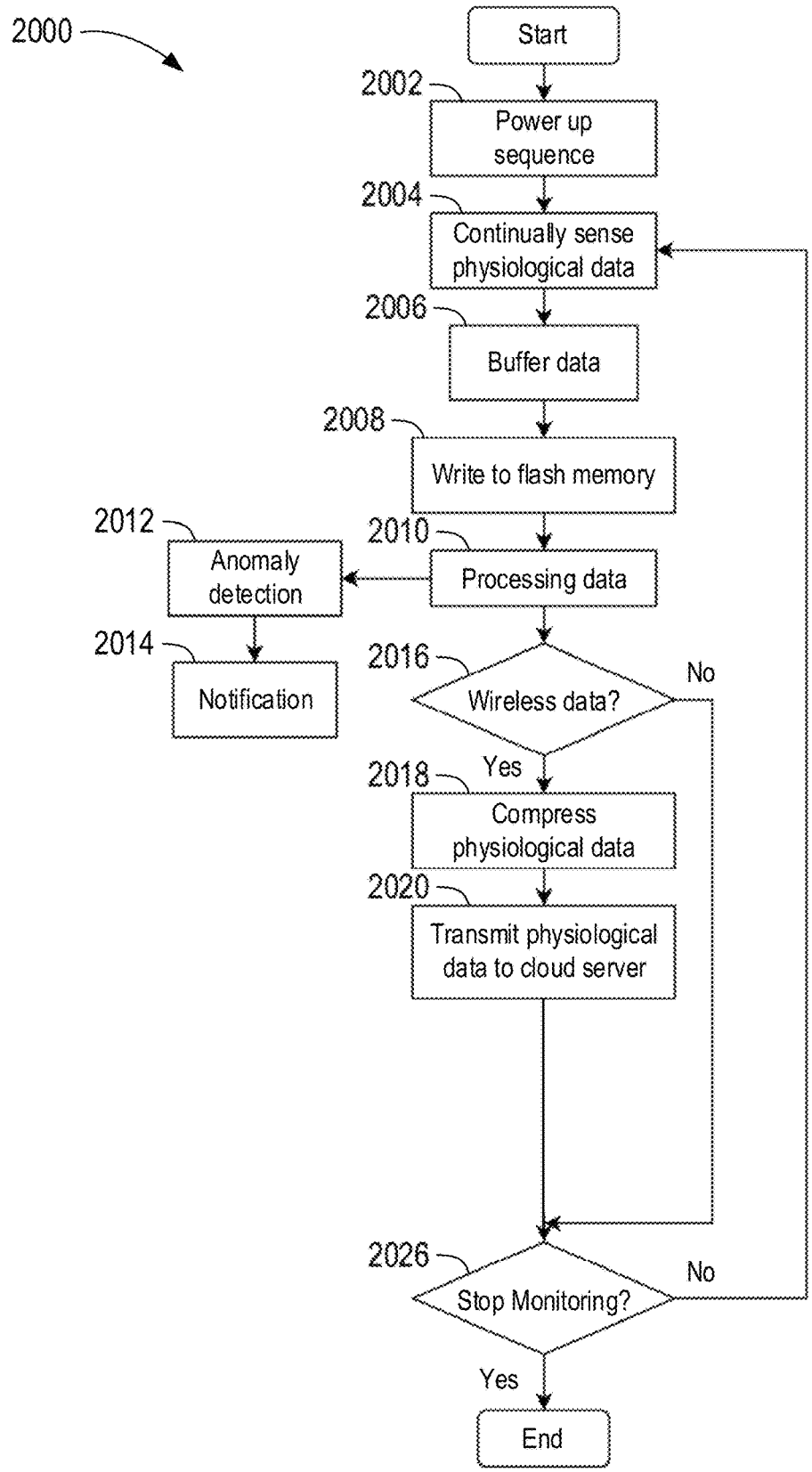
FIG. 20 is a flowchart depicting a functioning process of a smart patch, according to certain aspects of the present disclosure.

FIG. 20 is a flowchart depicting a functioning process 2000 of a smart patch, according to certain aspects of the present disclosure. Process 2000 can be performed by any suitable smart patch, such as smart patch 600 of FIG. 6.

Process 2000 outlines the steps by which physiological data is acquired by the smart patch, stored, processed and transmitted to a server. Initially, the electronics module is inserted into the flexible patch's receptacle. Once the electronics module is snap-fitted into the receptacle and upon being connected to the set of pads provided in the receptacle, the microcontroller can automatically execute a full power-up sequence at block 2002. The power-up sequence can be automatically executed upon detection of a small resistance measured from the hydrogel electrodes. In some cases, a power-up sequence can be user-triggered, such as via a user interface of the electronics module (e.g., a button or other actuatable sensor on the electronics module) or a user interface of a user device (e.g., an electronic button on an app used to control the smart patch). During the power-up sequence, the microcontroller operation is diagnostically confirmed, the voltage of the battery is checked, the state of the flash memory is confirmed (e.g., operability check, available capacity, etc), and the instructions for the sensor's data acquisition/processing are provided to the CPU. Furthermore, the status of all sensors is confirmed, all sensors are calibrated, and the connection between the electrode contacts in the patch with the skin is confirmed. In some cases, a wireless connection (e.g., network connection) can be automatically established.

Following the satisfactory completion of the power-up sequence at block 2002, an iterative processing loop can be continually executed by the microcontroller, in which raw physiological data is acquired via the sensors and processed. At block 2004, the smart patch can continuously sense physiological data, such as using any of the various sensors disclosed herein. Sampled physiological signals are quantized, digitized, and temporarily staged in a buffer at block 2006 pending conditioning/filtering and compression.

Following compression, the compressed digitized sample is again buffered, then written to the flash memory at block 2008 using the communications bus. Data stored in the flash memory can be processed at block 2010 using quantized and compressed AI models operating on-device. The AI Accelerator enables a sensor fusion approach to data processing. The AI Accelerator may process data captured from individual sensors. The AI Accelerator may also process data captured from multiple sensors using multimodal machine learning (ML) models that infer health information using a broader set of data than typically possible by drawing inferences from single sensor data. The AI Accelerator may also be used to handle speech recognition, speech synthesis, and other supported features of the smart patch device. The on-device machine learning models are trained in the cloud and uploaded to the patch wirelessly from the healthcare server. New models enable on-device health monitoring/detection capabilities.

When processing the data at block 2010, the CPU/AI Accelerator can use on-device algorithms and ML models to detect health anomalies at block 2012 (e.g., detect a change in the user's health state, abnormal changes in health vitals, inferred medical conditions, etc).

In some cases, data processing can continue as long as the electronics module remains connected to the flexible patch, the smart patch is on the user's chest acquiring data and there is free storage space in flash memory. In some cases, data processing can continue until a command is received (e.g., from a user device) to stop (e.g., a stop recording command). Processing can also continue as long as there is remaining battery charge. If these requirements are not met, the processing loop can terminate. Still other operations and steps are possible. In some cases, data processing on already collected data can continue occurring after the electronics module is removed from the flexible patch or the flexible patch is removed from the user.

Anomalies detected at block 2012 can be used to trigger notifications to the user and/or the physician/care team at block 2014. For example, the smart patch may initiate a notification to the user's smartphone that is wirelessly connected to the patch. The smart patch may also initiate notifications to the physician's network-connected computing device (e.g., smartphone, tablet, computer) through the healthcare server. This may, for example, result in the physician receiving a notification (push notification, SMS, pager notification, and the like) on the physician's computing device (e.g., smartphone) which provides patient information (e.g., name, contact phone number), health anomaly (e.g., low blood oxygen saturation), and a triage score (emergency or low priority). The physician can click on the mobile notification, which launches a mobile application that instantly shows real-time patient vitals, and optionally historical vitals, from the user's smart patch and/or the healthcare server. In some cases, the smart patch can provide alerts to the user, such as in the form of sounds, lights, vibrations, or the like.

As described in further detail herein, the smart patch may be configured to wirelessly transmit data to a connected device, including a smartphone, healthcare server, or other network connected computing device. Data that may be transmitted from the smart patch includes raw sensor data, health metrics, inferred health states/conditions, generated data, systems data, etc. At block 2016, the process 2000 can determine whether the smart patch is wirelessly connected to another computing device to which it needs to transfer its data. If not, the smart patch can proceed at block 2026 by determining whether or not to stop monitoring. If monitoring is to stop, process 2000 can conclude. If monitoring is not to stop, process 2000 can continue back to block 2004.

If the smart patch is to transmit wireless data as determined at block 2016, the physiological data can undergo compression at block 2018 before being transferred (e.g., to a cloud-based healthcare server) at block 2020. The data compression step makes it more efficient to transfer wirelessly.

Upon receiving the data, the healthcare server can decompress the data, before it is stored in a database which includes the user's EHR. The user's EHR may be continually updated with data from his/her smart patch along with other sources of user health information.

Other variations of process 2000 can be used, including with more or fewer blocks, as well as blocks in other orders.

Figure 21:
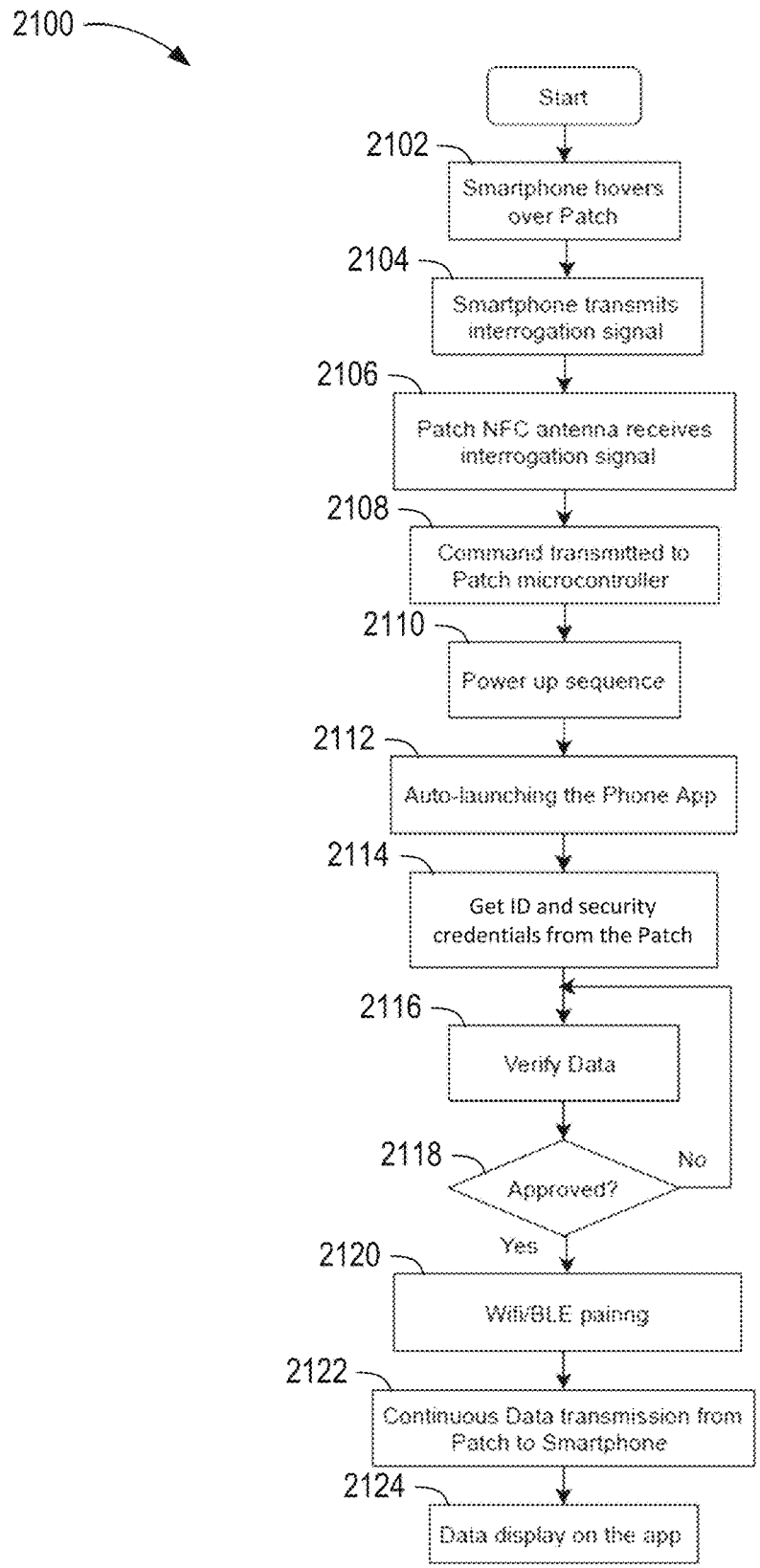
FIG. 21 is a flowchart depicting a process for using a computing device wirelessly connected with a smart patch, according to certain aspects of the present disclosure.

FIG. 21 is a flowchart depicting a process 2100 for using a computing device wirelessly connected with a smart patch, according to certain aspects of the present disclosure. Process 2100 can be performed by any suitable computing device and smart patch, such as computing device 19112 and smart patch 1900 of FIGS. 19A-19B. While described with reference to a smartphone with reference to FIG. 21, process 2100 can occur between a smart patch and any suitable computing device.

At block 2102, a smartphone having an NFC interface is placed in close proximity to the top of the smart patch's electronics module. The close proximity of the devices, and their respective NFC interfaces, results in the smartphone's NFC interface transmitting an interrogation signal at block 2104. The smart patch's NFC interface receives the interrogation signal at block 2106, which triggers a message to the microcontroller at block 2108 to initiate the power-up sequence. The electronics module initiates the power-up sequence at block 2110.

Upon receiving a message with the application ID at the smartphone NFC interface, the application ID is used by the smartphone microcontroller to identify and automatically launch the mobile health application for the smart patch at block 2112. In the event the application is not already installed on the smartphone at the time of the NFC exchange, the received message with the application ID launches the application store (e.g., Apple App Store, Google Play Store, etc.) and automatically displays the health application download page. In some cases, the health application simply auto-downloads to the smartphone if not already installed at the time of the NFC data exchange between the smartphone and smart patch.

To complete the BLE pairing process, at block 2116 the smartphone app verifies the patch device ID, security credentials, and other information received during the NFC exchange. If the information is not verified (e.g., approved) at block 2118, verification can be performed again or other actions can be taken to obtain verifiable credentials or determine why the credentials were not verified. After the information is verified at block 2118, the devices establish a WiFi or BLE connection at block 2120 and the smart patch's communications profile is saved on the smartphone for future use.

At block 2120, while the smartphone and smart patch are still in close proximity and communicating over the established NFC session, the smartphone initiates a WiFi or BLE pairing request and receives customary WiFi or BLE pairing response messages back to initiate the wireless link. In some cases, instead of WiFi or BLE, other wireless communication standards could be used for pairing the patch and a computing device. The smart patch NFC interface also transmits messages to the smartphone NFC interface containing an application ID (associated with its smartphone app), patch device ID, patch security credentials (e.g., a security key to enable encrypted communication over the wireless link), and other information at block 2114.

When the smart patch and smartphone are connected via a wireless link, the patch electronics module transmits data continuously to the smartphone at block 2122 when within wireless range. When not in range, the smart patch may store all the user data for automatic transmission to the smartphone when they come back within WiFi or BLE range.

The NFC data exchange may be performed in accordance with the NFC Forum's Technical Specifications. Other NFC/RFID data formats could be similarly used to perform the same operations. Also, while the steps outlined mentioned WiFi or BLE pairing, the same or similar techniques could be used to establish a wireless communications link over Bluetooth, WiFi, ZigBee, Thread, Z-Wave, or other wireless communication standards.

At block 2124, the smartphone can display data from the smart patch. The health application on the smartphone is capable of receiving all the patch data, displaying a dashboard of real-time health metrics, processing the data using algorithms or on-device ML models associated with the application, providing health recommendations (e.g., nutrition, exercise, activity, mental wellbeing, sleep, etc), notifications (e.g., changes in health metrics), and a messaging center for communicating with healthcare teams. The health application on the phone may also receive health data from other wearable devices connected to the smartphone (e.g., smartwatches, bracelets, smart running shoes, earpods, headphones, smart rings, smart glasses, etc) and provide the user with access to his/her EHR which may reside within the application or be mirrored in the cloud and accessed via the healthcare server. The healthcare application may process data from multiple sources and display reports and visualizations of real-time data received from multiple sources.

Other variations of process 2100 can be used, including with more or fewer blocks, as well as blocks in other orders.

Figure 22:
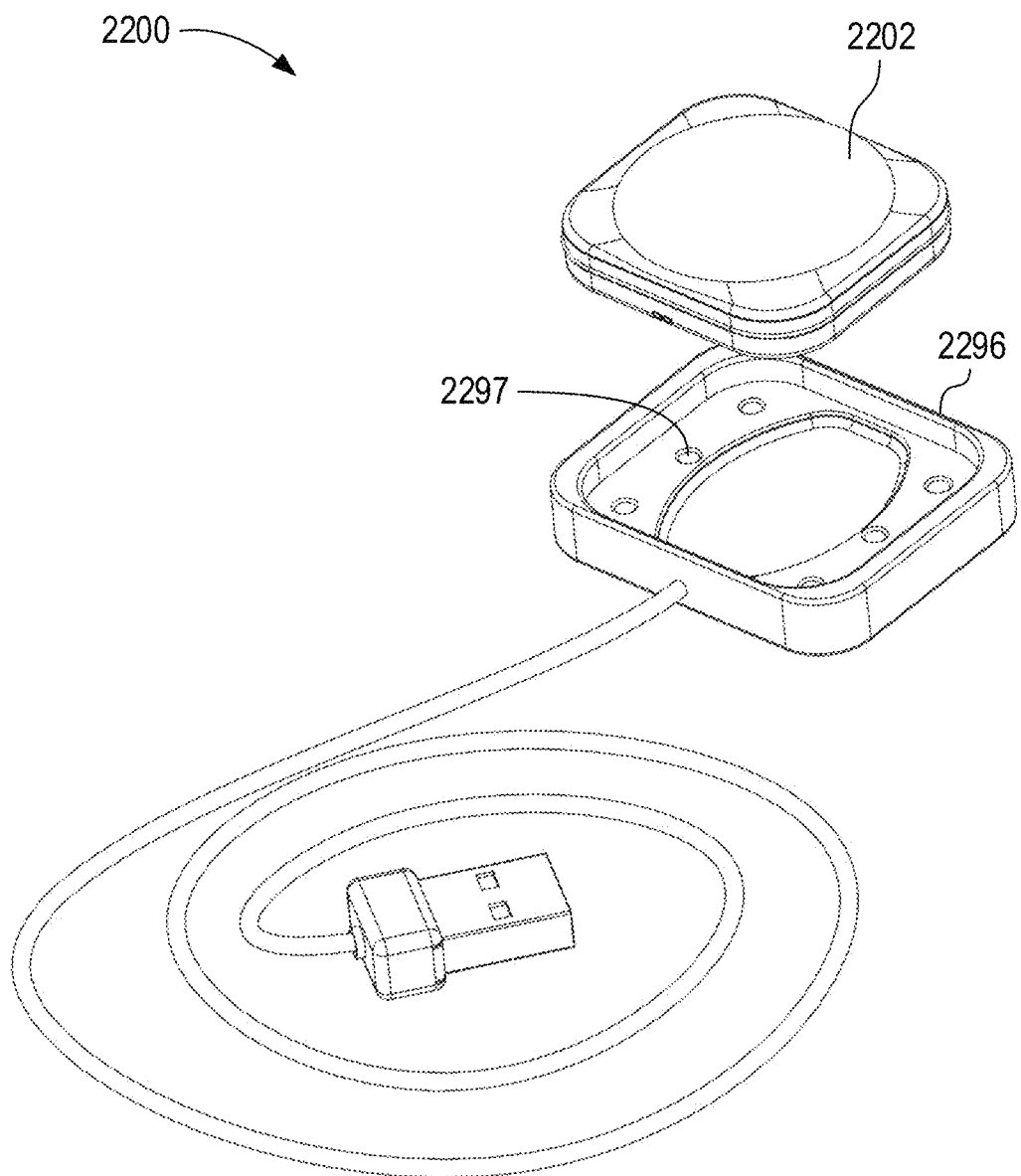
FIG. 22 is a graphical projection of an electronics module being placed into a charging device, according to certain aspects of the present disclosure.

FIG. 22 is a graphical projection of an electronics module 2202 being placed into a charging device 2296, according to certain aspects of the present disclosure. Electronics module 2202 can be any suitable electronics module, such as electronics module 102 of FIG. 1.

When the electronics module 2202 needs to be charged, it can be removed from the flexible patch's receptacle and be placed in the charging device 2296 (e.g., charger dock). The electrode contacts at the bottom of the electronics module 2202 come in contact with corresponding charging contacts 2297 on the base of the charging device 2296. As previously mentioned, the electronics module 2202 can use the six electrode contacts on its bottom surface for ECG and bioimpedance measurements, as well as for charging its battery by harvesting power via the charging device 2296.

The disclosed charging device 2296 can draw power from a power source through a USB connector or other suitable connector that carries the current to the charging device (e.g., via a wire). The transmitted power arrives at the charging device 2296 where detectors and rectifiers modify the current before it is sent towards the charging device's charging contacts 2297 that conductively interface with the electrodes of the electronics module 2202, thereby transmitting power from the charger to the battery of the electronics module 2202. This design allows for rapid and convenient charging of the battery of the electronics module 2202.

In some cases, the electronics module 2202 can still perform certain operations when on the charging device 2296 and being charged. For example, the electronics module 2202 can still provide feedback in the form of visual and/or audio feedback, such as to indicate charging status and/or provide other useful information. In some cases, the electronics module 2202 can still perform voice assistant type commands while on the charging device 2296, such as to record timestamped events and/or respond to inquiries about charging status.

The electronics module 2202 may also support wireless charging using NFC or over-the-air wireless charging technologies, as disclosed in further detail herein. Other formats of charging devices 2296 can be used, such as charging devices capable of charging multiple electronics modules at the same time. In some cases, the electronics module 2202 can snap-fit into the charging device 2296, similar to how the electronics module 2202 snap-fits into the receptacle of the flexible patch, although that need not always be the case. In some cases, the electronics module 2202 merely rests upon the charging device 2296.

Figure 23:
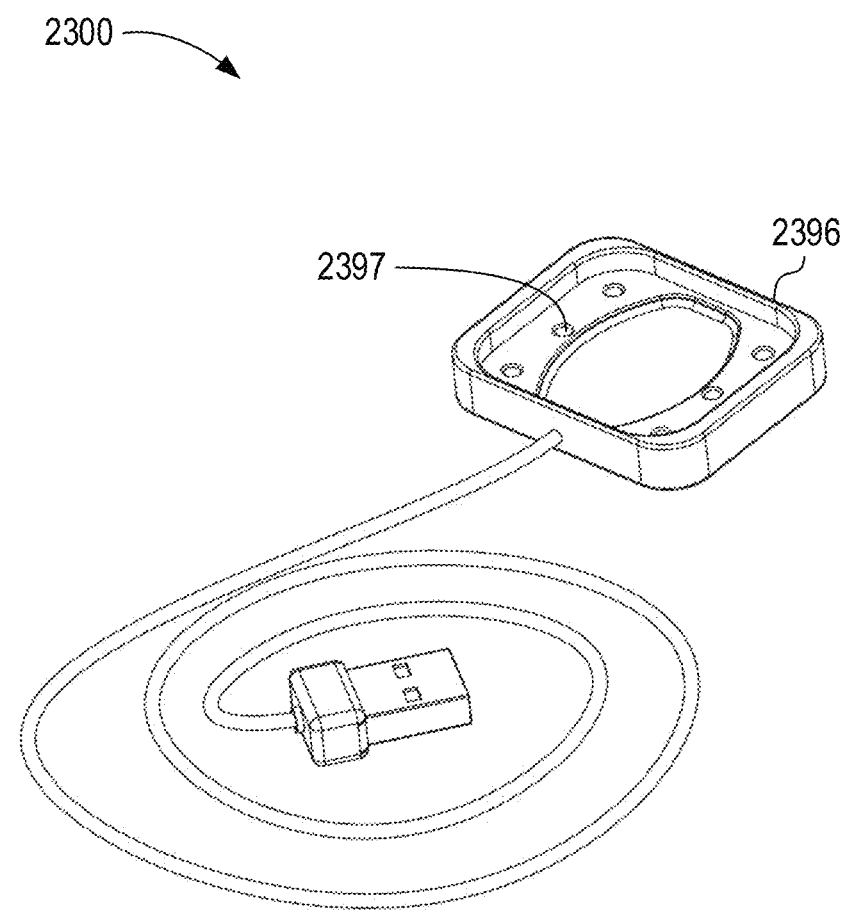
FIG. 23 is a graphical projection of a charging device, according to certain aspects of the present disclosure.

FIG. 23 is a graphical projection of a charging device 2396, according to certain aspects of the present disclosure. Charging device 2396 can be charging device 2296 of FIG. 22.

The charging contacts 2397 can be recessed in the base of the charging device 2396 so that the six electrodes protruding from the bottom of the electronics module can mate without obstruction when the module is inserted for charging. The base of the charging device 2396 can also have a recessed cavity designed to house the electronics module's protruding sensor window, temperature/humidity sensor, and/or ACM units. All the recessed areas of the charging device 2396 can be positioned to ensure that the electronics module's electrodes can make contact with the charging contacts 2397 without interference when the electronics module is placed in the charging device 2396 for charging.

The foregoing description of the embodiments, including illustrated embodiments, has been presented only for the purpose of illustration and description and is not intended to be exhaustive or limiting to the precise forms disclosed. Numerous modifications, adaptations, and uses thereof will be apparent to those skilled in the art. Numerous changes to the disclosed embodiments can be made in accordance with the disclosure herein, without departing from the spirit or scope of the invention. Thus, the breadth and scope of the present invention should not be limited by any of the above-described embodiments.

Although the invention has been illustrated and described with respect to one or more implementations, equivalent alterations and modifications will occur or be known to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

As used below, any reference to a series of examples is to be understood as a reference to each of those examples disjunctively (e.g., "Examples 1-4" is to be understood as "Examples 1, 2, 3, or 4").

Example 1 is a wearable auscultation device, comprising: an electronics module positionable against skin of a user, the electronics module comprising: a plurality of accelerometer contact microphone (ACM) units positioned in a planar array, each ACM unit having a sensing surface, wherein each ACM unit of the array is spaced apart from each other ACM unit of the array, and wherein the sensing surface of each ACM unit of the planar array is coplanar; and electronic components for receiving and processing signal data from each of the ACM units; wherein, when the electronics module is positioned against the skin of the user, the sensing surface of each ACM unit is contacting the skin of the user.

Example 2 is the device of example(s) 1, further including an attachment module for securing the electronics module against the skin of the user, Example 3 is the device of example(s) 2, wherein the attachment module comprises an adhesive layer couplable to the skin of the user.

Example 4 is the device of example(s) 2 or 3, wherein the attachment module comprises a receptacle for releasably securing the electronics module to the attachment module.

Example 5 is the device of example(s) 1-4, wherein the electronics module comprises a rechargeable battery.

Example 6 is the device of example(s) 1-5, wherein the plurality of ACM units includes a first ACM unit, a second ACM unit, and a third ACM unit; and wherein a line extending through the first ACM unit and the second ACM unit intersects a line extending through the second ACM unit and the third ACM unit.

Example 7 is the device of example(s) 6, wherein the line extending through the first ACM unit and the second ACM unit intersects the line extending through the second ACM unit and the third ACM unit at a 90° angle.

Example 8 is the device of example(s) 1-7, wherein the electronics module further comprises at least one light-emitting diode (LED) positioned to direct light towards a face of the user when the electronics module is positioned against the skin of the user at a chest of the user.

Example 9 is the device of example(s) 1-8, wherein each of the ACM units includes a microelectromechanical system (MEMS) accelerometer coupled to an application-specific integrated circuit (ASIC) in a stacked configuration such that the sensing surface of the MEMS accelerometer is positioned between the skin of the user and the ASIC when the electronics module is positioned against the skin of the user.

Example 10 is the device of example(s) 1-8, wherein each of the ACM units includes a microelectromechanical system (MEMS) accelerometer coupled to an application-specific integrated circuit (ASIC) in a parallel configuration such that a plane parallel to the sensing surface passes through both the MEMS accelerometer and the ASIC.

Example 11 is the device of example(s) 1-10, wherein the electronic components comprise: one or more data processors; and a non-transitory computer-readable storage medium containing instructions which, when executed on the one or more data processors, cause the one or more data processors to perform operations including: receiving an ACM signal from each of the plurality of ACM units, wherein the ACM signals are associated with a sound from within the user; synchronizing each of the ACM signals; and reducing noise or motion artifacts associated with at least one of the synchronized ACM signals using at least another of the synchronized ACM signals.

Example 12 is the device of example(s) 11, wherein the operations further comprise determining a source location for the sound using the synchronized ACM signals.

Example 13 is the device of example(s) 12, wherein the operations further comprise outputting cardiopulmonary information based on the determined source location and the synchronized ACM signals.

Example 14 is the device of example(s) 12 or 13, wherein the operations further comprise: determining a location of the electronics module with respect to the user; and determining a location of the sound with respect to the electronics module, wherein determining the source location for the sound includes using the location of the electronics module with respect to the user and the location of the sound with respect to the electronics module to determine a location of the sound with respect to the user.

Example 15 is the device of example(s) 11-14, wherein the operations further comprise filtering the ACM signals, wherein filtering the ACM signals includes identifying the sound as a cardiopulmonary sound.

Example 16 is the device of example(s) 15, wherein identifying the sound as a cardiopulmonary sound includes identifying the sound as a heart sound or a lung sound.

Example 17 is the device of example(s) 11-15, wherein the operations further comprise: receiving inertial measurement unit data, and determining a source location for the sound using the synchronized ACM signals and the inertial measurement unit data.

Example 18 is the device of example(s) 11-17, wherein receiving the ACM signal from each of the plurality of ACM units occurs while the electronics module is secured to the skin of the user.

Example 19 is a computer-implemented method, comprising: supplying power to a plurality of accelerometer contact microphone (ACM) units positioned in a planar array within an electronics module positionable against skin of a user, each ACM unit having a sensing surface, wherein each ACM unit of the array is spaced apart from each other ACM unit of the array, and wherein the sensing surface of each ACM unit of the planar array is coplanar; receiving an ACM signal from each of the plurality of ACM units, wherein the ACM signals are associated with a sound from within the user, and wherein receiving the ACM signal from each of the plurality of ACM units occurs while the electronics module is positioned against the skin of the user; synchronizing each of the ACM signals; and reducing noise or motion artifacts associated with at least one of the synchronized ACM signals using at least another of the synchronized ACM signals.

Example 20 is the method of example(s) 19, further comprising determining a source location for the sound using the synchronized ACM signals.

Example 21 is the method of example(s) 20, further comprising outputting cardiopulmonary information based on the determined source location and the synchronized ACM signals.

Example 22 is the method of example(s) 20 or 21, further comprising: determining a location of the electronics module with respect to the user; and determining a location of the sound with respect to the electronics module, wherein determining the source location for the sound includes using the location of the electronics module with respect to the user and the location of the sound with respect to the electronics module to determine a location of the sound with respect to the user.

Example 23 is the method of example(s) 19-22, further comprising filtering the ACM signals, wherein filtering the ACM signals includes identifying the sound as a cardiopulmonary sound.

Example 24 is the method of example(s) 23, wherein identifying the sound as a cardiopulmonary sound includes identifying the sound as a heart sound or a lung sound.

Example 25 is the method of example(s) 19-24, further comprising: receiving inertial measurement unit data, and determining a source location for the sound using the synchronized ACM signals and the inertial measurement unit data.

Example 26 is the method of example(s) 19-25, wherein the plurality of ACM units includes a first ACM unit, a second ACM unit, and a third ACM unit; and wherein a line extending through the first ACM unit and the second ACM unit intersects a line extending through the second ACM unit and the third ACM unit.

Example 27 is the method of example(s) 26, wherein the line extending through the first ACM unit and the second ACM unit intersects the line extending through the second ACM unit and the third ACM unit at a 90° angle.

Example 28 is the method of example(s) 19-27, wherein the electronics module further comprises at least one light-emitting diode (LED) positioned to direct light towards a face of the user when the electronics module is positioned against the skin of the user at a chest of the user.

Example 29 is the method of example(s) 19-28, wherein each of the ACM units includes a microelectromechanical system (MEMS) accelerometer coupled to an application-specific integrated circuit (ASIC) in a stacked configuration such that the sensing surface of the MEMS accelerometer is positioned between the skin of the user and the ASIC when the electronics module is positioned against the skin of the user.

Example 30 is the method of example(s) 19-29, wherein each of the ACM units includes a microelectromechanical system (MEMS) accelerometer coupled to an application-specific integrated circuit (ASIC) in a parallel configuration such that a plane parallel to the sensing surface passes through both the MEMS accelerometer and the ASIC.

Example 31 is a computer-program product tangibly embodied in a non-transitory machine-readable storage medium, including instructions configured to cause a data processing apparatus to perform the method of example(s) 19-30.

Example 32 is a wearable monitoring device, comprising: an electronics module positionable against skin of a user, the electronics module comprising: a printed circuit board (PCB) having a first side facing towards the skin of the user and a second side facing away from the skin of the user; at least one contact sensor coupled to the first side of the PCB, the at least one contact sensor making contact with the skin of the user when the electronics module is positioned against the skin of the user; one or more processors coupled to the second side of the PCB; and at least one memory coupled to the second side of the PCB.

Example 33 is the wearable monitoring device of example(s) 32, wherein the electronics module further comprises at least one environmental sensor coupled to the first side of the PCB.

Example 34 is the wearable monitoring device of example(s) 32 or 33, wherein the at least one contact sensor includes an accelerometer contact microphone (ACM) unit.

Example 35 is the wearable monitoring device of example(s) 32-34, wherein the at least one environmental sensor includes an insulation wall that makes contact with the skin of the user when the electronics module is positioned against the skin of the user, and wherein the insulation wall, the environmental sensor, and the skin define an enclosed environment when the electronics module is positioned against the skin of the user.

Example 36 is the wearable monitoring device of example(s) 32-35, wherein the electronics module further comprises: a divider positioned opposite the PCB from the at least one contact sensor; and an electromagnetic component coupled to the PCB and positioned opposite the divider from the PCB.

Example 37 is the wearable monitoring device of example(s) 36, wherein the electromagnetic component includes an antenna for wireless communication.

Example 38 is the wearable monitoring device of example(s) 36-37, further comprising a receptacle for receiving the electronics module, the receptacle being securable to the skin of the user, wherein the electronics module comprises one or more interlocking features that engage one or more corresponding interlocking features of the receptacle to removably secure the electronics module within the receptacle.

Example 39 is the wearable monitoring device of example(s) 38, wherein the receptacle includes one or more openings for receiving the at least one contact sensor.

Example 40 is the wearable monitoring device of example(s) 38 or 39, wherein the receptacle is coupled to a flexible patch having an adhesive layer for securing the receptacle to the skin of the user, and wherein the at least one contact sensor extends from the first side of the PCB by a distance suitable to contact the skin of the user when the adhesive layer of the flexible patch secures the receptacle to the skin of the user.

Example 41 is the wearable monitoring device of example(s) 38-40, wherein, when the electronics module is removably secured within the receptacle, a moisture-resistant seal is formed between the electronics module and the receptacle.

Example 42 is the wearable monitoring device of example(s) 32-41, wherein the at least one contact sensor includes a microelectromechanical system (MEMS) accelerometer coupled to an application-specific integrated circuit (ASIC) in a stacked configuration such that a sensing surface of the MEMS accelerometer for contacting the skin of the user is positioned between the skin of the user and the ASIC when the electronics module is positioned against the skin of the user.

Example 43 is the wearable monitoring device of example(s) 32-42, wherein the at least one contact sensor includes a microelectromechanical system (MEMS) accelerometer coupled to an application-specific integrated circuit (ASIC) in a parallel configuration such that a plane parallel to a sensing surface of the MEMS accelerometer for contacting the skin of the user passes through both the MEMS accelerometer and the ASIC.

Example 44 is the wearable monitoring device of example(s) 32-43, wherein the electronics module further includes a plurality of electrode contacts extending from the first side of the PCB.

Example 45 is the wearable monitoring device of example(s) 44, further comprising a receptacle for receiving the electronics module, the receptacle being securable to the skin of the user, wherein the electronics module comprises one or more interlocking features that engage one or more corresponding interlocking features of the receptacle to removably secure the electronics module within the receptacle.

Example 46 is the wearable monitoring device of example(s) 44, further comprising a flexible patch securable to the skin of the user, the flexible patch comprising: a receptacle for receiving the electronics module, wherein the electronics module comprises one or more interlocking features that engage one or more corresponding interlocking features of the receptacle to removably secure the electronics module within the receptacle; a set of electrode pads electrically couplable to the skin of the user when the flexible patch is secured to the skin of the user; and a set of flexible traces connecting the set of electrode pads with the plurality of electrode contacts of the electronics module when the electronics module is removably secured within the receptacle.

Example 47 is the wearable monitoring device of example(s) 32-46, wherein the electronics module further comprises at least one non-contact sensor coupled to the first side of the PCB, wherein the at least one non-contact sensor does not make contact with the skin of the user when the electronics module is positioned against the skin of the user.

Example 48 is the wearable monitoring device of example(s) 47, wherein the at least one non-contact sensor includes an optical sensor.

Example 49 is the wearable monitoring device of example(s) 47 or 48, wherein the at least one non-contact sensor includes an electromagnetic sensor.

Example 50 is the wearable monitoring device of example(s) 48 or 49, wherein the electronics module further comprises a window opening positioned to expose the at least one non-contact sensor to the skin of the user when the electronics module is positioned against the skin of the user.

Example 51 is the wearable monitoring device of example(s) 50, wherein the electronics module further includes a sensor window positioned within the window opening, and wherein the sensor window is translucent or transparent to sensing wavelengths associated with the one or more non-contact sensors.

Example 52 is the wearable monitoring device of example(s) 51, wherein a bottom surface of the sensor window is coplanar with a sensing surface of the at least one contact sensor.

Example 53 is a wearable monitoring device, comprising: an electronics module positionable against skin of a user, the electronics module having a bottom surface comprising: a set of accelerometer contact microphone (ACM) sensors extending outwards from the bottom surface, each of the ACM sensors having a sensing surface for contacting against the skin of the user; a sensor window covering a set of non-contact sensors positioned behind the sensor window, wherein a bottom surface of the sensor window is coplanar with the sensing surfaces of the set of ACM sensors; and a first set of electrode contacts and a second set of electrode contacts extending outwards from the bottom surface, wherein the first set of electrode contacts and second set of electrode contacts are coupled to a printed circuit board (PCB) for conveying electrical signals between the skin of the user and the PCB, and wherein each electrode contact of the first set of electrode contacts is paired with a corresponding electrode contact of the second set of electrode contacts.

Example 54 is the wearable monitoring device of example(s) 53, further comprising a flexible patch securable to the skin of the user, the flexible patch comprising: a receptacle for receiving the electronics module, wherein the electronics module comprises one or more interlocking features that engage one or more corresponding interlocking features of the receptacle to removably secure the electronics module within the receptacle; a set of electrode pads electrically couplable to the skin of the user when the flexible patch is secured to the skin of the user; and a set of flexible traces connecting the set of electrode pads with the plurality of electrode contacts of the electronics module when the electronics module is removably secured within the receptacle.

Example 55 is the wearable monitoring device of example(s) 54, wherein the receptacle includes at least one opening for receiving the set of ACM sensors and the sensor window therethrough when the electronics module is removably secured within the receptacle.

Example 56 is the wearable monitoring device of example(s) 55, wherein the flexible patch includes an adhesive layer for securing the flexible patch to the skin of the user, and wherein the sensing surfaces of the ACM sensors extend from the bottom surface of the electronics module by a distance sufficient to contact the skin of the user when the adhesive layer of the flexible patch secures the flexible patch to the skin of the user.

Example 57 is the wearable monitoring device of example(s) 56, wherein the sensing surfaces of the ACM sensors extend from the bottom surface of the electronics module to a distance of between 1 mm and 4 mm past the adhesive layer when the electronics module is removably secured within the receptacle.

Example 58 is the wearable monitoring device of example(s) 55-57, wherein the at least one opening of the receptacle includes a discrete opening for each of the set of ACM sensors and an additional opening for the sensor window.

Example 59 is the wearable monitoring device of example(s) 53-58, wherein the first set of electrode contacts is positioned opposite the sensor window from the second set of electrode contacts.

Example 60 is the wearable monitoring device of example(s) 59, wherein each of the first set of electrode contacts are positioned in a first line, wherein each of the second set of electrode contacts are positioned in a second line, and wherein the first line is parallel to the second line.

Example 61 is the wearable monitoring device of example(s) 53-60, wherein the first set of electrode contacts is positioned opposite the sensor window from the second set of electrode contacts in a first direction, and wherein at least one of the ACM sensors is positioned opposite a line collinear with the first direction from another of the ACM sensors.

Example 62 is the wearable monitoring device of example(s) 53-61, wherein the bottom surface of the electronics module further comprises an environmental sensor capable of sensing temperature, humidity, or a combination of temperature and humidity.

Example 63 is the wearable monitoring device of example(s) 62, wherein the environmental sensor includes an insulation wall that makes contact with the skin of the user when the electronics module is positioned against the skin of the user, and wherein the insulation wall, the environmental sensor, and the skin define an enclosed environment when the electronics module is positioned against the skin of the user.

Example 64 is the wearable monitoring device of example(s) 53-63, wherein the electronics module includes a rechargeable battery.

Example 65 is a method, comprising: providing an electronics module, the electronics module positionable against skin of a user, the electronics module having a bottom surface comprising: a set of accelerometer contact microphone (ACM) sensors extending outwards from the bottom surface, each of the ACM sensors having a sensing surface for contacting against the skin of the user; a sensor window covering a set of non-contact sensors positioned behind the sensor window, wherein a bottom surface of the sensor window is coplanar with the sensing surfaces of the set of ACM sensors; and a first set of electrode contacts and a second set of electrode contacts extending outwards from the bottom surface, wherein the first set of electrode contacts and second set of electrode contacts are coupled to a printed circuit board (PCB) for conveying electrical signals between the skin of the user and the PCB, and wherein each electrode contact of the first set of electrode contacts is paired with a corresponding electrode contact of the second set of electrode contacts; providing a flexible patch securable to the skin of the user, the flexible patch comprising: a receptacle for receiving the electronics module, wherein the electronics module comprises one or more interlocking features that engage one or more corresponding interlocking features of the receptacle to removably secure the electronics module within the receptacle; a set of electrode pads electrically couplable to the skin of the user when the flexible patch is secured to the skin of the user; and a set of flexible traces connecting the set of electrode pads with the plurality of electrode contacts of the electronics module when the electronics module is removably secured within the receptacle; placing the electronics module in the receptacle of the flexible patch; securing the flexible patch to the skin of the user; and acquiring physiological data using the set of ACM sensors, the set of non-contact sensors, the first set of electrode contacts, and the second set of electrode contacts.

Example 66 is the method of example(s) 65, wherein securing the flexible patch to the skin of the user includes exposing an adhesive layer of the flexible patch and pressing the adhesive layer of the flexible patch against the skin of the user, wherein the set of ACM sensors contact the skin of the user when the adhesive layer is pressed against the skin of the user.

Example 67 is the method of example(s) 65 or 66, further comprising: removing the electronics module from the receptacle of the flexible patch while the flexible patch is secured to the skin of the user; recharging the electronics module; and replacing the electronics module into the receptacle of the flexible patch while the flexible patch remains secured to the skin of the user.

Example 68 is the method of example(s) 65-67, further comprising: removing the electronics module from the receptacle of the flexible patch; coupling the electronics module to a second flexible patch; and securing the second flexible patch to the skin of the user.

Example 69 is the method of example(s) 65-68, wherein the first set of electrode contacts is positioned opposite the sensor window from the second set of electrode contacts.

Example 70 is the method of example(s) 69, wherein each of the first set of electrode contacts are positioned in a first line, wherein each of the second set of electrode contacts are positioned in a second line, and wherein the first line is parallel to the second line.

Example 71 is the method of example(s) 65-70, wherein the bottom surface of the electronics module further comprises an environmental sensor capable of sensing temperature, humidity, or a combination of temperature and humidity.

Example 72 is the method of example(s) 71, wherein the environmental sensor includes an insulation wall that makes contact with the skin of the user when the electronics module is positioned against the skin of the user, and wherein the insulation wall, the environmental sensor, and the skin define an enclosed environment when the electronics module is positioned against the skin of the user.

What is claimed is:

1. A wearable monitoring device, comprising:
an electronics module positionable against skin of a user, the electronics module having a bottom surface comprising:
   a set of accelerometer contact microphone (ACM) sensors extending outwards from the bottom surface, each of the ACM sensors having a sensing surface for contacting against the skin of the user;
   a sensor window covering a set of non-contact sensors positioned behind the sensor window, wherein a bottom surface of the sensor window is coplanar with the sensing surfaces of the set of ACM sensors; and
   a first set of electrode contacts and a second set of electrode contacts extending outwards from the bottom surface, wherein the first set of electrode contacts and second set of electrode contacts are coupled to a printed circuit board (PCB) for conveying electrical signals between the skin of the user and the PCB, and wherein each electrode contact of the first set of electrode contacts is paired with a corresponding electrode contact of the second set of electrode contacts.

2. The wearable monitoring device of claim 1, further comprising a flexible patch securable to the skin of the user, the flexible patch comprising:
   a receptacle for receiving the electronics module, wherein the electronics module comprises one or more interlocking features that engage one or more corresponding interlocking features of the receptacle to removably secure the electronics module within the receptacle;
   a set of electrode pads electrically couplable to the skin of the user when the flexible patch is secured to the skin of the user; and
   a set of flexible traces connecting the set of electrode pads with the plurality of electrode contacts of the electronics module when the electronics module is removably secured within the receptacle.

3. The wearable monitoring device of claim 2, wherein the receptacle includes at least one opening for receiving the set of ACM sensors and the sensor window therethrough when the electronics module is removably secured within the receptacle.

4. The wearable monitoring device of claim 3, wherein the flexible patch includes an adhesive layer for securing the flexible patch to the skin of the user, and wherein the sensing surfaces of the ACM sensors extend from the bottom surface of the electronics module by a distance sufficient to contact the skin of the user when the adhesive layer of the flexible patch secures the flexible patch to the skin of the user.

5. The wearable monitoring device of claim 4, wherein the sensing surfaces of the ACM sensors extend from the bottom surface of the electronics module to a distance of between 1 mm and 4 mm past the adhesive layer when the electronics module is removably secured within the receptacle.

6. The wearable monitoring device of claim 3, wherein the at least one opening of the receptacle includes a discrete opening for each of the set of ACM sensors and an additional opening for the sensor window.

7. The wearable monitoring device of claim 1, wherein the first set of electrode contacts is positioned opposite the sensor window from the second set of electrode contacts.

8. The wearable monitoring device of claim 7, wherein each of the first set of electrode contacts are positioned in a first line, wherein each of the second set of electrode contacts are positioned in a second line, and wherein the first line is parallel to the second line.

9. The wearable monitoring device of claim 1, wherein the first set of electrode contacts is positioned opposite the sensor window from the second set of electrode contacts in a first direction, and wherein at least one of the ACM sensors is positioned opposite a line collinear with the first direction from another of the ACM sensors.

10. The wearable monitoring device of claim 1, wherein the bottom surface of the electronics module further comprises an environmental sensor capable of sensing temperature, humidity, or a combination of temperature and humidity.

11. The wearable monitoring device of claim 10, wherein the environmental sensor includes an insulation wall that makes contact with the skin of the user when the electronics module is positioned against the skin of the user, and wherein the insulation wall, the environmental sensor, and the skin define an enclosed environment when the electronics module is positioned against the skin of the user.

12. The wearable monitoring device of claim 1, wherein the electronics module includes a rechargeable battery.

13. A method, comprising:
providing an electronics module, the electronics module positionable against skin of a user, the electronics module having a bottom surface comprising:
a set of accelerometer contact microphone (ACM) sensors extending outwards from the bottom surface, each of the ACM sensors having a sensing surface for contacting against the skin of the user;
a sensor window covering a set of non-contact sensors positioned behind the sensor window, wherein a bottom surface of the sensor window is coplanar with the sensing surfaces of the set of ACM sensors; and
a first set of electrode contacts and a second set of electrode contacts extending outwards from the bottom surface, wherein the first set of electrode contacts and second set of electrode contacts are coupled to a printed circuit board (PCB) for conveying electrical signals between the skin of the user and the PCB, and wherein each electrode contact of the first set of electrode contacts is paired with a corresponding electrode contact of the second set of electrode contacts;
providing a flexible patch securable to the skin of the user, the flexible patch comprising:
a receptacle for receiving the electronics module, wherein the electronics module comprises one or more interlocking features that engage one or more corresponding interlocking features of the receptacle to removably secure the electronics module within the receptacle;
a set of electrode pads electrically couplable to the skin of the user when the flexible patch is secured to the skin of the user; and
a set of flexible traces connecting the set of electrode pads with the plurality of electrode contacts of the electronics module when the electronics module is removably secured within the receptacle;
placing the electronics module in the receptacle of the flexible patch;
securing the flexible patch to the skin of the user; and
acquiring physiological data using the set of ACM sensors, the set of non-contact sensors, the first set of electrode contacts, and the second set of electrode contacts.

14. The method of claim 13, wherein securing the flexible patch to the skin of the user includes exposing an adhesive layer of the flexible patch and pressing the adhesive layer of the flexible patch against the skin of the user, wherein the set of ACM sensors contact the skin of the user when the adhesive layer is pressed against the skin of the user.

15. The method of claim 13, further comprising:
removing the electronics module from the receptacle of the flexible patch while the flexible patch is secured to the skin of the user;
recharging the electronics module; and
replacing the electronics module into the receptacle of the flexible patch while the flexible patch remains secured to the skin of the user.

16. The method of claim 13, further comprising:
removing the electronics module from the receptacle of the flexible patch;
coupling the electronics module to a second flexible patch; and
securing the second flexible patch to the skin of the user.

17. The method of claim 13, wherein the first set of electrode contacts is positioned opposite the sensor window from the second set of electrode contacts.

18. The method of claim 17, wherein each of the first set of electrode contacts are positioned in a first line, wherein each of the second set of electrode contacts are positioned in a second line, and wherein the first line is parallel to the second line.

19. The method of claim 13, wherein the bottom surface of the electronics module further comprises an environmental sensor capable of sensing temperature, humidity, or a combination of temperature and humidity.

20. The method of claim 19, wherein the environmental sensor includes an insulation wall that makes contact with the skin of the user when the electronics module is positioned against the skin of the user, and wherein the insulation wall, the environmental sensor, and the skin define an enclosed environment when the electronics module is positioned against the skin of the user.

* * * * *